United States Patent
Korb et al.

(10) Patent No.: US 10,842,670 B2
(45) Date of Patent: Nov. 24, 2020

(54) APPARATUSES AND METHODS FOR DIAGNOSING AND/OR TREATING LIPID TRANSPORT DEFICIENCY IN OCULAR TEAR FILMS, AND RELATED COMPONENTS AND DEVICES

(71) Applicant: TearScience, Inc., Morrisville, NC (US)

(72) Inventors: Donald R. Korb, Boston, MA (US); Steve Bacich, Half Moon Bay, CA (US); Caroline Blackie, North Andover, MA (US); Stephen M. Grenon, Durham, NC (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 605 days.

(21) Appl. No.: 14/422,948

(22) PCT Filed: Aug. 22, 2013

(86) PCT No.: PCT/US2013/056199
§ 371 (c)(1),
(2) Date: Feb. 20, 2015

(87) PCT Pub. No.: WO2014/031857
PCT Pub. Date: Feb. 27, 2014

(65) Prior Publication Data
US 2015/0216725 A1    Aug. 6, 2015

Related U.S. Application Data

(60) Provisional application No. 61/691,948, filed on Aug. 22, 2012.

(51) Int. Cl.
*A61F 9/007* (2006.01)
*A61B 17/32* (2006.01)
*A61B 90/00* (2016.01)

(52) U.S. Cl.
CPC .... *A61F 9/00718* (2013.01); *A61B 17/32002* (2013.01); *A61B 2017/320008* (2013.01);
(Continued)

(58) Field of Classification Search
CPC ..... A61F 9/007–00718; A61F 9/00772; A61B 7/32; A61B 17/32002;
(Continued)

(56) References Cited

U.S. PATENT DOCUMENTS

| | | |
|---|---|---|
| 1,006,945 A | 10/1911 | Houston |
| 1,359,870 A | 11/1920 | Buckland |

(Continued)

FOREIGN PATENT DOCUMENTS

| | | |
|---|---|---|
| AU | 2011302478 A1 | 3/2013 |
| CA | 2331257 A1 | 11/1999 |

(Continued)

OTHER PUBLICATIONS

No Author, "arGentis Licenses Third Treatment for Dry Eye Syndrome", Business Wire, May 12, 2008, accessed Jun. 4, 2008, 2 pages.

(Continued)

*Primary Examiner* — Wade Miles
*Assistant Examiner* — Kankindi Rwego

(57) ABSTRACT

Methods and apparatuses are disclosed for the diagnosis and removal of the devitalized and/or dead cell material formed in the lid margin to attempt to restore a normal lid margin. In this manner, the devitalized and/or dead cell material are removed or the amount present is reduced or no longer present to prevent, reduce, or affect the transport of lipid secreted by the meibomian glands to the tear film to reduce evaporative dry eye and improve dry eye conditions in patients. The diagnosis and removal of devitalized and/or dead cell material may be performed at desired intervals.

(Continued)

Patients that suffer from conditions that block meibomian gland orifices, partial, infrequent, or inhibited blinking resulting in reduced lipid secretions from meibomian glands, and/or blockages in meibomian gland channels reducing secretion of lipids through the meibomian gland orifices may require more frequent diagnosis and treatment to remove devitalized and/or dead cell material.

32 Claims, 54 Drawing Sheets

(52) U.S. Cl.
CPC ............ *A61B 2017/320012* (2013.01); *A61B 2090/0817* (2016.02)

(58) Field of Classification Search
CPC ............... A61B 2017/320004–320008; A61B 2017/320024–320032; A61B 2018/00964–00976
See application file for complete search history.

(56) References Cited

U.S. PATENT DOCUMENTS

| | | |
|---|---|---|
| 1,924,315 A | 8/1933 | Hemphill et al. |
| 2,545,724 A | 3/1951 | Curtis |
| 2,891,252 A | 6/1959 | Lazo |
| 3,140,390 A | 7/1964 | Smith et al. |
| 3,173,419 A | 3/1965 | Dubilier et al. |
| 3,333,586 A | 8/1967 | Bellis et al. |
| 3,404,678 A | 10/1968 | Von Ardenne |
| 3,415,299 A | 12/1968 | Hinman, Jr. et al. |
| 3,667,476 A | 6/1972 | Muller |
| 3,937,222 A * | 2/1976 | Banko ................. A61F 9/00763 606/107 |
| 3,952,735 A | 4/1976 | Wirtschafter et al. |
| 4,069,084 A | 1/1978 | Mlodozeniec et al. |
| 4,131,115 A | 12/1978 | Peng |
| 4,261,364 A | 4/1981 | Haddad et al. |
| 4,387,707 A | 6/1983 | Polikoff |
| 4,778,457 A | 10/1988 | York |
| 4,883,454 A | 11/1989 | Hamburg |
| 4,914,088 A | 4/1990 | Glonek et al. |
| 4,918,818 A | 4/1990 | Hsieh |
| 4,955,377 A | 9/1990 | Lennox et al. |
| 4,958,632 A | 9/1990 | Duggan |
| 5,030,214 A | 7/1991 | Spector |
| 5,097,829 A | 3/1992 | Quisenberry |
| 5,151,100 A | 9/1992 | Abele et al. |
| 5,158,082 A | 10/1992 | Jones |
| 5,169,384 A | 12/1992 | Bosniak et al. |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,327,886 A | 7/1994 | Chiu |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,377,701 A | 1/1995 | Fang |
| 5,419,772 A | 5/1995 | Teitz et al. |
| 5,425,380 A | 6/1995 | Hudson et al. |
| 5,496,311 A | 3/1996 | Abele et al. |
| 5,601,548 A | 2/1997 | Smith et al. |
| 5,628,772 A | 5/1997 | Russell |
| 5,643,336 A | 7/1997 | Lopez-Claros |
| 5,700,238 A | 12/1997 | Hyson |
| 5,720,773 A | 2/1998 | Lopez-Claros |
| 5,769,806 A | 6/1998 | Radow |
| 5,782,857 A | 7/1998 | Machuron |
| 5,807,357 A | 9/1998 | Kang |
| 5,836,927 A | 11/1998 | Fried |
| 5,893,719 A | 4/1999 | Radow |
| 5,958,912 A | 9/1999 | Sullivan |
| 5,960,608 A | 10/1999 | Ohtonen |
| 5,964,723 A | 10/1999 | Augustine |
| 6,007,501 A | 12/1999 | Cabados et al. |
| 6,024,095 A | 2/2000 | Stanley, III |
| 6,090,060 A | 7/2000 | Radow |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,153,607 A | 11/2000 | Pflugfelder et al. |
| 6,155,995 A | 12/2000 | Lin |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| 6,275,735 B1 | 8/2001 | Jarding et al. |
| 6,309,364 B1 | 10/2001 | Cathaud et al. |
| 6,312,397 B1 | 11/2001 | Gebhard |
| D456,079 S | 4/2002 | Fujii |
| 6,423,018 B1 | 7/2002 | Augustine |
| 6,425,888 B1 | 7/2002 | Embleton et al. |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,257 B2 | 4/2003 | Nagase et al. |
| D477,084 S | 7/2003 | Menezes et al. |
| 6,641,264 B1 | 11/2003 | Schwebel |
| 6,648,904 B2 | 11/2003 | Altshuler et al. |
| 6,706,001 B2 | 3/2004 | Fresco |
| 6,780,176 B2 | 8/2004 | Hasegawa |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,908,195 B2 | 6/2005 | Fuller |
| 6,925,317 B1 | 8/2005 | Samuels et al. |
| 6,974,454 B2 | 12/2005 | Hooven |
| 7,001,379 B2 | 2/2006 | Behl et al. |
| 7,004,942 B2 | 2/2006 | Laird et al. |
| 7,036,928 B2 | 5/2006 | Schwebel |
| 7,069,084 B2 | 6/2006 | Yee |
| 7,108,694 B2 | 9/2006 | Miura et al. |
| 7,118,591 B2 | 10/2006 | Frank et al. |
| 7,122,013 B2 | 10/2006 | Liu |
| 7,122,047 B2 | 10/2006 | Grahn et al. |
| 7,123,968 B1 | 10/2006 | Casscells, III et al. |
| 7,211,070 B2 | 5/2007 | Soroudi |
| 7,229,468 B2 | 6/2007 | Wong et al. |
| 7,231,922 B2 | 6/2007 | Davison et al. |
| D546,459 S | 7/2007 | Banryu |
| D552,736 S | 10/2007 | Yamaoka |
| D553,750 S | 10/2007 | Yamaoka |
| 7,316,657 B2 | 1/2008 | Kleinhenz et al. |
| 7,357,500 B2 | 4/2008 | Schwebel |
| 7,384,405 B2 | 6/2008 | Rhoades |
| 7,442,174 B2 | 10/2008 | Butler |
| 7,513,893 B2 | 4/2009 | Soroudi |
| 7,559,907 B2 | 7/2009 | Krempel et al. |
| 7,594,728 B2 | 9/2009 | Seal et al. |
| 7,637,878 B2 | 12/2009 | Lin |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 | 7/2011 | Korb et al. |
| 7,981,146 B2 * | 7/2011 | Korb .................. A61F 9/00772 128/898 |
| D645,565 S | 9/2011 | Smith et al. |
| 8,025,689 B2 | 9/2011 | Korb et al. |
| 8,083,787 B2 | 12/2011 | Korb et al. |
| 8,128,673 B2 | 3/2012 | Korb et al. |

(56) References Cited

U.S. PATENT DOCUMENTS

| | | |
|---|---|---|
| 8,128,674 B2 | 3/2012 | Korb et al. |
| 8,137,390 B2 | 3/2012 | Korb et al. |
| 8,187,311 B2 | 5/2012 | Korb et al. |
| 8,262,715 B2 | 9/2012 | Wong, Jr. et al. |
| 8,455,016 B2 | 6/2013 | Maskin |
| 8,617,229 B2 | 12/2013 | Korb et al. |
| 8,628,504 B2 | 1/2014 | Grenon et al. |
| 8,791,158 B2 | 7/2014 | Dalton et al. |
| 8,906,427 B2 | 12/2014 | Maskin |
| 8,956,311 B2 | 2/2015 | Korb et al. |
| 9,039,718 B2 | 5/2015 | Rynerson |
| 2001/0039442 A1 | 11/2001 | Gorge et al. |
| 2001/0041886 A1 | 11/2001 | Durkin et al. |
| 2002/0035345 A1 | 3/2002 | Beck |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2002/0156402 A1 | 10/2002 | Woog et al. |
| 2003/0050594 A1 | 3/2003 | Zamierowski |
| 2003/0056281 A1 | 3/2003 | Hasegawa |
| 2003/0065277 A1 | 4/2003 | Covington |
| 2003/0073987 A1 | 4/2003 | Sakurai et al. |
| 2003/0100936 A1 | 5/2003 | Altshuler et al. |
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0220656 A1* | 11/2003 | Gartstein ............ A45D 26/0004 606/131 |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0199158 A1 | 10/2004 | Hood et al. |
| 2004/0237969 A1 | 12/2004 | Fuller |
| 2004/0249427 A1 | 12/2004 | Nabilsi |
| 2004/0260209 A1 | 12/2004 | Ella et al. |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0187502 A1 | 8/2005 | Krempel et al. |
| 2005/0220742 A1 | 10/2005 | Breen |
| 2005/0234506 A1 | 10/2005 | Weser |
| 2006/0018953 A1 | 1/2006 | Guillon et al. |
| 2006/0030604 A1 | 2/2006 | Elsinger et al. |
| 2006/0055878 A1 | 3/2006 | Yee |
| 2006/0069420 A1 | 3/2006 | Rademacher et al. |
| 2006/0104914 A1 | 5/2006 | Soroudi |
| 2006/0135890 A1 | 6/2006 | Tsai |
| 2006/0136022 A1 | 6/2006 | Wong, Jr. et al. |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0212101 A1 | 9/2006 | Cheng |
| 2006/0233859 A1 | 10/2006 | Whitcup et al. |
| 2007/0016254 A1* | 1/2007 | Grenon ............... A61F 9/00772 607/1 |
| 2007/0016255 A1 | 1/2007 | Korb et al. |
| 2007/0016256 A1 | 1/2007 | Korb et al. |
| 2007/0027411 A1 | 2/2007 | Ella et al. |
| 2007/0049913 A1 | 3/2007 | Grenon et al. |
| 2007/0173799 A1 | 7/2007 | Hsia |
| 2007/0203462 A1 | 8/2007 | Soroudi |
| 2007/0270760 A1 | 11/2007 | Dacquay et al. |
| 2007/0280924 A1 | 12/2007 | Daniels et al. |
| 2007/0282282 A1 | 12/2007 | Wong, Jr. et al. |
| 2008/0051741 A1 | 2/2008 | Grenon et al. |
| 2008/0075787 A1 | 3/2008 | Hibino |
| 2008/0081999 A1 | 4/2008 | Gravely et al. |
| 2008/0082057 A1 | 4/2008 | Korb et al. |
| 2008/0114423 A1 | 5/2008 | Grenon et al. |
| 2008/0114424 A1 | 5/2008 | Grenon et al. |
| 2008/0132973 A1 | 6/2008 | Lord et al. |
| 2008/0188811 A1 | 8/2008 | Kim |
| 2008/0200848 A1 | 8/2008 | Avni |
| 2008/0275468 A1* | 11/2008 | Chuang ................. A61B 5/442 606/131 |
| 2009/0043365 A1 | 2/2009 | Friedland et al. |
| 2009/0137533 A1 | 5/2009 | Adkins, Jr. |
| 2009/0192478 A1 | 7/2009 | Soroudi |
| 2009/0222023 A1* | 9/2009 | Boone, III ........... A61B 17/545 606/131 |
| 2009/0306111 A1 | 12/2009 | Nakamura et al. |
| 2009/0306607 A1 | 12/2009 | Yasuhiro |
| 2010/0100029 A1 | 4/2010 | Maskin |
| 2010/0292630 A1 | 11/2010 | Maskin |
| 2011/0022010 A1 | 1/2011 | Grenon et al. |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0124725 A1 | 5/2011 | Maskin |
| 2011/0130729 A1 | 6/2011 | Korb et al. |
| 2011/0172302 A1 | 7/2011 | Dalton et al. |
| 2011/0203832 A1 | 8/2011 | Schrock |
| 2011/0251532 A1 | 10/2011 | Yang |
| 2011/0273550 A1 | 11/2011 | Amano et al. |
| 2011/0294897 A1 | 12/2011 | Aberg et al. |
| 2012/0003296 A1 | 1/2012 | Shantha et al. |
| 2012/0016275 A1 | 1/2012 | Korb et al. |
| 2012/0065556 A1 | 3/2012 | Smith et al. |
| 2012/0093876 A1 | 4/2012 | Ousler, III et al. |
| 2012/0109041 A1 | 5/2012 | Munz |
| 2012/0128763 A1 | 5/2012 | Maskin |
| 2012/0136285 A1 | 5/2012 | Korb et al. |
| 2012/0143102 A1 | 6/2012 | Korb et al. |
| 2012/0197360 A1 | 8/2012 | Korb et al. |
| 2012/0209154 A1 | 8/2012 | Williams, III et al. |
| 2012/0220612 A1 | 8/2012 | Nakamura et al. |
| 2012/0321673 A1 | 12/2012 | Ogawa et al. |
| 2013/0045927 A1 | 2/2013 | Dana et al. |
| 2013/0046367 A1 | 2/2013 | Chen |
| 2013/0053733 A1 | 2/2013 | Korb et al. |
| 2013/0065867 A1 | 3/2013 | Smith et al. |
| 2013/0110101 A1 | 5/2013 | Van Valen et al. |
| 2013/0131171 A1 | 5/2013 | Maskin |
| 2013/0172790 A1 | 7/2013 | Badawi |
| 2013/0172829 A1 | 7/2013 | Badawi |
| 2014/0031845 A1 | 1/2014 | Rynerson |
| 2014/0052164 A1 | 2/2014 | Rynerson |
| 2014/0214062 A1 | 7/2014 | Rynerson et al. |
| 2014/0330129 A1 | 11/2014 | Grenon et al. |
| 2014/0378878 A1 | 12/2014 | Sharma et al. |
| 2015/0005750 A1 | 1/2015 | Kelleher et al. |
| 2015/0038851 A1 | 2/2015 | Hamrah et al. |
| 2015/0057701 A1 | 2/2015 | Kelleher et al. |
| 2015/0100001 A1 | 4/2015 | Bujak |
| 2015/0182415 A1 | 7/2015 | Olkowski et al. |

FOREIGN PATENT DOCUMENTS

| | | |
|---|---|---|
| CA | 2679448 A1 | 9/2008 |
| CA | 2787114 A1 | 7/2011 |
| CA | 2809274 A1 | 3/2012 |
| CN | 2650737 Y | 10/2004 |
| CN | 1631344 A | 6/2005 |
| CN | 2855388 Y | 1/2007 |
| CN | 102204854 A | 10/2011 |
| CN | 101663064 B | 3/2013 |
| CN | 103002737 A | 3/2013 |
| CN | 102600008 B | 5/2014 |
| CN | 102697593 B | 12/2014 |
| CN | 102697595 B | 12/2014 |
| CN | 104203190 A | 12/2014 |
| DE | 202005011496 U1 | 7/2006 |
| EP | 1816980 A2 | 8/2007 |
| EP | 2151438 A1 | 2/2010 |
| EP | 1587468 B1 | 1/2011 |
| EP | 2523556 A1 | 11/2012 |
| JP | H0370557 A | 3/1991 |
| JP | 06269473 A | 9/1994 |
| JP | H06315499 A | 11/1994 |

(56) References Cited

FOREIGN PATENT DOCUMENTS

| | | | |
|---|---|---|---|
| JP | 10085248 A | 4/1998 |
| JP | 11221247 | 8/1999 |
| JP | 2000225141 A | 8/2000 |
| JP | 2001276113 A | 10/2001 |
| JP | 2002078727 A | 3/2002 |
| JP | 2004350803 A | 12/2004 |
| JP | U3112008 B | 7/2005 |
| JP | 2005237724 A | 9/2005 |
| JP | 2006198249 A | 8/2006 |
| JP | 2010155012 A | 7/2010 |
| JP | 2014205069 A | 10/2014 |
| KR | 20120115380 A | 10/2012 |
| MX | 2012008110 A | 10/2012 |
| WO | 9810723 A1 | 3/1998 |
| WO | 9920213 A1 | 4/1999 |
| WO | 9958131 A1 | 11/1999 |
| WO | 2004041134 A1 | 5/2004 |
| WO | 2006058189 A2 | 6/2006 |
| WO | 2006093851 A2 | 9/2006 |
| WO | 2008024100 A2 | 2/2008 |
| WO | 2008085162 A1 | 7/2008 |
| WO | 2008106228 A2 | 9/2008 |
| WO | 2009064834 A2 | 5/2009 |
| WO | 2010005527 A1 | 1/2010 |
| WO | 2010056848 A1 | 5/2010 |
| WO | 2011085385 A1 | 7/2011 |
| WO | 2012036931 A1 | 3/2012 |
| WO | 2012051313 A2 | 4/2012 |
| WO | 2012137545 A1 | 10/2012 |
| WO | 2013003594 A2 | 1/2013 |
| WO | 2013003594 A3 | 1/2013 |
| WO | 2013003731 A3 | 1/2013 |
| WO | 2013006574 A1 | 1/2013 |
| WO | 2013036894 A2 | 3/2013 |
| WO | 2013114127 A1 | 8/2013 |
| WO | 2013126599 A1 | 8/2013 |
| WO | 2013149318 A1 | 10/2013 |
| WO | 2013166353 A1 | 11/2013 |
| WO | 2014031857 A2 | 2/2014 |
| WO | 2014049841 A1 | 4/2014 |
| WO | 2014158356 A1 | 10/2014 |
| WO | 2014179356 A1 | 11/2014 |
| WO | 2014179795 A2 | 11/2014 |

OTHER PUBLICATIONS

No Author, "New Over-the-Counter Dry Eye Drop Now Available to Help Estimated 40 Percent of Americans Who Suffer from Occasional or Chronic Dry Eye", Business Wire News Release, Mar. 31, 2008, accessed Jun. 5, 2008, 4 pages.
Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.
Aronowicz, JD et al. "Short Term Oral Minocycline Treatment of Meibomiantis," Br. J. Ophthalmol, vol. 90, No. 7, Jul. 2006, pp. 856-860.
Blackie, Caroline A. et al., "Inner Eyelid Surface Temperature as a Function of Warm Compress Methodology," Optometry and Vision Science, vol. 85, No. 8, Aug. 2008, pp. 675-683.
Blackie, Caroline A. et al., "Nonobvious Obstructive Meibomian Gland Dysfunction," Cornea, vol. 29, No. 12, Dec. 2010, pp. 1333-1345.
Blackie, Caroline A. et al., "Recovery Time of an Optimally Secreting Meibomian Gland," Cornea, vol. 28, No. 3, Apr. 2009, pp. 293-297.
Butovich, Igor et al., "Meibomian Lipid Films and the Impact of Temperature," Investigative Opthalmology & Visual Science, vol. 51, No. 11, Jul. 2010, pp. 5508-5518.
Cunniffe, M. Geraldine et al., "Topical Antiglaucoma Treatment with Prostaglandin Analogues May Precipitate Meibomian Gland Disease," Ophthalmic Plastic and Reconstructive Surgery, Sep.-Oct. 2011, vol. 27, No. 5, Lippincott Williams and Wilkins, Philadelphia, PA, p. 128-129.
Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Foulks, Gary N. et al., "Meibomian Gland Dysfunction: The Past, Present, and Future," Eye and Contact Lens, vol. 36, No. 5, Sep. 2010, pp. 249-253.
Friedland, B., et al., "A Novel Thermodynamic Treatment for Meibomian Gland Dysfunction," Current Eye Research, vol. 36, No. 2, Feb. 2011, pp. 79-87.
Geerling, G., et al., "The international workshop on meibomian gland dysfunction: report of the subcommittee on management and treatment of meibomian gland dysfunction," Mar. 2011, Investigative Ophthalmology & Visual Science, vol. 52, No. 4., pp. 2050-2064.
Goto, E., et al. "Treatment of Non-Inflamed Obstructive Meibomian Gland Dysfunction by an Infrared Warm Compression Device," Br. J. Ophthalmology, vol. 86, Dec. 2002, pp. 1403-1407.
Goto, Eiki, et al., "Tear Evaporation Dynamics in Normal Subjects and Subjects with Obstructive Meibomian Gland Dysfunction," Investigative Ophthalmology & Visual Science, vol. 44, No. 2, Feb. 2003, pp. 533-539.
Greiner, J., "A Single LipiFlow Thermal Pulsation System Treatment Improves Meibomian Gland Function and Reduces Dry Eye Symptoms for 9 months," Current Eye Research, vol. 37 No. 4, Apr. 2012, pp. 272-278.
Gupta, S. et al. "Docetaxel-Induced Meibomian Duct Inflammation and Blockage Leading to Chalazion Formation," Prostate Cancer and Prostatic Diseases, vol. 10, No. 4, Apr. 2007, pp. 396-397.
Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.
Holifield, Karintha and Lazzaro, Douglas R., "Case report: Spontaneous stenotrophomonas maltophilia keratitis in a diabetic patient," Eye and Contact Lens, Sep. 2011, vol. 37, No. 5, Philadelphia PA, pp. 326-327.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Kokke, K.H. et al., "Oral Omega-6 Essential Fatty Acid Treatment in Contact Lens Associated Dry Eye," Contact Lens and Anterior Eye, vol. 31, No. 3, Jun. 2008, pp. 141-146.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. and Blackie, Caroline A., "Meibomian gland therapeutic expression: Quantifying the applied pressure and the limitation of resulting pain," Eye and Contact Lens, Sep. 2011, vol. 37, No. 5, Philadelphia, PA, pp. 298-301.
Korb, Donald R. et al., "Increase in Tear Film Lipid Layer Thickness Following Treatment of Meibomian Gland Dysfunction", Lacrimal Gland, Tear Film & Dry Eye Syndromes, vol. 350, Plenum Press, 1994, pp. 293-298.
Korb, Donald R. et al., "Lid Wiper Epitheliopathy and Dry Eye Symptoms," Eye & Contact Lens, vol. 31, No. 1, Jan. 2005, pp. 2-8.
Korb, Donald R. et al., "Restoration of Meibomian Gland Functionality with Novel Thermodynamic Treatment Device—A Case Report," Cornea, vol. 29, No. 8, Aug. 2010, pp. 930-933.

(56) References Cited

OTHER PUBLICATIONS

Korb, Donald R. et al., "Tear Film Lipid Layer Thickness as a Function of Blinking," Cornea, vol. 13, No. 4, Jul. 1994, pp. 354-359.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.
Korb, Donald R., O.D., et al., "Meibomian Gland Dysfunction and Contact Lens Intolerance," Journal of the American Optometric Association, vol. 51, No. 3, Mar. 1980, pp. 243-251.
Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.
Kuscu, Naci Kemal, et al., "Tear Function Changes of Postmenopausal Women in Response to Hormone Replacement Therapy," Maturitas, vol. 44, Jan. 2003pp. 63-68.
Lane, S. et al., "A New System, the LipiFlow, for the Treatment of Meibomian Gland Dysfunction," Cornea, vol. 31, No. 4, Apr. 2012, pp. 396-404.
Lemp, Michael A. et al., "Blepharitis in the United States 2009: A Survey-Based Perspective on Prevalence and Treatment." Oculular Surface, vol. 7, No. 2 Supplement, Apr. 2009, 36 pages.
Lemp, Michael A., et al., "The Therapeutic Role of Lipids—Managing Ocular Surface Disease," Supplement to Refractive Eyecare of Ophthalmologists, vol. 9, No. 6, Jun. 2005, 14 pages.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Unknown, "Introducing: Thermofoil Heaters", Minco Bulletin HS-202, 2002, 9 pages.
Mitra, M. et al., "Tear Film Lipid Layer Thickness and Ocular Comfort after Meibomian Therapy via Latent Heat with a Novel Device in Normal Subjects," Eye, Jun. 2005, pp. 657-660.
Mori, A., et al., "Efficacy of the Treatment by the Disposable Eyelid Warming Instrument for Meibomian Gland Dysfunction," Poster Presentation, Hall A, The Association for Research and Vision in Ophthalmology Annual Meeting, Fort Lauderdale, Florida, Apr. 30, 2000, 1 page.
Mori, Asako, et al., "Disposable Eyelid-Warming Device for the Treatment of Meibomian Gland Dysfunction", Japan Journal of Ophthalmology, vol. 47, pp. 578-586, 2003.
Olson, Mary Catherine, B.A., et al., "Increase in Tear Film Lipid Layer Thickness Following Treatment with Warm Compresses in Patients with Meibomian Gland Dysfunction," Eye & Contact Lens, vol. 29, No. 2, Apr. 2003, pp. 96-99.
Paugh, J.R. et al., "Meibomian Therapy in Problematic Contact Lens Wear," Entrez PubMed, Optom Vis Sci, vol. 67, No. 11, Nov. 1990, pp. 803-806 (abstract only).
Paugh, Jerry R. et al., "Precorneal Residence Time of Artificial Tears Measured in Dry Eye Subjects," Optometry and Vision Science, vol. 85, No. 8, Aug. 2008, pp. 725-731.
Romero, Juan M., et al., "Conservative Treatment of Meibomian Gland Dysfunction," Contact Lens Association of Ophthalmology, Eye & Contact Lens, vol. 30, No. 1, Jan. 2004, pp. 14-19.
Sullivan, Benjamin D., et al., "Impact of Antiandrogen Treatment on the Fatty Acid Profile of Neutral Lipids in Human Meibomian Gland Secretions," Journal of Clinical Endocrinology & Metabolism, vol. 85, No. 12, Dec. 2000, pp. 4866-4873.
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Suzuki, Tomo et al., "Estrogen and Progesterone Control of Gene Expression in the Mouse Meibomian Gland," Invest. Ophthalmol. Vis. Sci., vol. 49, No. 5, May 2008, pp. 1797-1818.
Abelson, Mark B. et al., "A Tentative Mechanism for Inferior Punctate Keratopathy," American Journal of Ophthalmology, vol. 83, No. 6, Jun. 1977, pp. 866-869.
Berens, Conrad, "The Eye and Its Diseases: By 82 International Authorities," (book), Anatomy of Orbit, Eyeball and its Adnexa, W.B. Saunders Company, Philadelphia, Pennsylvania, 1936, p. 21.
Bron, Anthony et al., "Wolff's Anatomy of the Eye and Orbit," (book), Eighth Edition, Chapman & Hall Medical, London, United Kingdom, 1997, pp. 33 and 36.
Carney, L.G. et al, "The Nature of Normal Blinking Patterns," Acta Ophthalmologica, vol. 60, Issue 3, Jun. 1982, Blackwell Publishing, pp. 427-433.
Cruz, Antonio A.V. et al., "Spontaneous Eyeblink Activity," The Ocular Surface, vol. 9, No. 1, Jan. 2011, pp. 29-41.
Doane, Marshall G., "Blinking and the Mechanics of the Lacrimal Drainage System," Ophthalmology, vol. 88, No. 8, Aug. 1981, American Academy of Ophthalmology, pp. 844-851.
Doughty, Michael J., "Consideration of Three Types of Spontaneous Eyeblink Activity in Normal Humans: during Reading and Video Display Terminal Use, in Primary Gaze, and while in Conversation," Optometry and Vision Science, vol. 78, No. 10, Oct. 2001, American Academy of Optometry, pp. 712-725.
Foulks, Gary N., "The Correlation Between the Tear Film Lipid Layer and Dry Eye Disease," Survey of Ophthalmology, vol. 52, No. 4, Jul.-Aug. 2007, Elsevier, Inc., pp. 369-374.
Korb, Donald R. et al., "Debridement-Scaling: A New Procedure That Increases Meibomian Gland Function and Reduces Dry Eye Symptoms," Cornea, vol. 32, No. 12, Dec. 2013, Lippincott Williams & Wilkins, pp. 1554-1557.
Korb, Donald R. et al., "Evidence That the Keratinized Upper and Lower Lid Margins Do Not Make Complete Contact Even When the Lids Are Closed," ARVO Annual Meeting, Poster Session, TearScience, Inc., May 1, 2012, 1 page.
Korb, Donald R., "Marx's Line Publication 1924: Critical in Dry Eye Research 86 Years Later," Guest Editorial, Optometry and Vision Science, vol. 87, No. 10, Oct. 2010, American Academy of Optometry, pp. 716-717.
Korb, Donald R. et al., "Meibomian Gland Diagnostic Expressibility: Correlation With Dry Eye Symptoms and Gland Location," Cornea, vol. 27, No. 10, Dec. 2008, Lippincott Williams & Wilkins, pp. 1142-1147.
McMonnies, Charles W., "Incomplete blinking: Exposure keratopathy, lid wiper epitheliopathy, dry eye, refractive surgery, and dry contact lenses," Contact Lens & Anterior Eye, vol. 30, Mar. 2007, Elsevier Ltd., pp. 37-51.
Miller, Kimberly L. et al., "Minimal Clinically Important Difference for the Ocular Surface Disease Index," Archives of Ophthalmology, vol. 128, No. 1, Jan. 2010, American Medical Association, pp. 94-101.
Norn, M., "Meibomian orifices and Marx's line. Studied by triple vital staining," Acta Ophthalmologica, vol. 63, No. 6, Dec. 1985, pp. 698-700 (abstract only).
Pult, Heiko et al., "About Vital Staining of the Eye and Eyelids. I. The Anatomy, Physiology, and Pathology of the Eyelid Margins and the Lacrimal Puncta by E. Marx," Optometry and Vision Science, vol. 87, No. 10, Oct. 2010, American Academy of Optometry, pp. 718-724.
Schiffman, Rhett M. et al., "Reliability and Validity of the Ocular Surface Disease Index," Archives of Ophthalmology, vol. 118, No. 5, May 2000, American Medical Association, pp. 615-621.
Invitation to Pay Additional Fees for PCT/US13/56199 dated Dec. 3, 2013, 2 pages.
International Search Report and Written Opinion for PCT/US13/56199 dated Feb. 7, 2014, 14 pages.
International Preliminary Report on Patentability for PCT/US2013/056199, dated Mar. 5, 2015, 11 pages.
Author Unknown, "BlephEx: Healthy Lids for Life!", Product Brochure, 2013, RySurg, LLC, Milford, Michigan, 14 pages.

(56) References Cited

OTHER PUBLICATIONS

Tobler, David, et al., "Nanotech Silver Fights Microbes in Medical Devices," Medical Device and Diagnostic Industry, May 1, 2005, 6 pages.
Toyos, Rolando, "Intense Pulsed Light for Dry Eye Syndrome," Cataract & Refractive Surgery Today, Apr. 2009, pp. 1-3.
Wolff, Eugene, "Eugene Wolff's Anatomy of the eye and orbit : including the central connexions, development, and comparative anatomy of the visual apparatus (book)," 1976, p. 170.
Unknown, "IFU Manual for PNT Model 1000—Rev H," Feb. 11, 2009, http://www.oi-pnt.com/files/IFU_Manual_Model_1000_English_with_Bargode_Rev_H.pdf, 24 pages.
Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.
Vasta, Stephanie, "Aggressive Treatments Developed for Meibomian Gland Dysfunction," Primary Care Optometry News, Nov. 1, 2009, 3 pages.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Korb, D. et al., "Meibomian gland therapeutic expression: quantifying the applied pressure and the limitation of resulting pain," Eye & Contact Lens, vol. 37 No. 5, Sep. 2011, pp. 298-301.
Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutics, vol. 28 No. 1, Feb. 2, 2012, pp. 49-52.
No Author, "TearScience's LipiFlow Multi-center Clinical Study Shows Improved Meibomian Gland Secretions and Dry Eye Symptoms," Business Wire, Mar. 5, 2012, 2 pages.
Asbell, P. et al. "The international workshop on meibomian gland dysfunction: report of the clinical trials subcommittee," Investigative Ophthalmology and Visual Science, Mar. 2011, pp. 2065-2085.
Foulks et al., "Improving awareness, identification, and management of meibomian gland dysfunction," Ophthalmology, vol. 119, No. 10 Sup., Oct. 2012, 12 pages.
Arita, F. et al., "Comparison of the long-term effects of various topical antiglaucoma medications on meibomian glands," Cornea, vol. 31, No. 11, Nov. 2012, pp. 1229-1234.
Agnifili et al., "In vivo confocal microscopy of meibomian glands in glaucoma," British Journal of Ophthalmology, vol. 97, No. 3, Mar. 2013, pp. 343-349, United Kingdom.
Aragona, P. et al., "Towards a dynamic customised therapy for ocular surface dysfunctions," British Journal of Ophthalmology, vol. 97, No. 8, Aug. 13, pp. 955-960.
Arita, R. et al., "Topical diquafosol for patients with obstructive meibomian gland dysfunction," British Journal of Ophthalmology, vol. 97, No. 6, Jun. 2013, pp. 725-729.
Author Unknown, Definition of Platform, Merriam-Webster Dictionary, accessed Dec. 10, 2012, 3 pages, http://www.merriam-webster.com/dictionary/platform.
Author Unknown, Definition of On, Merriam-Webster Dictionary, accessed Dec. 14, 2012, 5 pages, http://www.merriam-webster.com/dictionary/on.
Author Unknown, Definition of Platform, Macmillan Dictionary, accessed Dec. 10, 2012, 2 pages, http://www.macmillandictionary.com/dictionary/british/platform.
Author Unknown, "New Breakthrough Treatment for Evaporative Dry Eye Disease Introduced by Dry Eye Specialist, Mark R. Mandel, M.D.," PR Newswire, Dec. 11, 2012, 2 pages, Hayward, California.
Cuevas, Miguel et al., "Correlations Among Symptoms, Signs, and Clinical Tests in Evaporative-Type Dry Eye Disease Caused by Meibomian Gland Dysfunction (MGD)," Current Eye Research, vol. 37, No. 10, Oct. 2012, pp. 855-863.
Greiner, J., "Long-term 12-month improvement in meibomian gland function and reduced dry eye symptoms with a single thermal pulsation treatment," Clinical and Experimental Ophthalmology, vol. 41, No. 6, Aug. 2013, pp. 524-530.
Her, Y. et al., "Dry eye and tear film functions in patients with psoriasis," Japanese Journal of Ophthalmology, vol. 57, No. 4, Jul. 2013, pp. 341-346.
Khandelwal, et al., "Androgen regulation of gene expression in human meibomian gland and conjunctival epithelial cells," Molecular Vision, vol. 18, Apr. 27, 2012, pp. 1055-1067.
Zhang et al., "Efficacy of physical therapy meibomian gland dysfunction," International Eye Science, International Journal of Ophthalmology, vol. 13, No. 6, Jun. 2013, pp. 1267-1268.
Li, Li-Hu et al., "Analysis of the efficacy in the treatment of meibomian gland dysfunction," International Eye Science, vol. 13, No. 7, Jul. 2013, pp. 1495-1497.
Lin, Hui et al., "Dry eye disease: A review of diagnostic approaches and treatments," Saudi Journal of Ophthalmology, vol. 28, Issue 3, Jul.-Sep. 2014, Saudi Ophthalmological Society, pp. 173-181.
Liu, Ze-Yuan et al., "Treatment of dry eye caused by meibomian gland dysfunction," International Eye Science, vol. 14, No. 2, Feb. 2014, pp. 270-272.
Lu, Hui et al., "Tear film measurement by optical reflectometry technique," Journal of Biomedical Optics, vol. 19, No. 2, Feb. 2014, 8 pages.
Ozer, P.A. et al., "Eyelid nodule in a child: a chalazion or idiopathic facial aseptic granuloma?" Eye, vol. 28, No. 9, Sep. 2014, The Royal College of Ophthalmologists, pp. 1146-1147.
Pucker, A. et al., "Analysis of Meibum and Tear Lipids," The Ocular Surface, vol. 10, No. 4, Oct. 2012, pp. 230-250.
Purslow, Christine, "Evaluation of the ocular tolerance of a novel eyelid-warming device used for meibomian gland dysfunction," Contact Lens & Anterior Eye, vol. 36, No. 5, Elsevier Ltd., Oct. 2013, pp. 226-231.
Suzuki, Tomo, "Meibomitis-Related Keratoconjunctivitis: Implications and Clinical Significance of Meibomian Gland Inflammation," Cornea, vol. 31, Supplemental Issue, Nov. 2012, pp. S41-S44.
Tang, Qin et al., "Clinical analysis of meibomian gland dysfunction in elderly patients," International Eye Science, vol. 13, No. 7, Jul. 2013, pp. 1419-1423.
Foulks, Gary N. "The Correlation Between the Tear Film Lipid Layer and Dry Eye Disease," Survey of Ophthalmology, vol. 52, Issue 4, Jul.-Aug. 2007, Elsevier Inc., pp. 369-374.
Baumann, A. et al., "Meibomian gland dysfunction: A comparative study of modern treatments," French Journal of Ophthalmology, vol. 37, No. 4, Apr. 2014, Elsevier Masson SAS, pp. 303-312.
Bron, Anthony J. et al., "Rethinking Dry Eye Disease: A Perspective on Clinical Implications," The Ocular Surface, vol. 12, No. 2S, Apr. 2014, Elsevier Inc., 31 pages.
Zhang, J. et al., "A Meibomian Gland Massage Mechanism for Upper and Lower Eyelids Based on Anti-phase Rolling and Enveloping Movement," Chinese Journal of Medical Instrumentation, vol. 38, No. 4, Jul. 2014, pp. 255-258, 273.
Sullivan, Benjamin D., et al., "Impact of Antiandrogen Treatment on the Fatty Acid Profile of Neutral Lipids in Human Meibomian Gland Secretions," The Journal of Clinical Endocrinology & Metabolism, vol. 85, No. 12, Dec. 2000, The Endocrine Society, pp. 4866-4873.
Sullivan, David A., et al., "Do sex steroids exert sex-specific and/or opposite effects on gene expression in lacrimal and meibomian glands?" Molecular Vision, vol. 15, Aug. 10, 2009, pp. 1553-1572.
Suzuki, Tomo et al., "Estrogen and Progesterone Control of Gene Expression in the Mouse Meibomian Gland," Investigative Ophthalmology & Visual Science, vol. 49, Issue 5, May 2008, Association for Research in Vision and Ophthalmology, pp. 1797-1808.
Finis, D. et al., "Meibom-Drusen-Dysfunktion," Klinische Monatsblatter fur Augenheilkunde, vol. 229, No. 5, Mar. 2012, pp. 506-513 (Abstract translated only).
Korb, et al., "Forceful Meibomian Gland Expression with a Standardized Force of 8 PSI in Patients with Obstructive Meibomian

(56) References Cited

OTHER PUBLICATIONS

Gland Dysfunction," ARVO Annual Meeting, Poster Session, Program No. 3819, Poster Board No. D952, May 3, 2011, 2 pages (Abstract Only).

Korb, et al., "Prevalence of lid wiper epitheliopathy in subjects with dry eye signs and symptoms," Cornea, vol. 29, No. 4, Apr. 2012, pp. 377-383.

Yoshitomi, et al., "Meibomian Gland Compressor and Cataract Surgery," New Ophthalmology, Japan, 2001, vol. 18, No. 3, pp. 321-323.

Willis, et al., "Meibomian gland function, lid wiper epitheliopathy, and dry eye symptoms," ARVO Annual Meeting, May 2011, pp. 3740 (Abstract only).

Foulks, G. et al., Comparative Effectiveness of Azithromycin and Doxycycline in Therapy of Meibomian Gland Dysfunction, ARVO Annual Meeting, May 2011, pp. 3816 (Abstract only).

Korb, et al., "Restoration of meibomian gland function post Lipiflow treatment," ARVO Annual Meeting, May 2011, pp. 3818 (Abstract only).

Maskin, S. et al., "Intraductal Meibomian Gland Probing with Adjunctive Intraductal Microtube Steriod Injection (MGPs) for Meibomian Gland Dysfuction," ARVO Annual Meeting, May 2011, pp. 1145-1152 (Abstract only).

McCann, L. et al., "Effect of First Line Management Therapies on Dry Eye Disease," ARVO Annual Meeting, May 2011, pp. 3829 (Abstract only).

\* cited by examiner

THE NUMBER OF EYELIDS IN EACH CATEGORY IS EXPRESSED AS A PERCENTAGE

|  | ≥75% of the line was posterior to the orifices | ≥75% of the line was touching the orifices | ≥75% of the line was bisecting the orifices | ≥75% of the line was anterior to the orifices | ≥75% of the line was mixed in its position |
|---|---|---|---|---|---|
| Temporal | 30% | 0 | 0 | 0 | 70% |
| Central | 70% | 0 | 0 | 0 | 30% |
| Nasal | 90% | 0 | 0 | 0 | 10% |

*FIG. 7*

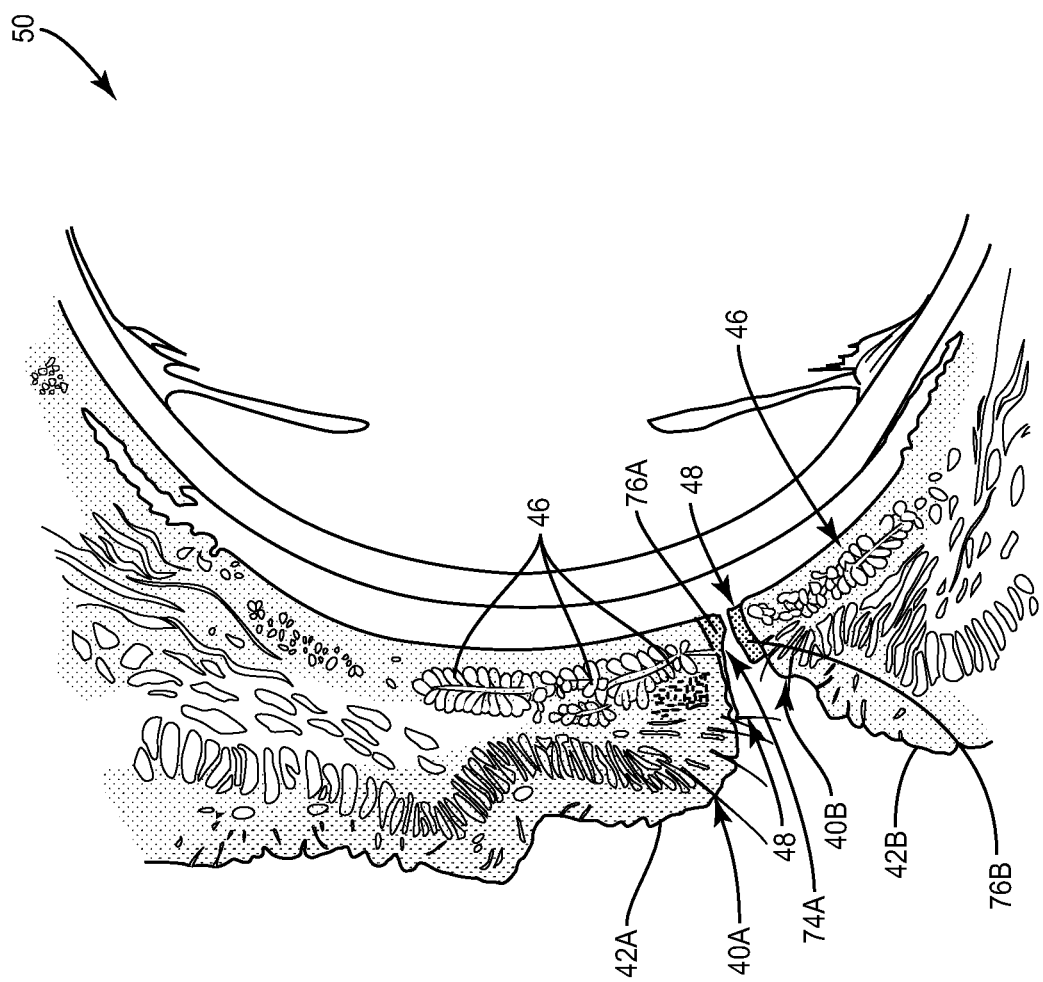

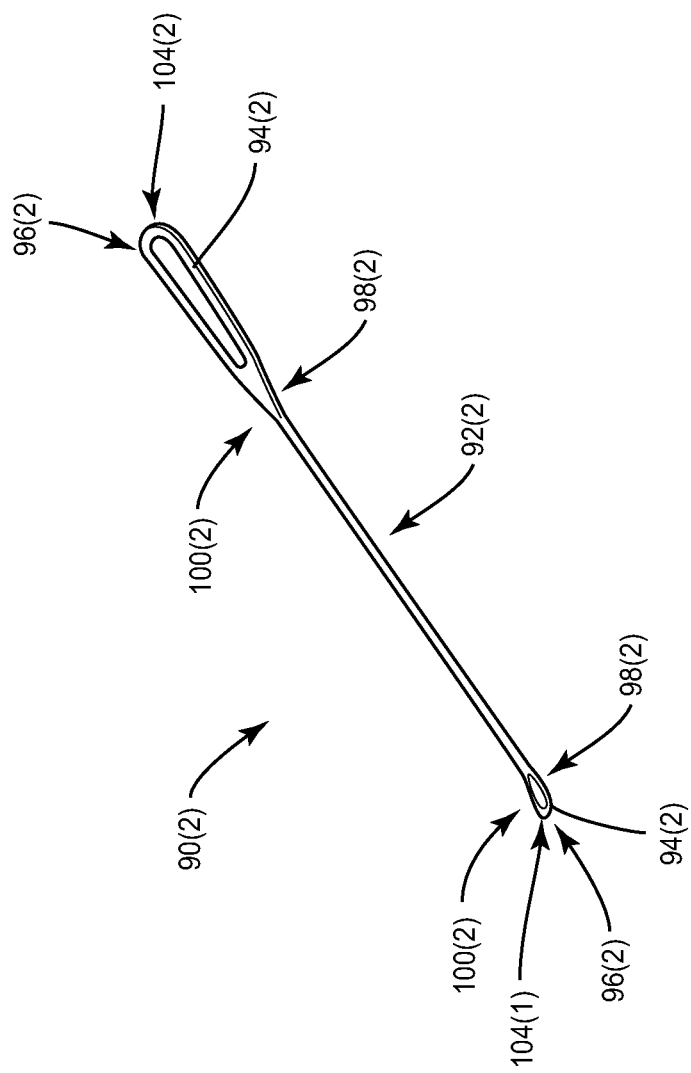

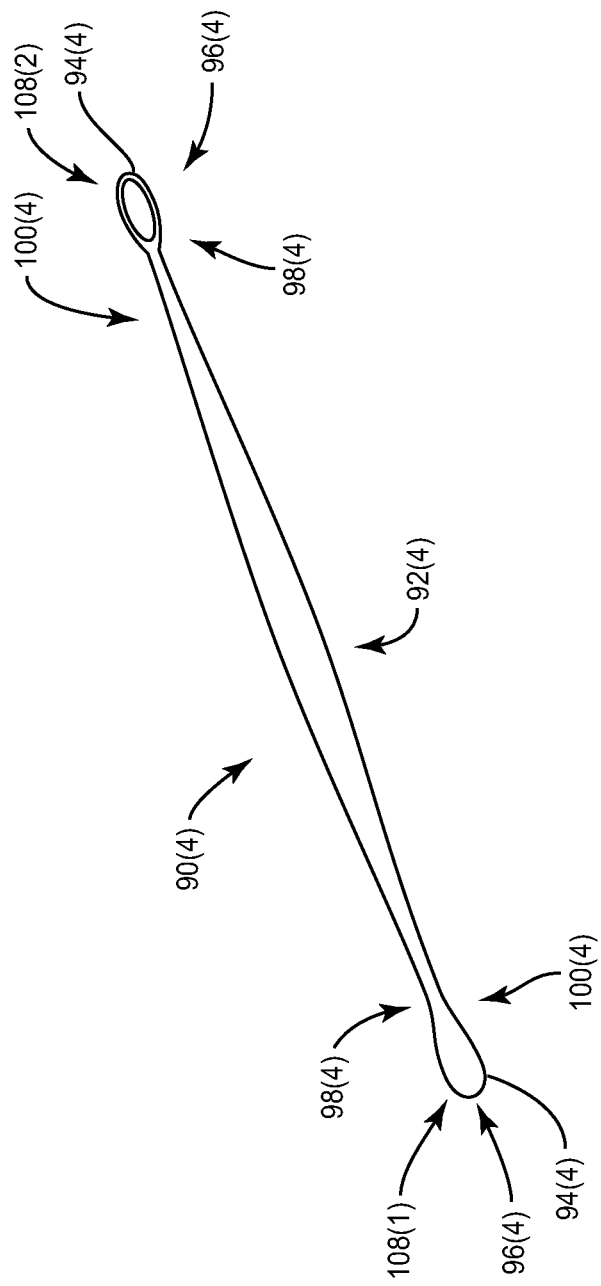

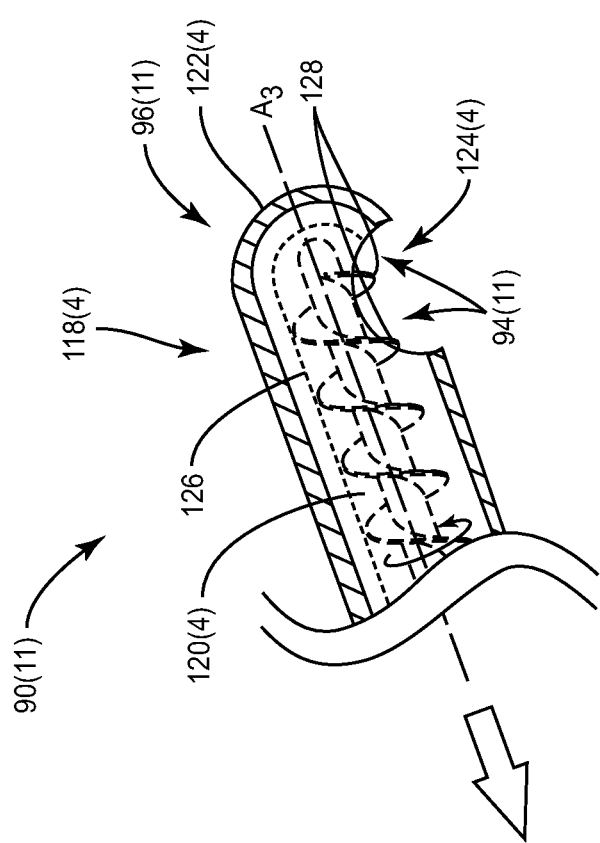

APPARATUSES AND METHODS FOR DIAGNOSING AND/OR TREATING LIPID TRANSPORT DEFICIENCY IN OCULAR TEAR FILMS, AND RELATED COMPONENTS AND DEVICES

PRIORITY APPLICATION

The present application claims priority to International Patent Application No. PCT/US 13/56199 filed on Aug. 22, 2013 and entitled "Apparatuses and Methods for Diagnosing and/or Treating Lipid Transport Deficiency in Ocular Tear Films, and Related Components and Devices," which claims priority to U.S. Provisional Patent Application Ser. No. 61/691,948 filed Aug. 22, 2012, both of which are incorporated herein by reference in their entireties.

RELATED APPLICATIONS

The present application is related to U.S. patent application Ser. No. 13/271,768 filed on Oct. 12, 2011 and entitled "Methods for Diagnosing Meibomian Gland Dysfunction," which is incorporated herein by reference in its entirety.

The present application is also related to U.S. Pat. No. 7,981,146 filed on Jan. 17, 2008 and entitled "Inner Eyelid Treatment for Treating Meibomian Gland Dysfunction," which is incorporated herein by reference in its entirety.

The present application is also related to Patent Application No. PCT/US 12/44650 filed on Jun. 28, 2012 and entitled "Methods and Systems for Treating Meibomian Gland Dysfunction Using Radio-Frequency Energy," which is incorporated herein by reference in its entirety.

BACKGROUND

Field of the Disclosure

The technology of the disclosure relates to apparatuses and methods for diagnosing and/or treating lipid transport deficiency in ocular tear films, and related components and devices.

Technical Background

In the human eye, the precorneal tear film covering ocular surfaces is composed of three primary layers: the mucin layer, the aqueous layer, and the lipid layer. Each layer plays a role in the protection and lubrication of the eye and thus affects dryness of the eye or lack thereof. Dryness of the eye is a recognized ocular disease, which is generally referred to as "dry eye," "dry eye syndrome" (DES), or "keratoconjunctivitis sicca" (KCS). Dry eye can cause symptoms, such as itchiness, burning, and irritation, which can result in discomfort. There is a correlation between the ocular tear film layer thicknesses and dry eye disease. The various medical conditions and damage to the eye as well as the relationship of the aqueous and lipid layers to those conditions are reviewed in Surv Opthalmol 52:369-374, 2007 and additionally briefly discussed below.

As illustrated in FIG. 1, the precorneal tear film includes an innermost layer of the tear film in contact with a cornea 10 of an eye 12 known as the mucus layer 14. The mucus layer 14 is comprised of many mucins. The mucins serve to retain aqueous in the middle layer of the tear film known as the aqueous layer. Thus, the mucus layer 14 is important in that it assists in the retention of aqueous on the cornea 10 to provide a protective layer and lubrication, which prevents dryness of the eye 12.

A middle or aqueous layer 16 comprises the bulk of the tear film. The aqueous layer 16 is formed by secretion of aqueous by lacrimal glands 18 and accessory tear glands 21 surrounding the eye 12, as illustrated in FIG. 2. The aqueous, secreted by the lacrimal glands 18 and accessory tear glands 21, is also commonly referred to as "tears." One function of the aqueous layer 16 is to help flush out any dust, debris, or foreign objects that may get into the eye 12. Another important function of the aqueous layer 16 is to provide a protective layer and lubrication to the eye 12 to keep it moist and comfortable. Defects that cause a lack of sufficient aqueous in the aqueous layer 16, also known as "aqueous deficiency," are a common cause of dry eye. Contact lens wear can also contribute to dry eye. A contact lens can disrupt the natural tear film and can reduce corneal sensitivity over time, which can cause a reduction in tear production.

The outermost layer of the tear film, known as the "lipid layer" 20 and also illustrated in FIG. 1, also aids to prevent dryness of the eye. The lipid layer 20 is comprised of many lipids known as "meibum" or "sebum" that are produced by meibomian glands 22 in upper and lower eyelids 24, 26, as illustrated in FIG. 3. This outermost lipid layer is very thin, typically less than 250 nanometers (nm) in thickness. The lipid layer 20 provides a protective coating over the aqueous layer 16 to limit the rate at which the aqueous layer 16 evaporates. Blinking causes the upper eyelid 24 to mall up aqueous and lipids as a tear film, thus forming a protective coating over the eye 12. A higher rate of evaporation of the aqueous layer 16 can cause dryness of the eye. Thus, if the lipid layer 20 is not sufficient to limit the rate of evaporation of the aqueous layer 16, dryness of the eye may result.

Notwithstanding the foregoing, it has been a longstanding and vexing problem for clinicians and scientists to quantify the lipid and aqueous layers and any deficiencies of same to diagnose evaporative tear loss and/or tear deficiency dry eye conditions. Further, many promising treatments for dry eye have failed to receive approval from the United States Food and Drug Administration due to the inability to demonstrate clinical effectiveness to the satisfaction of the agency. Many clinicians diagnose dry eye based on patient symptoms alone. Questionnaires have been used in this regard. Although it seems reasonable to diagnose dry eye based on symptoms alone, symptoms of ocular discomfort represent only one aspect of "dry eyes," as defined by the National Eye Institute workshop on dry eyes. In the absence of a demonstrable diagnosis of tear deficiency or a possibility of excessive tear evaporation and damage to the exposed surface of the eye, one cannot really satisfy the requirements of dry eye diagnosis.

In addition, the importance of the lipid layer on dry eye syndrome has been well studied (see FIG. 1 for the lipid layer on the cornea of the eye). The creation of normal tear film is a continuous process and the etiology has been well described. With adequate meibomian gland function and proper blinking, proper tear film is maintained. One method of visualizing the duration of tear film is to ask a patient to keep their eyes open and visualizing the tear film through the use of fluorescein strips or other devices. In patients with dry eyes, the tear film is less stable, and breaks up faster and results in a quicker break-up time. Longer durations before tear film break-up indicate healthier tear film and meibomian gland function.

One known method for determining tear break-up time is Fluorescein Break-up Time (FBUT). FBUT is performed with a strip of fluorescein that is applied in the lower eyelid fornix and then quickly removed. The patient will be asked to blink three times and then look into the slit lamp without trying to blink. Using a cobalt-blue filtered light and a slitlamp microscope, a measurement is taken of the amount of time that elapses from the last blink and appearance of the first break in the tear film (a break will be seen by the appearance of a dark spot in the blue field). Typically in clinical practice this is done with a stop watch. FBUT of 10 seconds or less is consistent with dry eyes.

However, there are problems with FBUT. For example, the physical application of the fluorescein filter paper strip to the conjunctiva can stimulate tearing. In addition, the mere presence of fluorescein may change the properties of the tear film. Other methods have been tried to avoid using fluorescein, such as using a keratometer, a keratoscope, or a Tearscope. These methods are termed Non Invasive Breakup Time, or NIBUT. Another technique is to analyze the prerupture phase of the tear film break-up referred to as Tear Thinning Time, or TTT, in which the distortion that occurs on the image of the eye is viewed. However, in all of these methods, the improper use of a stop watch or imperfect methods of detecting tear break up or the prerupture phase of the tear film can result in error. None of these methods provide a quantitative method of determining an amount of time for an area of interest to change on a surface of an eye.

Further, dry eye sufferers are affected in their abilities to perform everyday activities due to the persistent irritation and eye strain that can occur as a result of long periods of computer terminal use. Deficiency in their lipid layer thickness of the eye can be exasperated by partial or incomplete blinking. For example, the number of complete blinks would increase the higher the position of gaze of the individual. So if an individual were looking at a computer which was ten (10) degrees above eye level, they would need more complete blinks than if the computer were at eye level. Similarly if the computer monitor were placed below eye level significantly, there would be the need for fewer blinks because the rate of evaporation from the eye would decrease as the height of the exposed aperture decreases. These factors have been studied and published as work place safety and ergonomic studies have indicated the effect eye strain on productivity and worker satisfaction. Besides eye level position, other qualifiers are a factor, such as the context of the work, local humidity, type of task, age, skin color, etc. of any one individual.

SUMMARY OF THE DETAILED DESCRIPTION

Embodiments disclosed herein include apparatuses and methods for diagnosing and/or treating lipid transport deficiency in ocular tear films, and related components and devices.

As discussed above, the lipid secreted by the meibomian glands being transported to the ocular tear film is important to prevent or reduce evaporative dry eye. Through substantial and previously unknown research, experiments, and discovery to the knowledge of the inventors, it was discovered that meibomian gland secretions can be physically expressed so that the meibomian gland secretion is disposed on the keratinized area of the lid margin, but the meibomian gland secretion may not be transported to the ocular tear film. It was discovered that meibomian gland secretions may not be transported to the ocular tear film due to irregular surface of devitalized and/or dead cells of increased height formed at the Line of Marx and/or behind the Line of Marx of the eyelid. The Line of Marx is a virtual line at the meeting of the wet tissue area and dry tissue area of the upper and lower eyelids at the lid margin serving to divide the wet tissue areas and dry tissue areas.

Thus, the embodiments disclosed herein involve the diagnosis and removal of the devitalized and/or dead cell material formed in the lid margin to attempt to restore a normal lid margin. In this manner, the devitalized and/or dead cell material are removed or the amount present is reduced or no longer present to prevent, reduce, or affect the transport of lipid secreted by the meibomian glands to the tear film to reduce evaporative dry eye and improve dry eye conditions in patients. The diagnosis and removal of devitalized and/or dead cell material may be performed at desired intervals. Patients who suffer from conditions that block meibomian gland orifices, partial, infrequent, or inhibited blinking resulting in reduced lipid secretions from meibomian glands, and/or blockages in meibomian gland channels reducing secretion of lipids through the meibomian gland orifices may require more frequent diagnosis and treatment to remove devitalized and/or dead cell material.

In one exemplary embodiment, a method for treating lipid transport deficiency in an ocular tear film is disclosed. The method comprises providing at least one mechanical treatment device having at least one sharp edge. The method further comprises moving one of the at least one textured surface and a lid margin of an eyelid proximate to the Line of Marx of the eyelid against the other to exfoliate devitalized and/or dead cell material from the lid margin.

In another exemplary embodiment, an apparatus for treating lipid transport deficiency in ocular tear films is disclosed. The apparatus comprises at least one mechanical treatment device having at least one sharp edge configured to move against a lid margin of a mammalian eyelid proximate to the Line of Marx of the eyelid to exfoliate devitalized and/or dead cell material from the lid margin.

In one exemplary embodiment, a method for treating lipid transport deficiency in an ocular tear film is disclosed. The method comprises providing at least one mechanical treatment device having at least one textured surface. The method further comprises moving one of the at least one textured surface and a lid margin of an eyelid proximate to the Line of Marx of the eyelid against the other to exfoliate devitalized and/or dead cell material from the lid margin.

In another exemplary embodiment, an apparatus for treating lipid transport deficiency in ocular tear films is disclosed. The apparatus comprises at least one mechanical treatment device having at least one textured surface configured to move against a lid margin of a mammalian eyelid proximate to the Line of Marx of the eyelid to exfoliate devitalized and/or dead cell material from the lid margin.

In another exemplary embodiment, a method of treating lipid transport deficiency in ocular tear films. The method comprises applying a force to a patient's eyelid to apply pressure to the patient's eyelid to move a lid margin of the eyelid proximate to the Line of Marx of the eyelid against a textured surface to exfoliate devitalized and/or dead cell material from the lid margin.

In another exemplary embodiment, a system for treating lipid transport deficiency in ocular tear films is disclosed. The system comprises a controller and a force generating device adapted to be positioned on an inner surface of a patient's eyelid. The force generating device applies pressure to the inner surface of the patient's eyelid to move a lid margin of the eyelid proximate to the Line of Marx of the eyelid against a textured surface of the force generating device to exfoliate devitalized and/or dead cell material from the lid margin. The system further comprises a controller interface adapted to couple the controller to the force generating device. The controller is further adapted to control the force generating device to generate a pressure on the inner surface of the patient's eyelid.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

FIG. 7 is a table illustrating the Line of Marx relative to meibomian gland orifices of patients involved in the experiment in FIGS. 6A and 6B;

FIG. 12A illustrates a vertical cross section of the eye including the upper eyelid and the lower eyelid illustrating build up of devitalized and/or dead tissue in the Line of Marx area that can prevent, reduce, or affect lipids secreted from the meibomian glands from being transported to the tear film;

FIG. 12B illustrates a close-up vertical cross section view of the upper eyelid in FIG. 12A, illustrating the build up of devitalized and/or dead tissue on the lid margin in the Line of Marx area that can prevent, reduce, or affect lipids secreted from the meibomian glands from being transported to the tear film;

FIG. 15A is an exemplary angulation surface treatment device configured to remove devitalized and/or dead tissue in the lid margin;

FIG. 15C is an exemplary cup scraper mechanical treatment device configured to remove devitalized and/or dead tissue in the lid margin;

FIGS. 18A-18D illustrate exemplary hollow distal tips that include sharp circular edges sharpened and/or textured mechanical surfaces to remove devitalized and/or dead tissue in the lid margin that can be aspirated through a hollow chamber in the distal tip as part of a mechanical treatment device;

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed herein include apparatuses and methods for diagnosing and/or treating lipid transport deficiency in ocular tear films, and related components and devices. As discussed above, the lipid secreted by the meibomian glands being transported to the ocular tear film is important to prevent or reduce evaporative dry eye. Through substantial and previously unknown research, experiments, and discovery to the knowledge of the inventors, it was discovered that meibomian gland secretions can be physically expressed so that the meibomian gland secretion is disposed on the keratinized area of the lid margin, but the meibomian gland secretion may not be transported to the ocular tear film. It was discovered that meibomian gland secretions may not be transported to the ocular tear film due to an actual wall of devitalized and/or dead cells of increased height formed at the Line of Marx and/or behind the Line of Marx of the eyelid. The Line of Marx is a virtual line at the meeting of the wet tissue area and dry tissue area of the upper and lower eyelids at the lid margin serving to divide the wet tissue areas and dry tissue areas. The Line of Marx is also known as the mucocutaneous junction. Marx made the observation in "Übervitale Färbungen am Auge and an den Lidern"[8] that the tissue behind the Line of Marx—the wet tissue at the lid margin, was higher than the dry tissue in front of the Line of Marx. In other words, the wet tissue at the lid margin was microscopically elevated.

However, the present disclosure discovered something that was not recognized by Marx. The present disclosure discovered that devitalized and/or dead cells formed at the Line of Marx in certain patients may prevent lipid secreted by the meibomian glands from being transported to the ocular tear film thus contributing to evaporative dry eye. Thus, if these devitalized and/or dead cells formed on the lid margin, including at the Line of Marx and on keratinized cells and aberrant mucosal tissue, are removed according to the apparatuses and methods disclosed herein, meibomian gland secretions will not be prevented from being transported to the ocular tear film in certain patients where otherwise, the devitalized and/or dead cells formed at the Line of Marx may be sufficiently built up to prevent or reduce transport of meibomian gland secretions to the ocular tear film.

Figure 13:
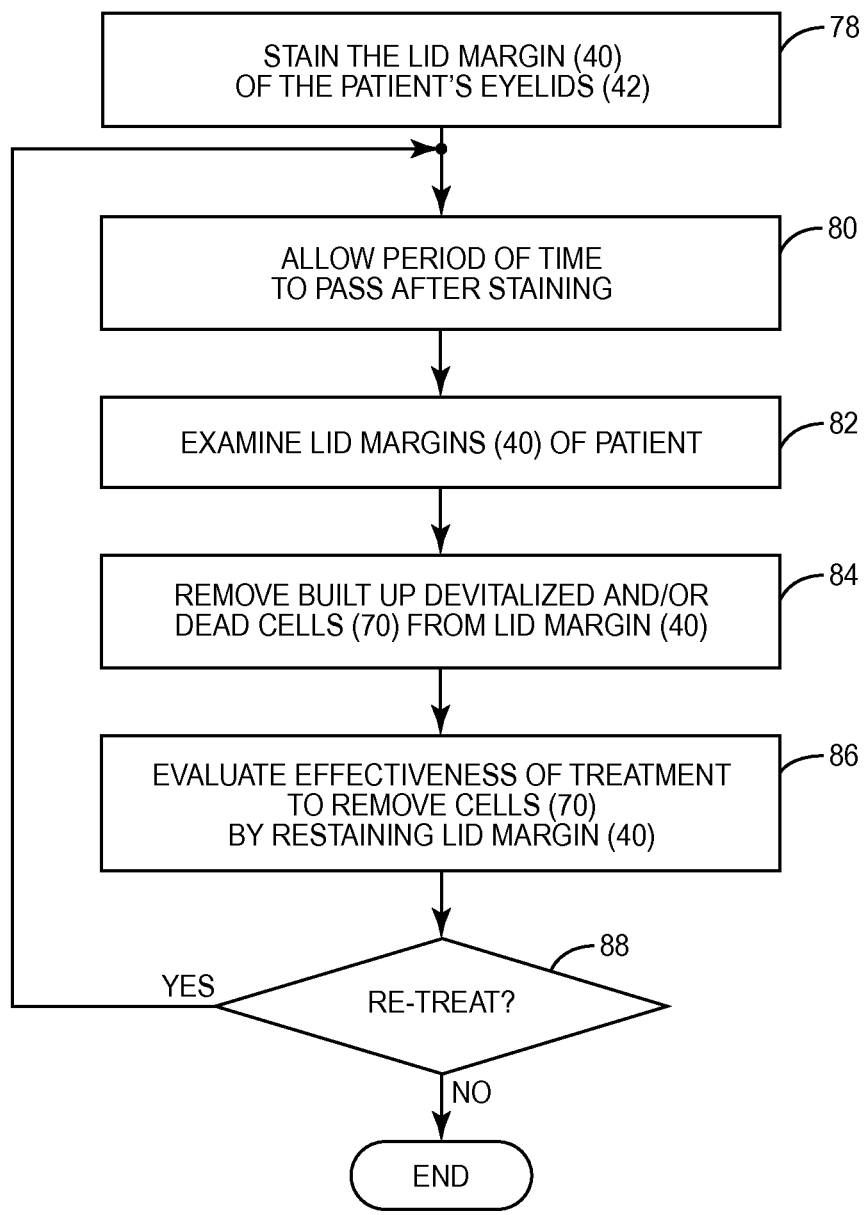
FIG. 13 is a flowchart illustrating an exemplary process of diagnosing of devitalized and/or dead tissue in the lid margin, including in the Line of Marx area, and the treating and evaluating treatment of devitalized and/or dead tissue in the lid margin in the Line of Marx to improve transport of meibomian gland lipid secretion to the tear film to treat evaporative dry eye.

Before discussing the embodiments for diagnosing and/or treating lipid transport deficiency in ocular tear films, and related components and devices starting at FIG. 13 certain experiments and discoveries that led to the recognition that lipid secretions from meibomian glands pass over the Line of Marx before reaching the tear film are first discussed.

Figure 1:
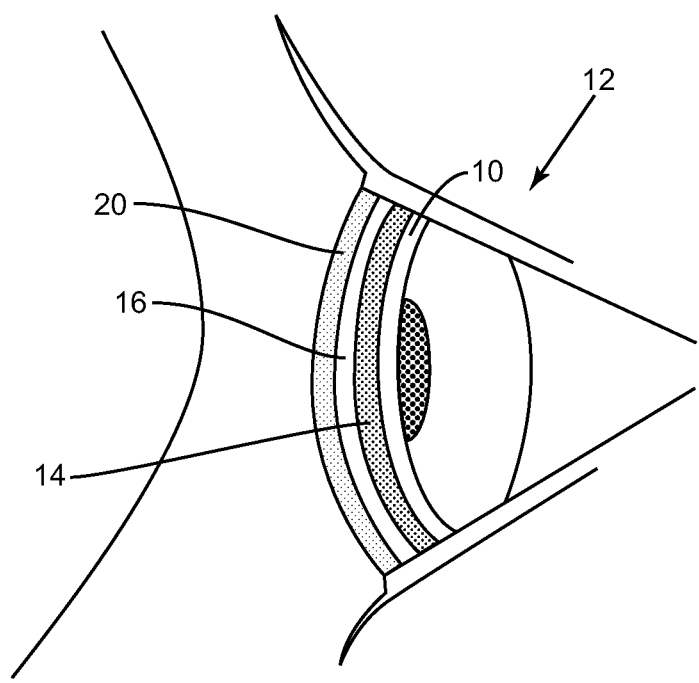
FIG. 1 is a side view of an exemplary eye showing the three layers of the tear film in exaggerated form.
Figure 2:
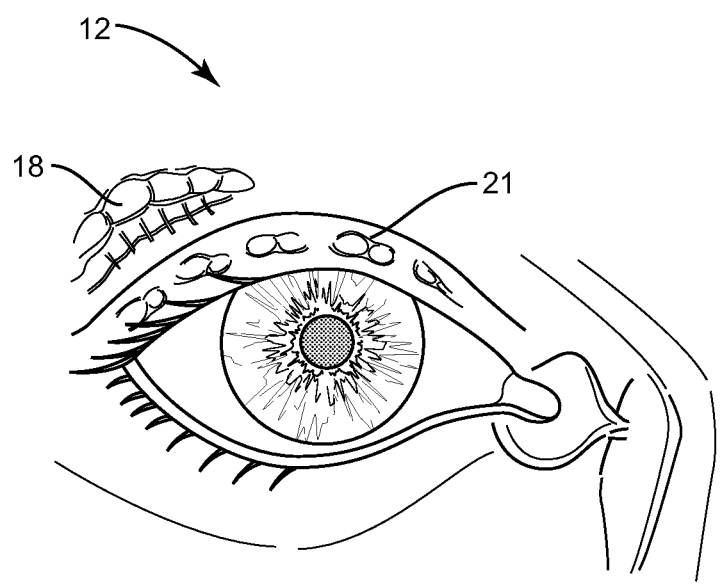
FIG. 2 is a front view of an exemplary eye showing the lacrimal and accessory tear glands that produce aqueous in the eye.
Figure 3:
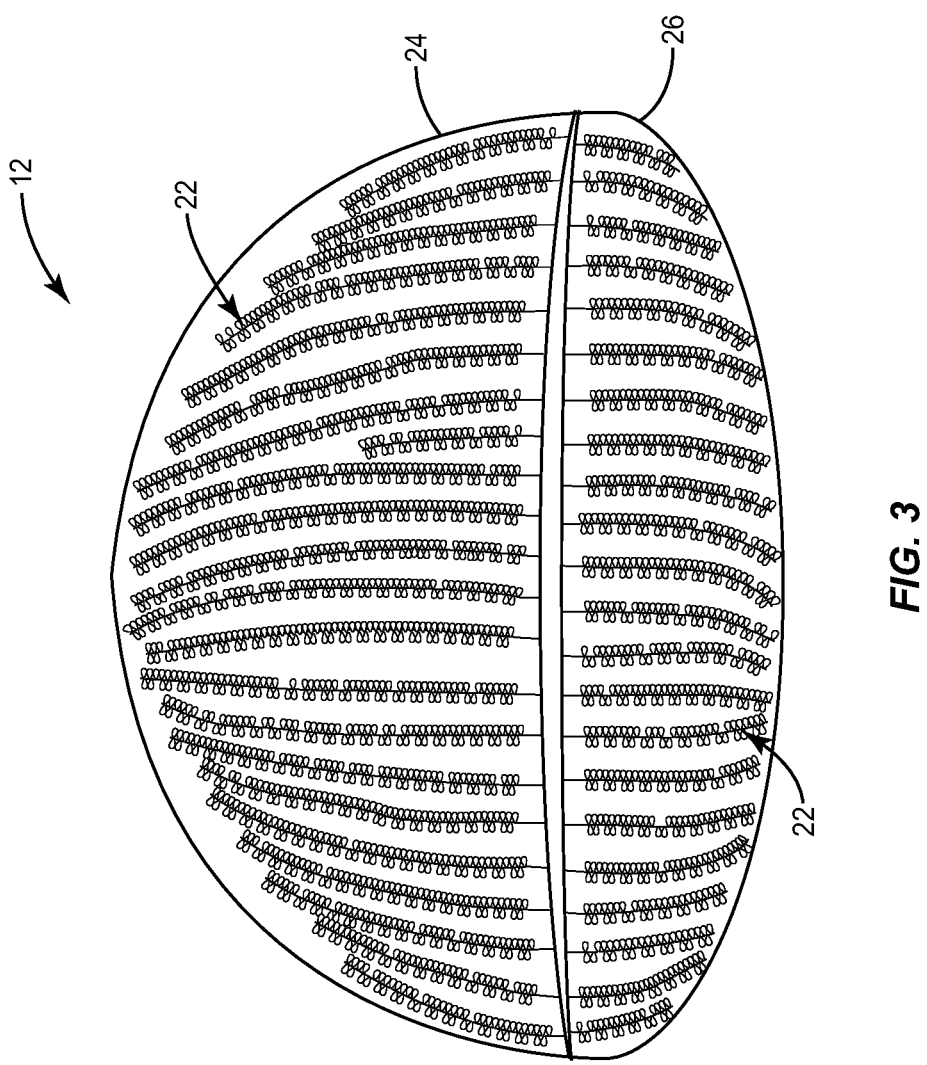
FIG. 3 illustrates exemplary upper and lower eyelids showing the meibomian glands contained therein.
Figure 4:
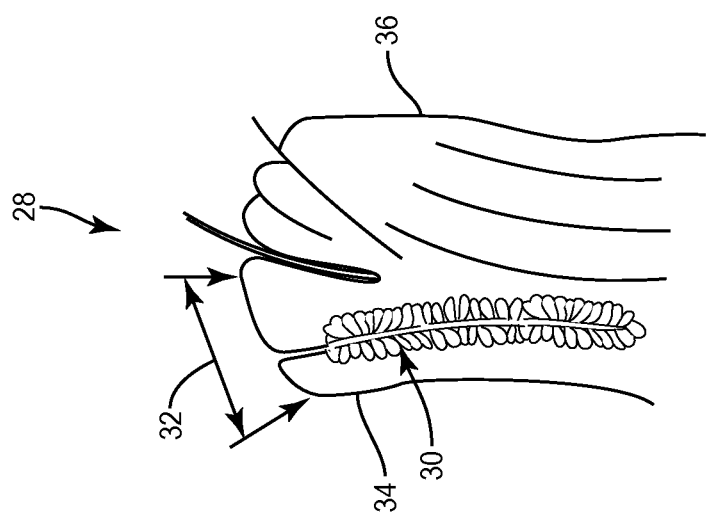
FIG. 4 is a side view of an exemplary eyelid illustrating the meibomian glands and the keratinized area of the eyelid where it was discovered that sebum produced by the meibomian gland is discharged to the keratinized lid margin in the Line of Marx area rather than directly onto the ocular tear film.

With reference to FIG. 1, it has been established that the lipid layer 20 provides a protective coating over the aqueous layer 16 to limit the rate at which the aqueous layer 16 evaporates. A higher rate of evaporation of the aqueous layer 16 can cause dryness of the eye. Thus, if the lipid layer 20 is not sufficient to limit the rate of evaporation of the aqueous layer 16, dryness of the eye may result. Substantial studies were undertaken leading to the present disclosure on exactly how meibomian glands functioned. It was discovered during this research and studies that lipids produced by the meibomian glands are discharged onto the keratinized areas of the upper and lower eyelid margin rather than being discharged directly onto the ocular tear film itself. This is illustrated in a side view of an eyelid 28 in FIG. 4. As illustrated in FIG. 4, it was discovered that the lipid produced by the meibomian glands 30 was discharged onto the keratinized area 32 of the eyelid 28 rather than being discharged directly onto the ocular tear film itself. FIG. 4 illustrates the meibomian glands 30 disposed inside the eyelid 28 between the inner surface of the eyelid 34 and the outer surface of the eyelid 36.

Figure 5:
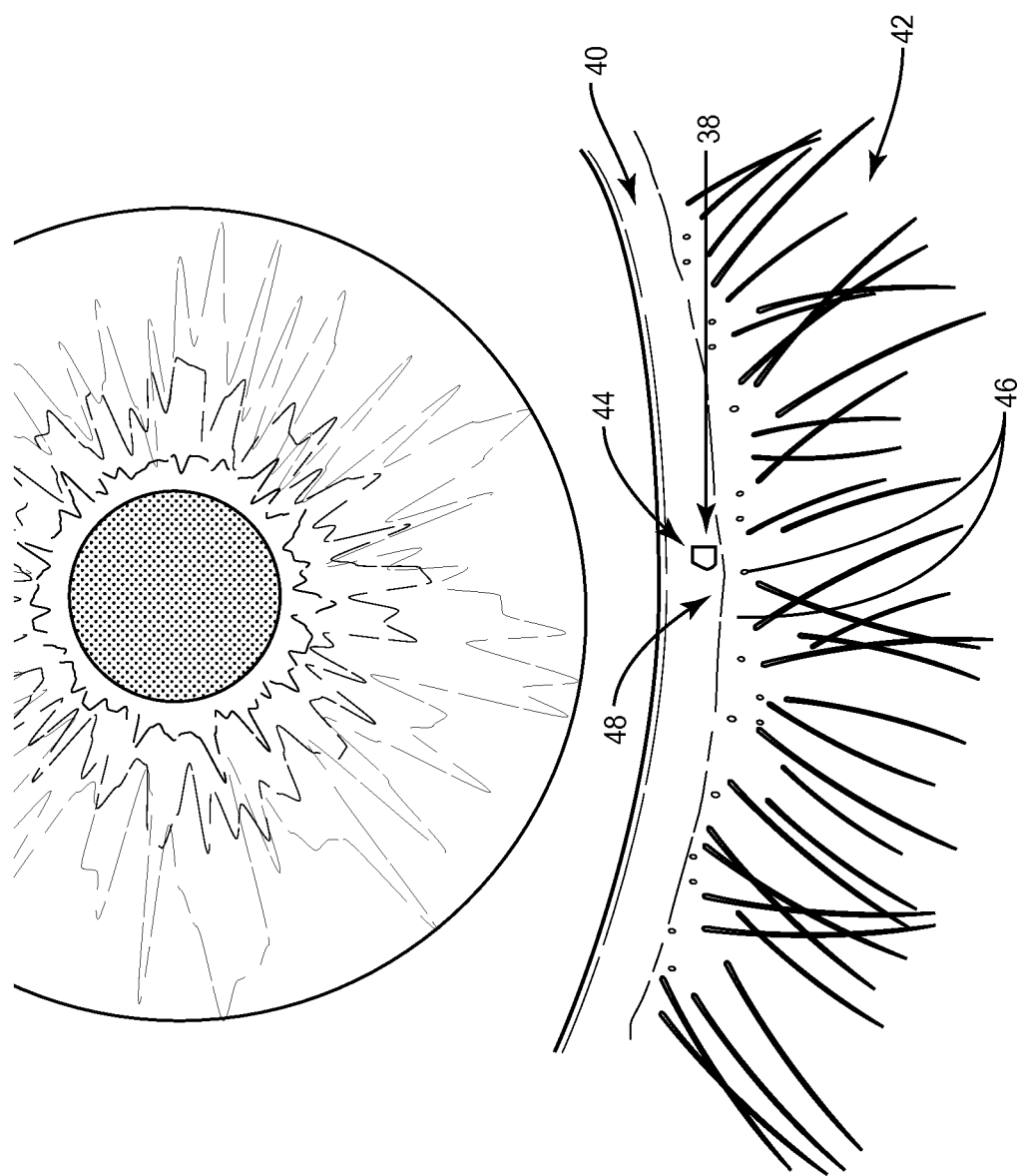
FIG. 5 is a close-up picture of the eye and lower eyelid margin illustrating a 0.1 microliter micro drop of unpreserved 2% liquid fluorescein placed on the keratinized lower eyelid margin to determine if the micro drop was altered during blinking.

Using a custom application device, an approximate 0.1-microliter (100 nm in size) micro drop 38 of unpreserved 2% liquid fluorescein (B&L, Chauvin, France) was placed in the temporal (T) third of the keratinized lower lid margin 40 of the patient's lower eyelid 42, as illustrated in FIG. 5. This technique of placing the micro drop 38 in an area 44 in keratinized lid margin 40 of the lower eyelid 42 allowed study of how the micro drop 38 moved on the lower eyelid 42 with blinking actions.

Figure 6A:
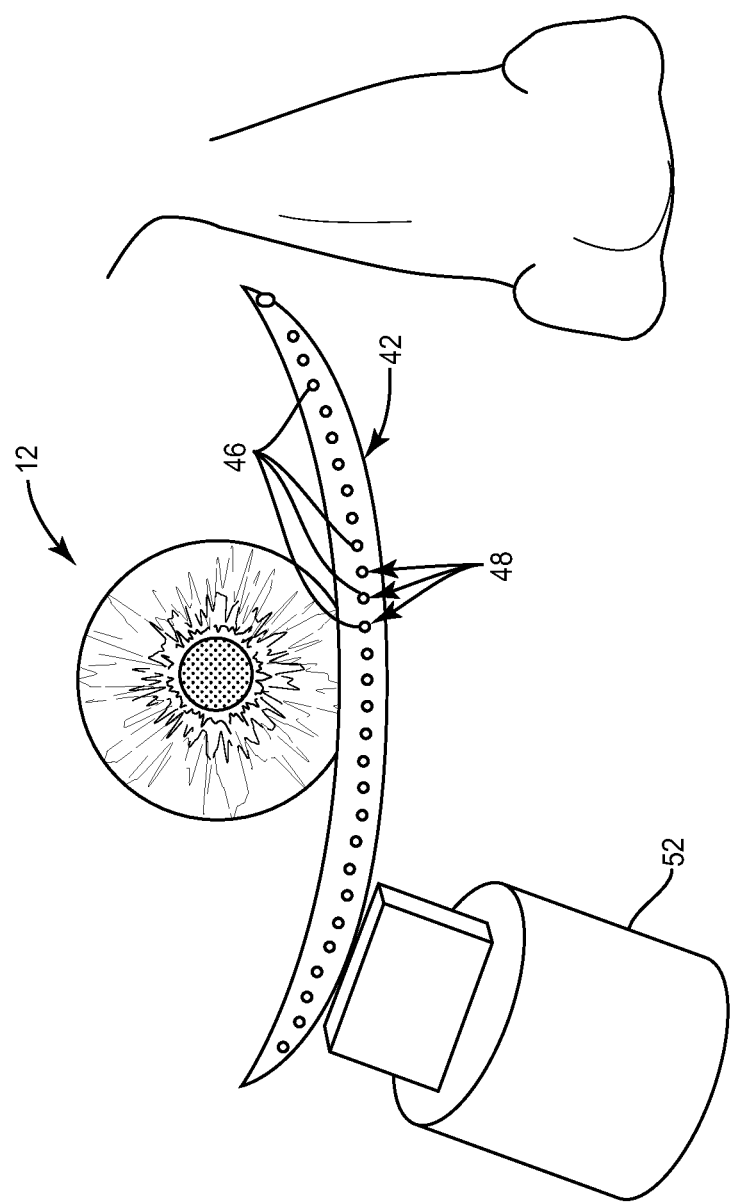
FIGS. 6A and 6B illustrate use of the Meibomian Gland Evaluator™ to assess the meibomian gland expression of the meibomian glands of a patient's lower eyelid during an experiment to determine if keratinized upper and lower lid margins make contact.
Figure 6B:
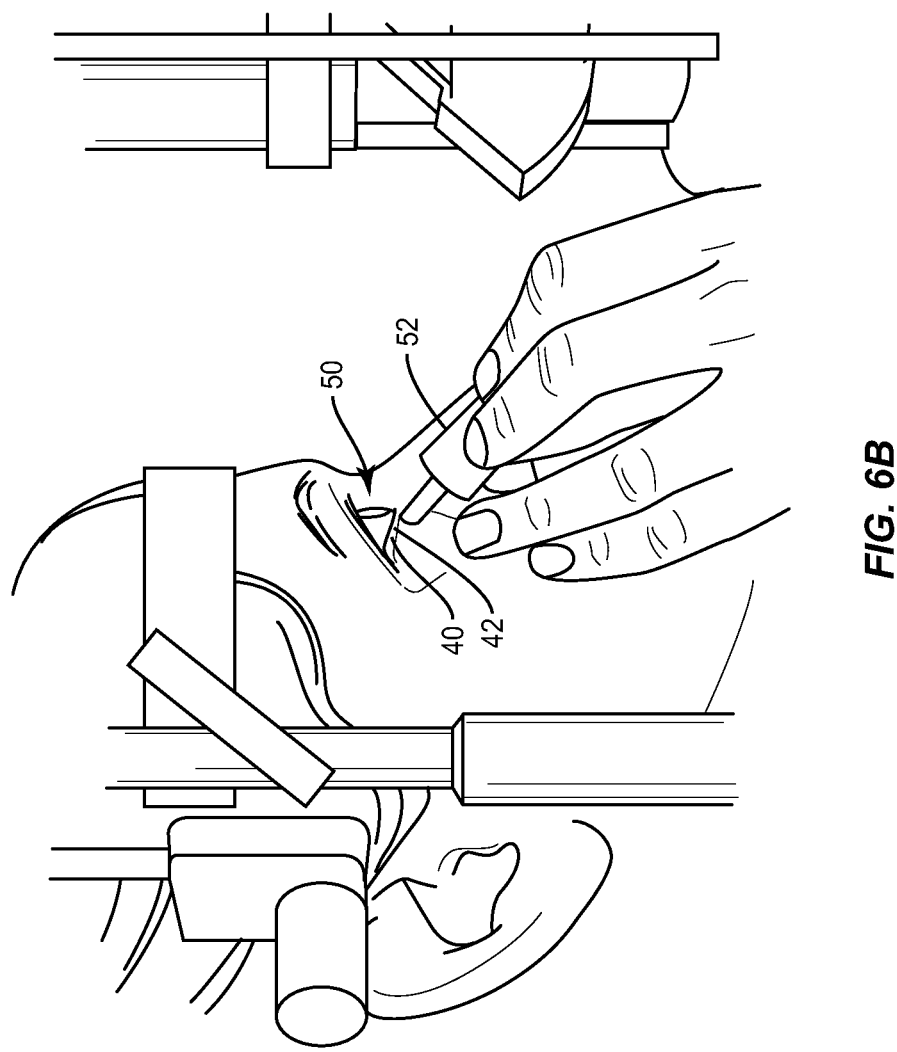

Next, as illustrated in FIGS. 6A and 6B, diagnostic meibomian gland expression was performed along the lower lid margin 40 of the patient's eye 12 to assess MG functionality using a meibomian gland evaluator or Korb MGE™ 52 manufactured by TearScience, Inc.

The position of meibomian gland orifices 48 (shown in FIG. 6A) relative to the Line of Marx is shown in the table 54 in FIG. 7, which also shows the break down by lid position (temporal, central, or nasal). The nasal and central lid regions showed a significantly higher likelihood of the Line of Marx being posterior to the meibomian gland orifices 48 (90% and 70% of the time, respectively) relative to the temporal region (30% of the time).

Figure 8:
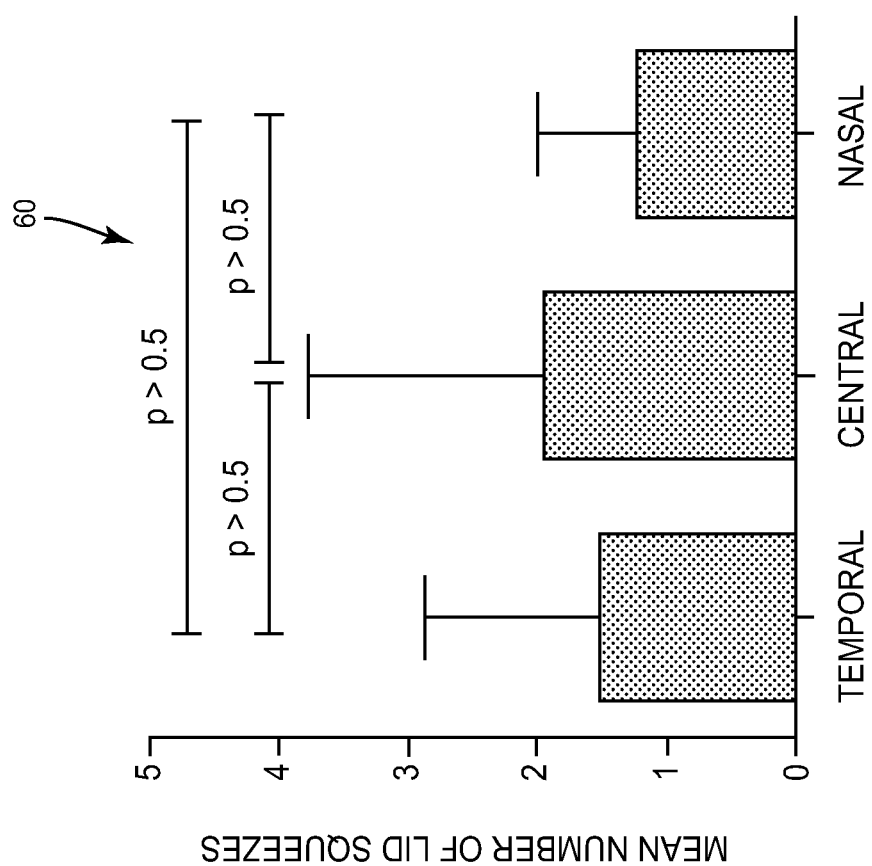
FIG. 8 is a chart illustrating exemplary mean numbers of meibomian glands in a patient's eyelid yielding liquid secretion in each segment of the lower eyelid.

The mean numbers of meibomian glands 46 yielding liquid secretion (MGYLS) in each segment of the lower eyelid 42 is illustrated in the graph 60 in FIG. 8. There were significantly fewer MGYLS in the temporal region compared with the central ($p<0.005$) and the nasal region ($p<0.0005$). The mean total number of MGYLS across all lower eyelids 42 was 9.5±4.1.

Figure 9:
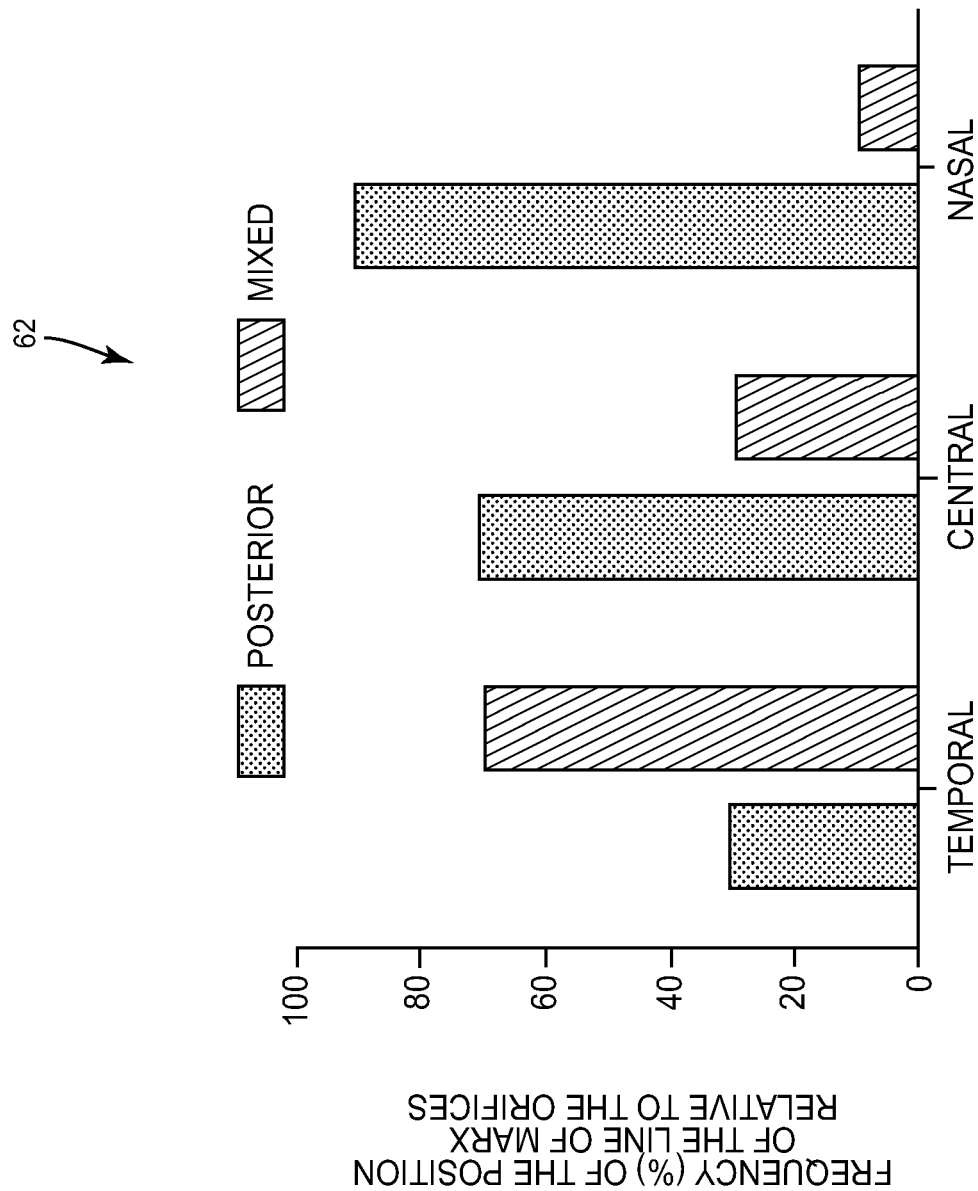
FIG. 9 is a chart illustrating exemplary frequency (in percentage) of the position of the Line of Marx in a patient's lower eyelid relative to the number of meibomian gland orifices.

FIG. 9 is a chart 62 illustrating frequency in percentage of the position of the Line of Marx in a patient's lower eyelid 42 relative to the number of meibomian gland orifices 48. As illustrated in the chart 62, the temporal region showed a significantly higher likelihood of the Line of Marx undulating (touching, bisecting the meibomian gland orifices 48, or even moving anterior to the meibomian gland orifices 48). Other experiments involved placing micro drops of lissamine green and rose bengal, or preferably using fluorescein for the devitalized cells or traumatized cells and rose bengal or lissamine green for the deceased cells.

This blinking experiment established that the area of the keratinized lid margin 40 of the lower eyelid 42 where the micro drop 38 was placed does not normally touch the opposing eyelid during normal blinking. It was surprising to reliably and repeatedly show that the micro drop 38 placed in the area 44 of the keratinized lid margin 40 of the lower eyelid 42 appeared to be unaltered by ten (10) consecutive deliberate blinks in all subjects. What was discovered is that the micro drop 38 did not move until the patient was requested to squeeze his/her eyelids relatively forcefully.

As a result of this blinking experiment, it was further discovered that there is a space between the keratinized lid margins 40 when the lower eyelid 42 shuts in the act of complete blinking. This space must have a vertical dimension adequate to accommodate the 100 nm micro drop 38. Thus, it was further discovered that if only minute amounts of lipid (e.g., 100 nm or less) were only secreted by the meibomian glands 46 through the meibomian gland orifices 48 by normal blinking, squeezing, or other pressure as a result of a dysfunction of meibomian gland 46, these minute amounts of lipid would not spread (i.e., be transported) to the patient's tear film through normal blinking action. Thus, the lipid secretion from the meibomian glands 46 delivered through the meibomian gland orifices 48 to the keratinized lid margin 40 would not absorb the lipid through the keratin. Rather, the surface of the keratinized lid margin 40 would hinder the spread or act as a barrier to the dispersion of the lipid. The lipid secreted by the meibomian glands 46 would lay in the keratinized lid margin 40 in a film with a portion being transferred to the ocular tear film. As discussed above, the lipid being transported to the ocular tear film is important to prevent or reduce evaporative dry eye.

Figure 10:
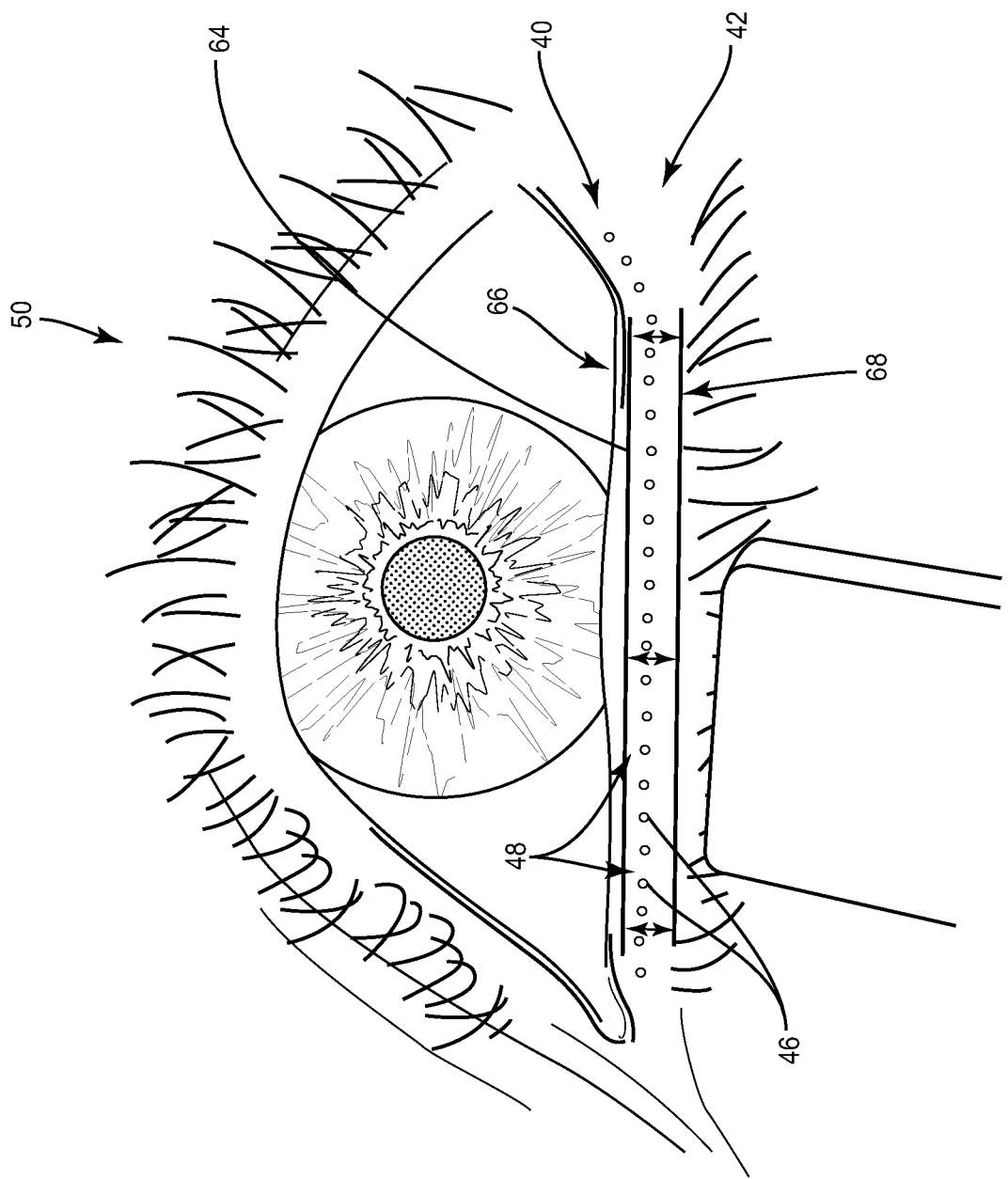
FIG. 10 illustrates the Line of Marx virtual line at the meeting of the wet tissue area and dry tissue area of a lower eyelid, serving to divide the wet tissue area and the dry tissue area.
Figure 11:
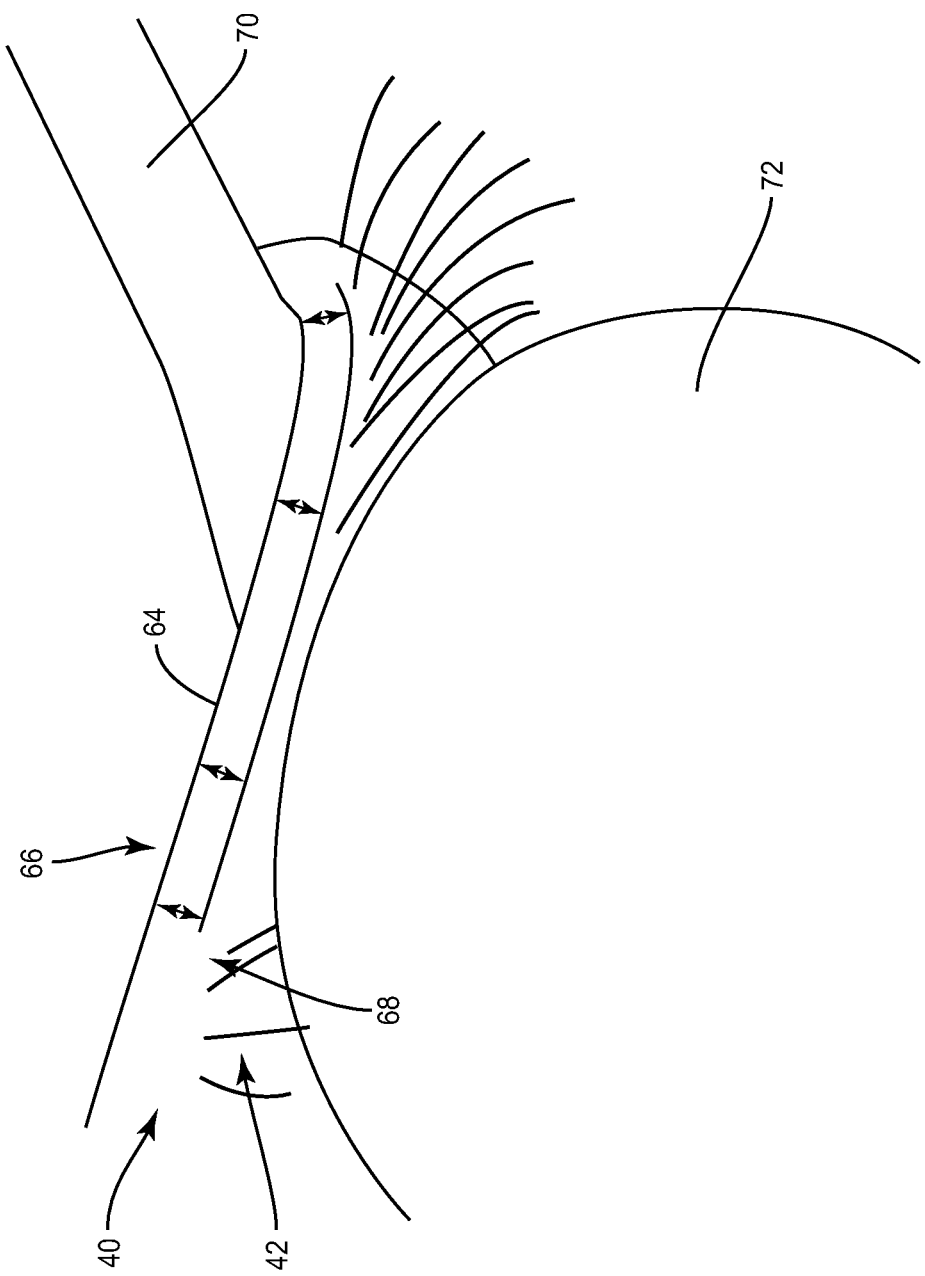
FIG. 11 is another illustration of the Line of Marx in the lower eyelid of FIG. 10 with a tip disposed behind the lower eyelid and thumb.

Further research was performed to try to determine why lipid would lay in the keratinized lid margin 40 in a film without being transported to the ocular tear film for certain patients. It was further discovered that if the meibomian gland 46 secretion is secreted onto the keratinized tissue, it must pass over the Line of Marx onto the tear film and into the inferior meniscus. As illustrated in FIG. 10, the Line of Marx 64 is a virtual line at the meeting of the wet tissue area 66 and dry tissue area 68 of the upper and lower eyelids 42 (lower eyelid 42 shown in FIG. 10) at the keratinized lid margin 40, serving to divide the wet tissue areas 66 and dry tissue areas 68. FIG. 11 illustrates the Line of Marx 64 with a tip 70 disposed behind the lower eyelid 42 and thumb 72. The Line of Marx is also known as the mucocutaneous junction. Marx made the observation that the tissue behind the Line of Marx—the wet tissue 66 at the keratinized lid margin 40, was higher than the dry tissue 68 in front of the Line of Marx 64. In other words, the wet tissue 66 at lid margin 40 was microscopically elevated due to build up of devitalized and/or dead cells that form and build up at the mucocutaneous junction at the lid margin 40.

To further illustrate the elevated wet tissue 66 due to build up of devitalized and/or dead tissue cells on the keratinized lid margin 40, FIG. 12A is provided. FIG. 12A illustrates a vertical cross section of the eye 50 including the upper eyelid 42A and the lower eyelid 42B. FIG. 12B illustrates a close-up vertical cross section view of the upper eyelid 42A in FIG. 12A. As illustrated in FIG. 12A, devitalized and/or dead tissue cells 76A, 76B have built up on the keratinized lid margins 40A, 40B. This built up devitalized and/or dead tissue cells 76A on the keratinized lid margin 40A of the upper eyelid 42A in the Line of Marx 64A is illustrated in close-up view in FIG. 12B. Note that the devitalized and/or dead tissue cells 76A are built up higher on the wet tissue 66A side of the keratinized lid margin 40A at a tissue shoulder 74A than on the dry tissue 68A side of the keratinized lid margin 40A in the Line of Marx 64A. Thus, lipid secreted from the meibomian glands 46A through the meibomian gland orifices 48A have to pass over the devitalized and/or dead tissue cells 76A and over the tissue shoulder 74A to reach the tear film. If a patient's meibomian glands 46 do not provide sufficient lipid to pass over the tissue shoulder 74A of the devitalized and/or dead tissue cells 76A, the lipid may not reach the patients tear film, thus contributing to evaporative dry eye. The cell structure of the devitalized and/or dead tissue cells 76A may require use of over four hundred (400) to five hundred (500) magnification, and even up to one thousand (1000) magnification to be observed. The devitalized and/or dead tissue cells 76A contributes to evaporative dry eye independent of the function or dysfunction of the meibomian glands 46, regardless of whether such dysfunction is the result of occlusions in the meibomian gland 46 channel or meibomian gland orifice 48, or both.

The Line of Marx 64 was found to be approximately 0.1 mm wide with healthy young individuals, and increases in width with older individuals. There can be a number of reasons why the devitalized and/or dead cells 76 form and build up at the mucocutaneous junction (Line of Marx) at the eyelid margin 40. It is theorized that most people are partial blinkers, a condition aggravated by computer use and other activities that inhibit blinking, and the lid margins simply do not get wiped. Also, dry eye states may inhibit blinking or result in partial blinking, since the blinking actions without adequate lubrication may cause sensation resulting in inhibition of blinking. When the lid margins 40 do not get wiped and cleaned adequately by blinking action, material accumulates. This material that accumulates on the lid margins 40 may be only dead cells which are moved from the wet tissue 66 areas and the dry tissue areas 68 of the lid margin 40 to the area of the Line of Marx 64 by flow patterns or other mechanisms.

As the process continues, the devitalized and/or dead cells 76 are not removed, and as a result they accumulate and form on both the lower and upper lid margins 40A, 40B, including at the Line of Marx 64A, 64B and on keratinized cells and aberrant mucosal tissue, and to a greater degree on the lower lid margin 40B. The result is multifactorial. The more irregular the lid margins 40 from all of this devitalized material 76, the more difficult it is for the transfer of the meibomian gland 46 secretion to occur from the keratinized area of the lid margin 40 or from those meibomian gland orifices 48 which might be now entrapped within the wet squalors epithelium of the palpebral conjunctiva which advanced on the lid margin 40 from posterior to the meibomian gland orifices 48 to anterior to the meibomian gland orifices 48. The actual anatomical irregularities and deformation of the surface of the lid margin 40 from the latter phenomena would inhibit the transfer of meibomian gland 46 secretion from the lid margin 40, where it is secreted via the meibomian gland orifices 48 to the tear film. Another factor is the encroachment of this material over the meibomian gland orifices 48, effectively blocking the meibomian gland orifices 48.

Thus in summary, there are several factors to alter and inhibit the transfer of meibomian gland 46 secretion from the lid margin 40 to the tear film. First, the deformation of the lid margins 40 may alter the relationship of the upper and lower lids 42A, 42B during blinking, thus altering the movement of the meibomian lipid secretion from the keratinized lid margin 40 to the tear film. Second, the increased material 76 literally acts as a wall and barrier on the lid margin 40 to prevent the secretion from moving in to the tear film or being moved to the upper lid 42A for delivery to the tear film. Conducted experiments have proven that the secretions of the meibomian glands 46 can be physically expressed so that there is meibomian gland 46 secretion on the keratinized area of the lid margins 40, but it will not be transferred to the tear film because of an actual wall formed by the increased height at the Line of Marx 64 and also the increased height of the material behind the Line of Marx 64. Third, the devitalized material 76 in the area of the meibomian gland orifices 48 and/or directly over the meibomian gland orifices 48 obstructs the meibomian glands 46, thereby preventing secretion from exiting the meibomian gland 46. This may be distinguished from the growth of keratinized epithelium over the meibomian gland orifices 48, which is not related to the abnormal devitalized accumulation of material 76, although both of these processes can exist simultaneously.

Thus, the embodiments disclosed herein involve the diagnosis and removal of the devitalized and/or dead cell material 76 formed in the lid margin 40 to attempt to restore a normal lid margin 40. In this manner, the devitalized and/or dead cell material 76 will not prevent or reduce the transport of lipid secreted by the meibomian glands 46 to the tear film. Evaporative dry eye conditions in patients may improve as a result. The diagnosis and removal of devitalized and/or dead cell material 76 may be performed at desired intervals, for example every six (6) months. Patients who suffer from conditions that block meibomian gland orifices, partial, infrequent, or inhibited blinking resulting in reduced lipid secretions from meibomian glands 46, and/or blockages in meibomian gland channels reducing secretion of lipids through the meibomian gland orifices 48 may require more frequent diagnosis and treatment to remove devitalized and/or dead cell material 76.

Before performing procedures to remove the devitalized and/or dead cells 76 from the lid margin 40 of a patient, the patient may first be diagnosed for the presence of the devitalized and/or dead cells 76. It may be desired to determine if lipids secreted from the meibomian glands 46 through the meibomian gland orifices 48 are passing over the devitalized and/or dead cells 76 present in the Line of Marx 64 area of the lid margins 40 and being transported to the tear film.

In this regard, in order to understand the areas of the lid margin 40 most affected, staining procedures can be utilized to identify devitalized and/or dead cells 76 in the lid margin 40. As a non-limiting example, the stain fluorescein is conceded to stain damaged cells 76 where the cell membrane has been damaged or to stain areas between the cells 76, or the "intercellular spaces." The stain rose bengal, and lissamine green, which is thought to be similar to rose bengal, are other known stains that can be used to stain devitalized cells or completely dead cells 76. A fifty (50) mL drop of fluorescein may be placed onto the tear film of the eye 50, followed by a similar drop of lissamine green or rose bengal (block 78 in FIG. 13). It may be desirable to use significant volume of stain, which will then run over the lid margins 40 and stain the lid margins 40 effectively. If the devitalized and/or dead cells 76 and the lid margins 40 are not compromised, one will see a very thin line, approximately 0.1 mm in thickness.

After the lid margins 40 are stained, a period of time is allowed to pass (e.g., approximately 60 seconds) (block 80 in FIG. 13) before examining the lid margins 40 of the patient (block 82 in FIG. 13). This delay in examination is so that blinking with staining applied takes effect on the areas of interest in the lid margin 40. Lid margins 40 have been found to have some areas that are impacted by devitalized and/or dead cells 76 and other areas which are not impacted by devitalized and/or dead cells 76. The most severe anatomical changes and widening of the Line of Marx 64 may occur temporally. It may be desired to identify the areas of the lid margin 40 impacted by devitalized and/or dead cells 76 and specifically treat these areas of change rather than the areas of the lid margin 40 that are not changed.

After a patient has been diagnosed with a build up of devitalized and/or dead tissue cells 76 in the lid margin 40 preventing or reducing the transport of lipid to the tear film, the patient can be treated (block 84 in FIG. 13). Specifically, the devitalized and/or dead tissue cells 76 in the lid margin 40 can be removed with any number of procedures and devices, examples of which are described below. The goal with the removal treatment is to "smooth" the surface at the Line of Marx 64. As non-limiting examples, the features of the eyelids all conspire to require an individual technique which can be used by the practitioner with an instrument allowing that flexibility and visualization of the areas in the lid margin 40 to be treated after staining procedures are performed: (1) dramatically different eyelid shape temporally, centrally, and nasally; (2) different degrees of lid margin 40 deformation; (3) different degrees of the width of the Line of Marx 64; (4) the anterior movement of the Line of Marx 64; and (5) the nature of the meibomian gland orifices 48, their location, and whether or not they have blockages.

In one embodiment, a manual process may be employed to remove devitalized and/or dead tissue cells 76 formed on the lid margin 40, including at the Line of Marx 64 and on keratinized cells and aberrant mucosal tissue. As a non-limiting example, a swab-type device, including foam or sponge-tipped devices, may be rubbed over the lid margin 40 and the meibomian gland orifices 48. As another non-limiting example, a device with a sharp surface or blade may be used to apply a scraping motion to the devitalized and/or dead tissue cells 76 to remove the devitalized and/or dead tissue cells 76 from the lid margin 40. The devitalized and/or dead tissue cells 76 formed on the lid margin 40 may be heated to loosen devitalized and/or dead tissue cells 76 before and during removal. For example, the devitalized and/or dead tissue cells 76 may be heated to 42.5 degrees Celsius.

This removal may be effective in preventing the described anatomical changes and difficulties by preventing accumulation of devitalized and/or dead tissue cells 76 in the lid margin 40. The rubbing of the devitalized and/or dead tissue cells 76 may be provided by manual movement of 1 or 2 millimeters (mm) as a non-limiting example. It is necessary to move a sharp edge or some sharpened and/or textured mechanical surface over the cells either back and forth or within a particular direction to effect a scraping action. In this and other embodiments, the mechanical surface may include a sharpened edge, or a textured or other surface. Examples of a textured surface include, but are not limited to, a roughened surface, a matte finish, one or more sharpened edges, one or more raised areas, or other regular or irregular surface variations. However, it should be noted that this treatment alone may not be adequate to rectify more significant abnormalities in the lid margin 40.

Next, the devitalized and/or dead tissue cells 76 in the lid margin 40 in the Line of Marx 64 may be removed (block 86 in FIG. 13). It should be noted that, in some embodiments, the method of treatment may comprise only the step of removing the devitalized and/or dead tissue cells 76 in the lid margin 40 (block 86), with the other steps being optional. In another embodiment, a mechanical treatment device, such as the mechanical treatment devices described below with regard to FIGS. 14-42, having at least one sharpened and/or textured mechanical surface may be provided. The mechanical treatment devices may be used to remove the devitalized and/or dead tissue cells 76 in the lid margin 40, as in block 86 of FIG. 13, for example, by moving one of the at least one textured surface and a lid margin of an eyelid proximate to the Line of Marx of the eyelid against the other to exfoliate devitalized and/or dead cell material from the lid margin.

There are several ways of evaluating treatment of the removal of devitalized and/or dead tissue cells 76 in the lid margin 40 in the Line of Marx 64 (block 86 in FIG. 13). One treatment evaluation is by the subjective response of the patient by a technician employing a sham treatment. The sham treatment may involve applying a force to the area of the eye lashes of the eyelid where function would not be impacted, but the patient would think both eyes were treated. The patient can then provide feedback as to the efficacy of the treatment.

Another evaluation of treatment technique is by objective evaluation of the lid margin 40. After completing debridement of the altered devitalized and/or dead tissue cells 76, these areas may still show some staining. Staining, as previously explained, by its very nature, only stains cells that are altered whenever devitalized and/or dead tissue cells 76 are scraped. Thus, these altered stained devitalized and/or dead tissue cells 76 are part of, and are attached to, the lid margin 40 and may or may not have deeper normal cells underneath them. After completing debridement of the altered devitalized and/or dead tissue cells 76, these areas may still show some staining. Normal cells do not stain. If one were to then restain the lid margin 40 (block 86 in FIG. 13), additional staining may result due to the nature of the action of your scraping action against the last layer of devitalized and/or dead tissue cells 76 scraped. This may result in normal deeper cells; the scraping of the debridement of devitalized and/or dead tissue cells 76 will be traumatic and will result in some new staining. Within several days, the stain will no longer be present, but such may vary by patient. The treatment can be repeated as desired if the treatment is not fully effective (block 88 in FIG. 13).

Now that the diagnosis and treatment of devitalized and/or dead tissue cells 76 formed on the lid margin 40 have been discussed, the remainder of this disclosure will present different devices that can be configured and used to remove devitalized and/or dead tissue cells 76 formed on the lid margin 40.

Figure 14A:
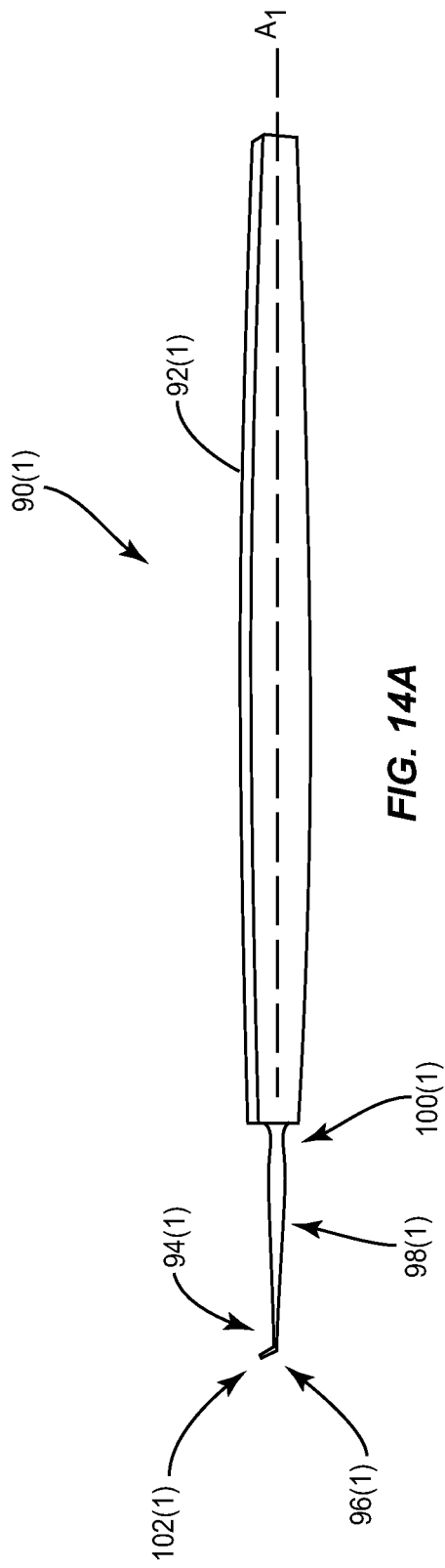
FIG. 14A is an exemplary treatment device configured to remove devitalized and/or dead tissue in the lid margin in the form of a "golf club" shaped spud.
Figure 14B:
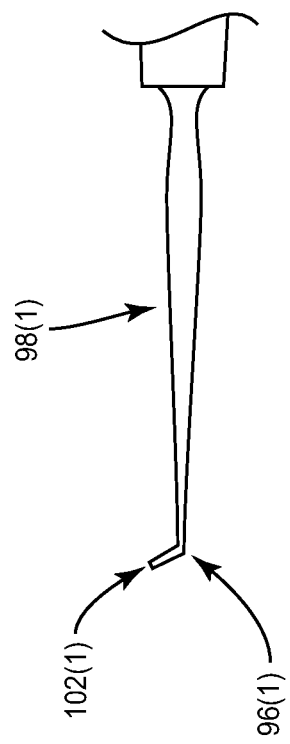
FIG. 14B is a close up of the treatment area of the exemplary device shown in FIG. 14A.

In one embodiment, a mechanical treatment device 90(1) is an instrument provided in the form of a "golf club" shaped spud, as illustrated in FIGS. 14A and 14B. As shown in FIG. 14A, the mechanical treatment device 90(1) includes a handle 92(1) configured to be gripped by a technician to maneuver a sharp edge or a textured mechanical surface 94(1) in this embodiment (e.g., a sharpened edge, or textured or other surface) located at a distal end 96(1) of a neck portion 98(1). The handle 92(1) may be provided with an outer surface formed by surfaces (polygonal shaped from a cross section view) configured to be grasped similar to a pencil. The neck portion 98(1) is attached to the handle 92(1) at a proximal end 100(1) of the neck portion 98(1).

With continuing reference to FIGS. 14A and 14B, a technician can maneuver the sharpened and/or textured mechanical surface 94(1) on devitalized and/or dead tissue cells 76 formed on the lid margin 40 to remove the devitalized and/or dead tissue cells 76 (not shown). The mechanical surface 94(1) may have corrugations, sharp points, or a sandpaper like surface as non-limiting examples. It may be desired that the mechanical surface 94(1) include radii at the periphery of the surface with no sharp corners or edges to avoid the mechanical surface 94(1) digging into or gouging tissue. In addition, the angled mechanical surface on 94(1) that is effective in removing devitalized and/or dead cells mimics in appearance the distal region indicated by angulation 102(1) and distal end 96(1) on FIG. 14A. As illustrated in the close-up diagram of the distal end 96(1) of the mechanical treatment device 90(1) in FIG. 14B, angulation 102(1) is considered the "toe" of the angled mechanical surface and distal end 96(1) is considered the "heel" of the mechanical surface. The distal surface between angulation 102(1) and distal end 96(1) is applied to the tissue at the lid margin and is used in a scraping motion to provide debridement. The neck portion 98(1) may have a certain angulation 102(1) located at the distal end 96(1) of the neck portion 98(1) to dispose the mechanical surface 94(1) at an angle with respect to longitudinal axis $A_1$ of the handle 92(1) or the central axis of the handle 92(1). This may improve the ability of a technician to reach or contact devitalized and/or dead tissue cells 76 formed on the lid margin 40 for removal. The "toe" and "heel" of the angled textured surface are rounded to avoid gouging into tissue and preferably, the "toe" is rounded to present a smooth bulbous profile to reduce potential damage to the eye in the event of inadvertent contact with the eye.

During removal, the devitalized and/or dead tissue cells 76 attach to the mechanical surface 94(1) where they can be wiped off (e.g., between 2 and 5 times during the cleaning of the approximate 30 mm wide lid margin). With very severe cases of build up of devitalized and/or dead tissue cells 76 in the lid margin 40, the mechanical surface 94(1) may need to be cleaned for every 2 to 3 mm of scraping.

Figure 15B:
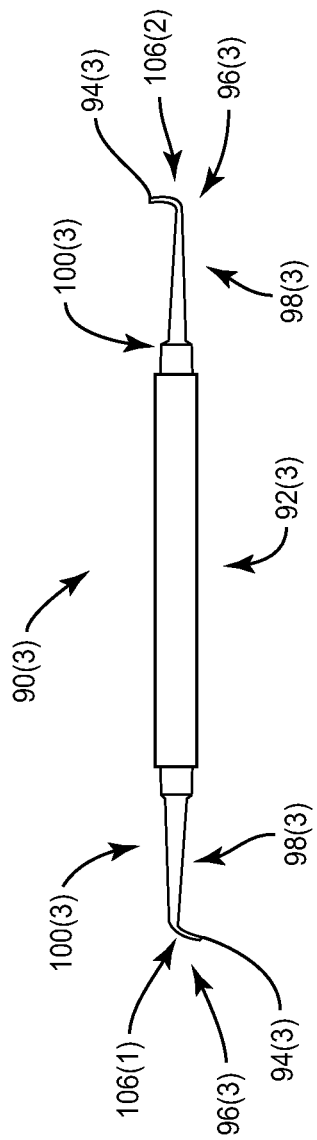
FIG. 15B is an exemplary hook mechanical treatment device configured to remove devitalized and/or dead tissue in the lid margin.

Other types of mechanical treatment devices can be employed to facilitate, simplify, provide more reproducible results, and greater efficacy to the debridement process in an effort to treat and remove devitalized and/or dead tissue cells 76 formed on the lid margin 40. For example, the mechanical treatment device 90(2) in FIG. 15A may be employed. The mechanical treatment device 90(2) may include curette-type devices 104(1), 104(2) disposed on each end of a handle 92(2). Other elements having similar functions to the elements in the mechanical treatment device 90(1) in FIG. 14A share common element numbers, but signified with '(2)', and thus will not be re-described. FIG. 15B illustrates another exemplary mechanical treatment device 90(3) that includes hook portions 106(1), 106(2) disposed at distal ends 96(3) of neck portions 98(3), wherein the hook portions 106(1), 106(2) include sharpened and/or textured mechanical surfaces 94(3) that can be used to remove devitalized and/or dead tissue cells 76 formed on the lid margin 40. FIG. 15C illustrates another exemplary mechanical treatment device 90(4) that includes cup scrapers 108(1), 108(2) disposed at distal ends 96(4) of neck portions 98(4), wherein the cup scrapers 108(1), 108(2) include sharpened and/or textured mechanical surfaces 94(4) that can be used to remove devitalized and/or dead tissue cells 76 formed on the lid margin 40.

To facilitate the observation of the removal of devitalized and/or dead tissue cells 76 formed on the lid margin 40 during the procedure, it may be beneficial to minimize the size of the distal end of a mechanical treatment device. It may be preferable that mechanical dislodging surfaces come provided at a ninety (90) degree angle to the neck (or at the side) to improve visibility of the cell dislodging process. Another embodiment would have the distal end of a mechanical treatment device made from optically clear or translucent material so that observation of the cell removal process could be enhanced.

Figure 16:
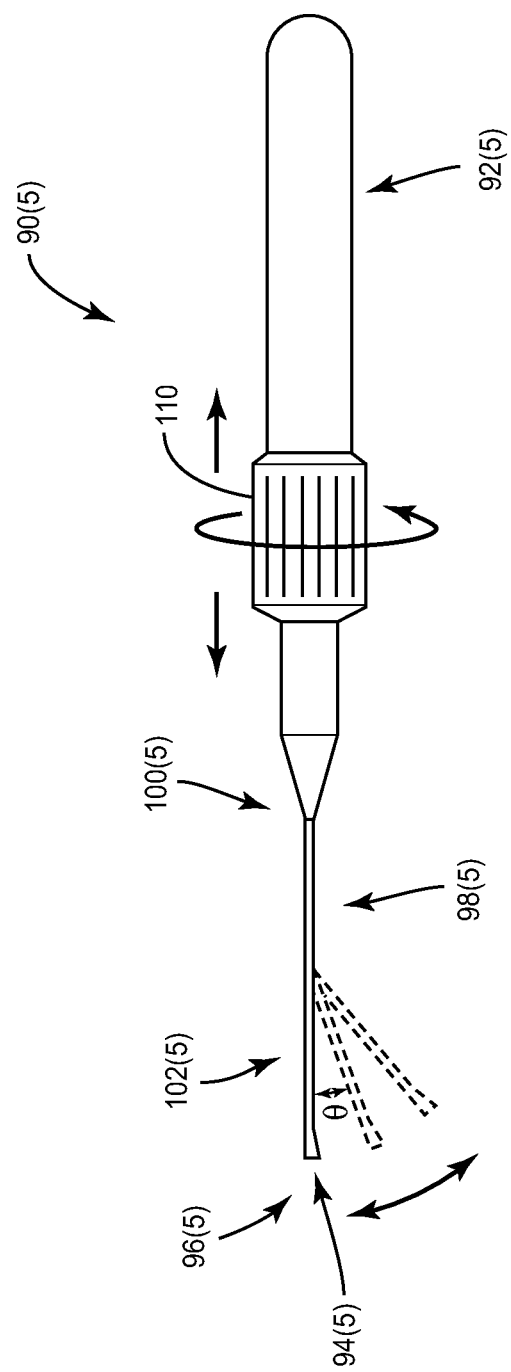
FIG. 16 is another exemplary mechanical treatment device that has an actuator to adjust the angle of a sharp edge or a textured mechanical surface configured to remove devitalized and/or dead tissue in the lid margin.

For angulation, various angles can be provided in a kit that would improve how the eyelid 42 surface and lid margin 40 is contacted. Alternatively, the angulation 102 of a mechanical surface 94 at the distal end 96 of a handle 92 of a mechanical treatment device 90 can be manually adjusted by the practitioner through an actuator positioned on the handle 92 to readjust the angle of contact on the eye. For example, FIG. 16 illustrates another mechanical treatment device 90(5) where the angulation 102(5) of a sharpened and/or textured mechanical surface 94(5) at the distal end 96(5) of a handle 92(5) can be manually adjusted by the practitioner through an actuator 110 positioned on the handle 92(5). The actuator 110 may be a button or a knob, as examples. The actuator 110 can be manipulated the by practitioner on the handle 92(5) by depressing, sliding, or rotating the actuator 110. The actuator 110 readjusts the angle of contact or rotation of the neck portion 98(5) of the mechanical treatment device 90(5) to adjust the angle and/or rotate the mechanical surface 94(5) during treatment.

In addition, it may be desirable to provide the following additional features for angulation 102 and the neck portion 98 of a mechanical treatment device to further improve the ability to dislodge devitalized and/or dead tissue cells 76 formed on the lid margin 40. It may be desirable that the neck portion 98 and angulation 102 are each malleable (or just one of these portions of the device) and may be re-formed by the practitioner to provide the best angle of reach to the eye. It may be desirable to have the neck portion 98 flexible so that the amount of force being applied to the eyelid is reduced. It may be desirable that the handle 92 be adapted to fit in the hand with finger grips or rest against the palm of the hand. Ideally, the mechanical treatment devices 90 for this procedure enable a one-handed procedure.

Figure 17A:
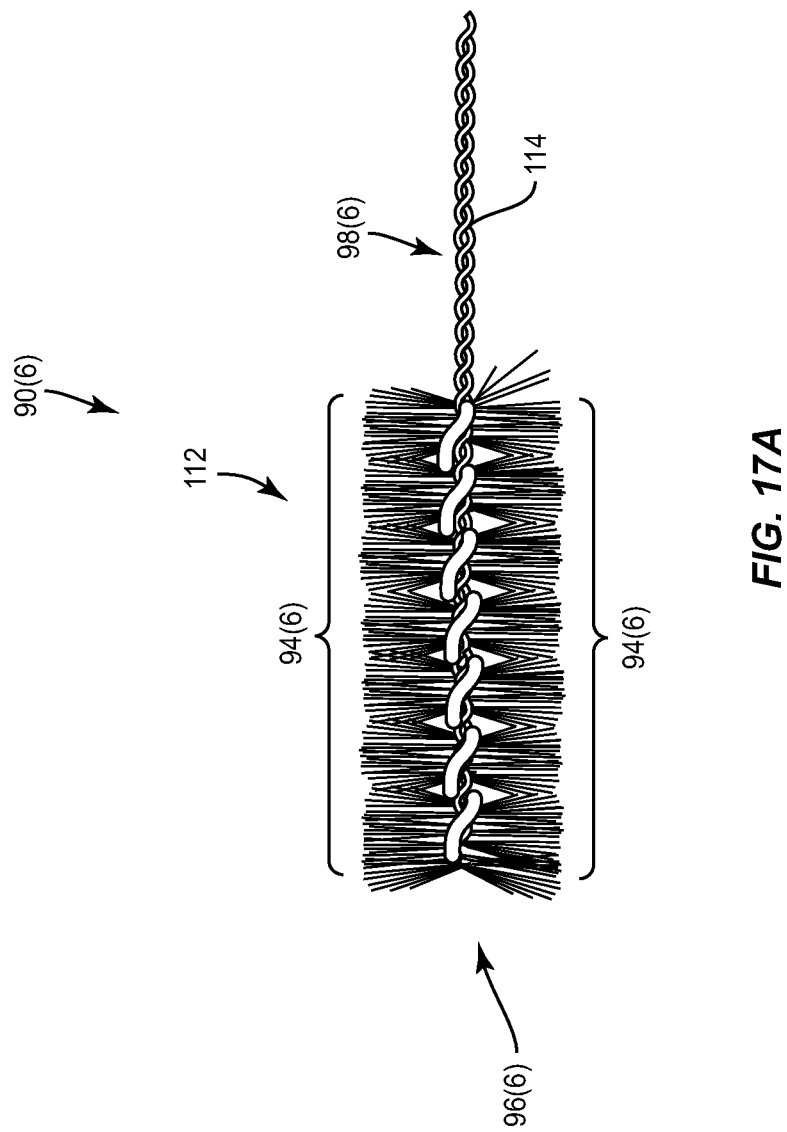
FIG. 17A is an exemplary deburring brush that includes an abrasive brush surface configured to be controlled by a treatment device to remove devitalized and/or dead tissue in the lid margin.
Figure 17B:
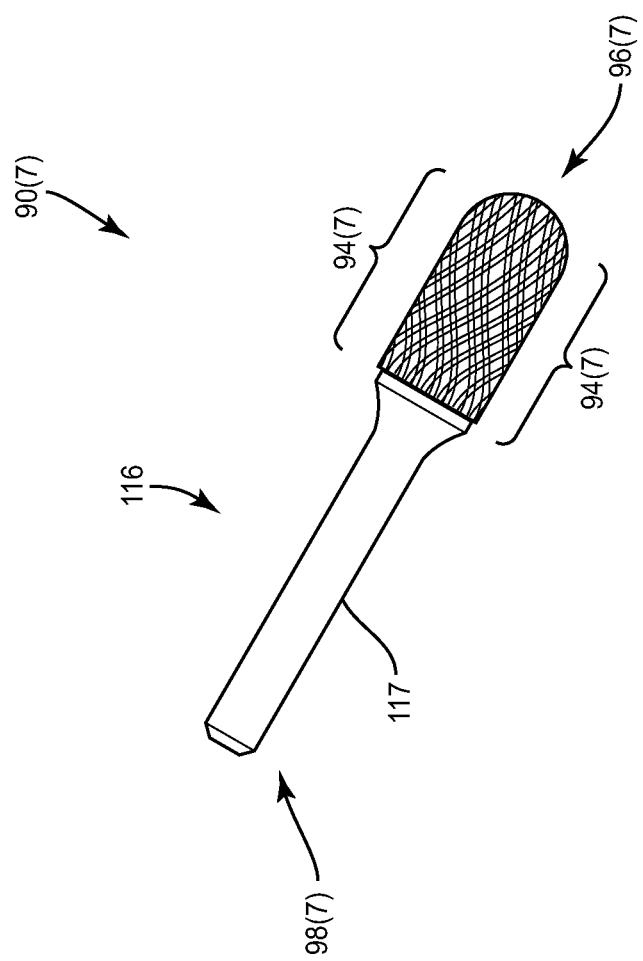
FIG. 17B is an exemplary deburring device that includes an abrasive brush surface configured to be controlled by a treatment device to remove devitalized and/or dead tissue in the lid margin.

Other alternatives can be provided for tips to be disposed at distal ends 96 of the mechanical treatment devices 90 to provide sharpened and/or textured mechanical surfaces 94 for removal of devitalized and/or dead tissue cells 76. For example, FIG. 17A illustrates a deburring brush 112 that includes an abrasive brush surface 94(6). The deburring brush 112 includes a shaft 114 that can either be part of the neck portion 98(6) or be coupled to the neck portion 98 of a mechanical treatment device 90. The deburring brush 112 can be controlled to be rotated or slid, rocked, and/or vibrated, to be applied to cells of interest. FIG. 17B illustrates a deburring device 116 that includes textured mechanical surfaces 94(7). The deburring device 116 includes a shaft 117 that can either be part of the neck portion 98(7) or be coupled to the neck portion 98 of a mechanical treatment device 90. The deburring device 116 can be controlled to be slid, rocked, ultrasonically activated, and/or vibrated, to be applied to cells of interest.

Mechanical treatment devices, including the mechanical treatment devices 90(1)-90(5) discussed above with regard to FIGS. 14A-16, can include driving force components to either move or aid in the movement of sharpened and/or textured mechanical surface 94. Non-limiting examples include DC powered motors, AC powered motors, and forced air driven tools, ultrasonically driven tools (or vibrational energy). Examples of these and other types of components are described in detail in U.S. Pat. No. 7,981,146. Manual manipulations can also be employed by the practitioner on the handle 92 that actuate the mechanical surface 94 at the distal end 96 of the mechanical treatment device 90 (e.g., squeezing, rotating or depressing an actuator that moves, slides, rocks, ultrasonically activates, or vibrates the distal end 96 of the mechanical treatment device 90). All of these driving forces referenced above can be used to axially move, rotate, rock, ultrasonically activate, or vibrate a mechanical surface 94 at the eyelid. These mechanical surfaces 94 can be configured to selectively or non-selectively dislodge or remove the cells of interest from devitalized and/or dead tissue cells 76 formed on the lid margin 40.

Figure 18A:
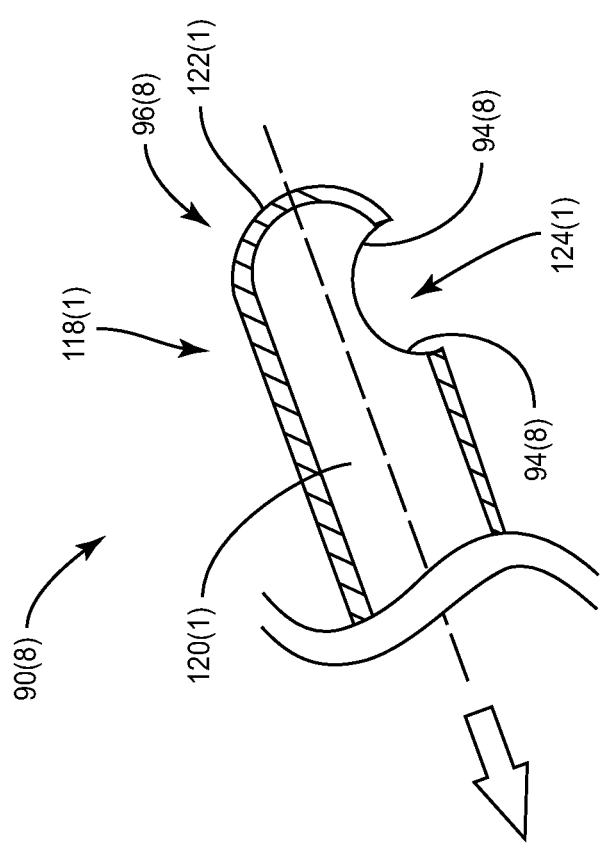

The distal tip of a treatment device can have a sharp or mechanical feature that can be driven, as described above. To facilitate observation of cell dislodgement process, aspiration means can be provided in the device to remove the dislodged cells from the field of view. One such embodiment is shown in cross-section in FIG. 18A. In FIG. 18A, a tip 118(1) is shown that can be disposed at the distal end 96 of a neck portion 98 of a mechanical treatment device 90. The distal end 96(8) of the tip 118(1) includes a hollow chamber 120(1) so that the dislodged cells can be removed by an aspiration means 122 connected to the tip 118(1) and to the hollow chamber 120(1). The aspiration means 122 can be provided by a pump, wall suction (supplied by the hospital or facility), or a manual negative pressure system. The aspiration means 122 can be controlled by a button on the handle, an exhaust hole that can be closed by the practitioner (by closing the hole with a finger tip as an example, vacuum is applied, by leaving the hole open no vacuum is supplied), by foot pedal, or other actuation.

With continuing reference to FIG. 18A, the distal end 96(8) of the tip 118(1) can include a rounded outer surface 122(1) with a concave side hole 124(1) for selectively or non-selectively removing the dislodged cells from the field of view. The sharpened and/or textured mechanical surfaces 94(8) at the concave side hole 124(1) can be moved, slid, rocked, or vibrated by one of the driving forces described earlier. Note that the mechanical surfaces 94(8) of the entire concave side hole 124(1) can be used for tissue and cell removal or selected areas or quadrants of the concave side hole 124(1). The distal end 96(8) could also have a hole for applying the mechanical surface 94(8) at the very distal end 96(8) itself, or be provided with multiple side holes for removing the cells in which a diametrically opposite side hole can be rotated into use if the first side hole becomes clogged with cellular material. The side holes can be located in a number of positions on the distal end 96(8), including the very distal end or being a distal end hole. In addition, although not shown in FIG. 18A, an additional lumen could be provided along the hollow distal end 96(8) for supplying saline or other fluid if it is desirable to clear the field of view by applying irrigation fluid. Alternatively only an irrigation means may be employed. In addition, the lumen can be used to supply mineral oil or other unbinding agent.

Figure 18B:
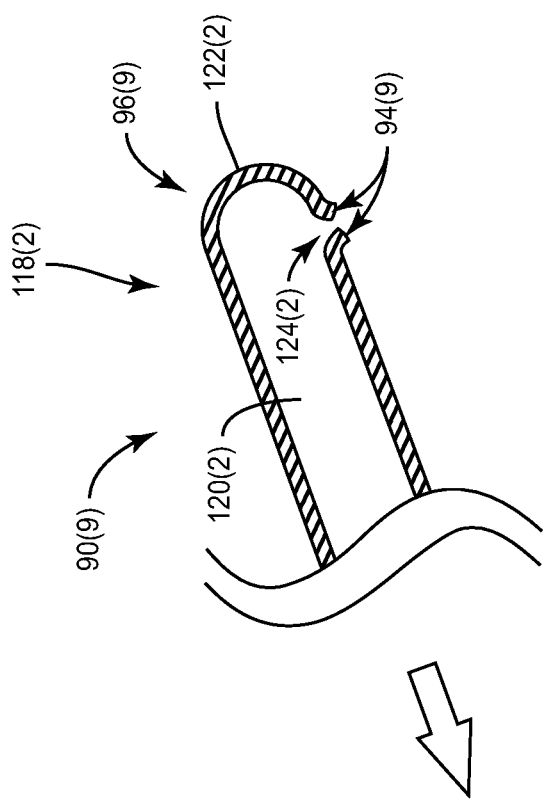

FIG. 18B shows an alternative tip 118(2) with a hollow distal end 96(9). In this configuration, the instrument has a rounded distal end 96(9), with a convex side hole 124(2) that has mechanical surfaces 94(9) that emanate from the periphery of the side hole 124(2). Through the hollow distal end 96(9), the aspiration means 122 can be supplied to remove the cells as they accumulate upon the mechanical surfaces 94(9). The convex side hole 124(2) can provide greater mechanical advantage and accessibility for the physician in reaching the target tissue and cells. There can be multiple convex side holes as well as different locations on the distal end including at the very distal end 96(9) or a distal end hole.

Figure 18C:
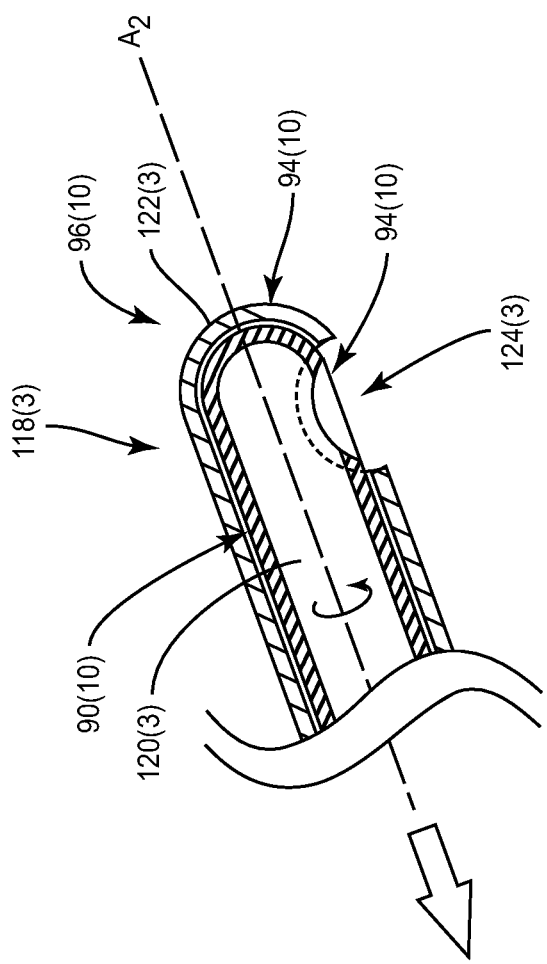

Instead of the hollow distal end 96 coming with a side hole 124 (or distal end hole or multiple holes) that has a mechanical surface 94 for dislodging devitalized and/or dead tissue cells 76, the hollow distal end 96 can come with an interior piece that performs the mechanical action of removing the cells. One configuration of such a tip 118(3) that can be provided as part of a mechanical treatment device 90(10) is shown in FIG. 18C. In this embodiment, the tip 118(3) is provided within the hollow distal end 96(10). The tip 118(3) is configured to be rotated about the central axis $A_2$ of the mechanical treatment device 90(10) in which a mechanical surface 94(10) is exposed and dislodges the cells within or adjacent to a side hole 124(3). The rotation of the tip 118(3) can also be vibrational, translational (slid), or rocked (slight rotations about the central axis). DC motors, AC motors, forced air, ultrasonically, or manually driven components can also be provided as part of the mechanical treatment device 90(10) to move the mechanical surface 94(10). In this configuration, the tip 118(3) is hollow and the aspiration means 122 is applied through a hollow chamber 120(3). The aspiration means 122 can also be applied through the hollow distal end 96(10), as described above. The mechanical surface 94(10) can be composed of irregular surface features, sandpaper, sharp edge(s), or bristles as described previously. In this embodiment, the mechanical surface 94(10) has a concave appearance. In another embodiment, the mechanical surface can protrude in a convex configuration to more easily affect the cells or tissue of interest in a similar fashion as a side hole 124(3) can be convex or concave, as discussed above in FIGS. 18A and 18B.

As opposed to a supplied aspiration means 122, the removal of cells can occur by an auger action within the hollow distal end 96 of a tip 118. In this regard, FIG. 18D shows another embodiment of a tip 118(4) that can be employed with a mechanical treatment device 90(11). The tip 118(4) does not require a separate aspiration means although aspiration (as well as irrigation through a second lumen) can be performed with this tip 118(4), if necessary. In this configuration, the hollow distal end 96(11) of the tip 118(4) contains an interior auger 126 that can be made by any spiral or helical pitch configuration. The auger 126 can provide a mechanical dislodging surface 128 that can act as a mechanical surface 94(11) exposed at a side hole 124(4) of the tip 118(4). The mechanical dislodging surface 128 can include a textured or other surface, including one or more roughened or sharpened edges. In practice, the auger 126 is rotated about the central axis $A_3$ of the mechanical treatment device 90(11). By controlling the pitch of the auger 126, the direction of rotation, and the speed of rotation, the cellular material that is being dislodged can be directed back through the hollow distal end 124(4) in a proximal direction and removed from the field of view. For example, in one embodiment, the mechanical dislodging surface 128 may be pitched and/or textured such that the mechanical dislodging surface 128 scrapes against the lid margin when the lid margin is moved against the textured surface in a first direction, and slides against the lid margin when the lid margin is moved against the mechanical dislodging surface 128 in the opposite direction.

Treatment devices may also be employed that apply heat to the keratinized tissue of the lid margin 40 that can result in a denaturing of binding mechanisms in the devitalized and/or dead tissue cells 76. This heat application may soften the devitalized and/or dead tissue cells 76, thus requiring less force for removal. It has been observed that a temperature of 42.5 degrees Celsius is effective in denaturing the binding mechanisms devitalized and/or dead tissue cells 76 to the keratinized cells of the lid margin 40. However, higher and lower temperatures for varying time durations can be applied as well. There are several ways in which the denaturing of these devitalized and/or dead tissue cells 76 can be accomplished by heat and force. For example, prior to the removal procedure, the eyelid margins 40 can be warmed by a variety of devices and methods, examples of which are described below in more detail. A practitioner would need to provide for the patient's cornea/eye to not be affected by the heating process. In addition, the addition of mineral oil or other unbinding agent on the target tissue can be beneficial for the removal of these devitalized and/or dead tissue cells 76.

Figure 19A:
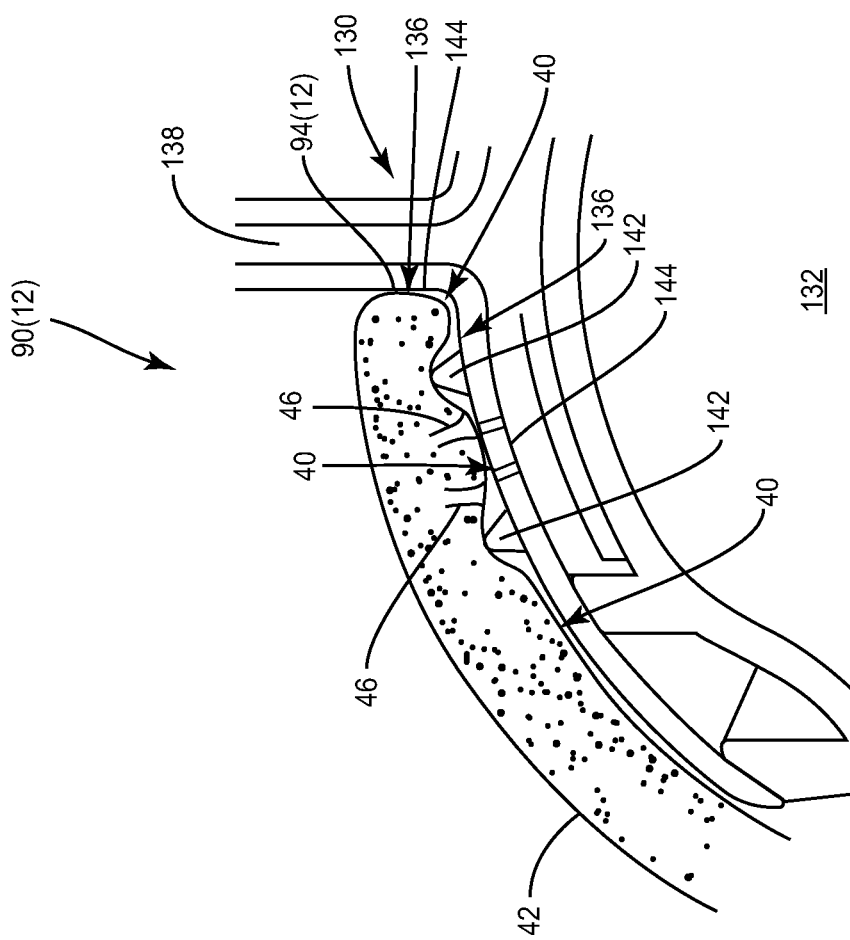
FIG. 19A illustrates an embodiment of an eyecup configured to provide thermal zones to the lid margins to soften devitalized and/or dead tissue before removal, wherein the thermal zones may also include optional textured mechanical surface zones to remove the softened devitalized and/or dead tissue.

In one embodiment illustrated in FIG. 19A, a thermal preconditioning eye cup 130 can be provided. The eye cup 130 can include a thermal activated surface to heat the lid margins 40 of an eyelid 42 prior to cell removal. As illustrated in FIG. 19A, the eye cup 130 can be placed on the eye globe 132 to protect the eye and cornea (not shown). The eye cup 130 can be charged by a thermal producing means 133 (not shown) to heat a thermal zone 136. Only one eyelid 42 is shown in the diagram; however, both eye lids can be treated at the same time. Likewise, the thermal zone 136 can extend further up on a shaft 138 and more lateral to both raised areas 142 shown on the eye cup 130. In practice, the eye cup 130 would be placed to precondition the eyelid margins 40 prior to cell and tissue removal. An electronic controller like that provided in U.S. Pat. No. 7,981,146, entitled "Inner Eyelid Treatment for Treating Meibomian Gland Dysfunction," which is incorporated herein by reference in its entirety, may be used to control the heat applied by the thermal zone 136 of the eye cup 130. The exterior surface of the eye cup 130 could have an application of mineral oil or other unbinding agent on it at the location of the lid margin 40. The eye cup 130 could also have a coating of mineral oil or other unbinding agent integrated onto the exterior surface of the eye cup 130.

These and other instruments can be pre-heated to the desired temperature by incubating within an oven or other heating apparatus until needed for tissue removal. Then, after heat application to the lid margin 40 by the eye cup 130, a mechanical treatment device 90, like any of those previously described above, can supply the force to remove the devitalized and/or dead tissue cells 76 from the lid margin 40. Alternatively, the eye cup 130 could also include the treatment device 90 to remove the devitalized and/or dead tissue cells 76 from the lid margin 40. Alternatively, just the distal end 96 of the instrument that is pre-heated can be placed onto a handle 92 prior to application to the eye lid margin and tissue removal.

In some embodiments, the distal 96 or the mechanical surfaces 94 of the treatment devices 90 can be heated to an elevated temperature. Heating the distal end 96 of the treatment device 90 can be internally driven by a heating apparatus that is controlled by DC battery, AC power, or other heating means. An RF/microwave energy heating mechanism can be employed to selectively heat just the distal end 96 of the treatment device 90 or the mechanical surface 94, such as described in P.C.T. Patent Application No. PCT/US12/44650, entitled "Methods and Systems for Treating Meibomian Gland Dysfunction Using Radio-Frequency Energy," incorporated herein by reference in its entirety. The RF/microwave energy heating mechanism can be configured to heat both the treatment device 90 and the tissue around the mechanical surface 94. For instance, the RF/microwave field would heat the distal end (or mechanical surface) and the nearby or adjacent tissue. In another embodiment, the heating of the nearby tissue can be accomplished by selectively heating a gel, a coating of mineral oil or other agent, or other fluid at the tissue of interest. The heating would be done at a pre-determined tissue temperature. The temperature can be controlled by a temperature sensor or controller, as described in U.S. Pat. No. 7,981,146 referenced above. Alternatively, the RF/microwave energy heating can be directed to only heat the tissue and not the distal end 96 of the treatment device 90. Finally, the heating of the treatment device 90 could also include the interior heating of the hollow distal end tips 118 previously described to allow for the easier passage of the removed cells and tissue in a heated state with aspiration means. In some mechanical embodiments, the movement (micro movements or ultrasonic applications) can supply elevated temperature at the distal end 96 as a result of the mechanical action at the distal end 96 of the treatment device 90. In this instance, the elevated temperature of the distal end 96 of the treatment device 90 due to mechanical movements would be beneficial for the removal of the cells of interest.

In another embodiment, the hollow distal end 96 of the tips 118 described above can supply heated air, $CO_2$, or other gas through the hollow distal end 96 onto the tissue of interest. The air or gas is heated and delivered by heating and pumping sources not shown in the diagrams. In addition, the pumping of heated air or gas can be alternated with aspiration means 122, depending upon an initial heating of tissue with the forced heated air or gas, followed by aspiration as tissue or cells accumulate on the mechanical surfaces. The switching of forced heated air or gas and aspiration can be controlled by the physician through various types of hand piece buttons, valves, or similar controlling mechanisms. In combination with the forced heated air or gas, the hollow lumen can be used to place mineral oil or other agent for unbinding at the tissue of interest.

As an alternative to utilizing a separate treatment device for the dislodgement of devitalized and/or dead cells 76, the mechanical surfaces 94 that remove these cells can be integrated onto the exterior surface of the eye cup 130 in FIG. 19A or LipiFlow® Activator described in U.S. Pat. No. 7,981,146 to provide a treatment device 90(12). One such embodiment is illustrated in FIG. 19A. The process could involve causing the thermal zones 136 to apply heat to the lid margin 40 (described in greater detail with respect to FIGS. 25-42 below), and moving the shaft 138 after 8-10 minutes of heating to cause mechanical surfaces 94(12), which may be provided as sand paper-type surface, to be moved about the lid margin 40.

In this regard with reference to FIG. 19A, the eyelid 42 rests of top of the eye cup 130 with shaft 138. On the exterior of the eye cup 130 is a mechanical surface 94(12) forming a mechanical surface zone 144 that can be moved, slid, vibrated, or rotated through a controlling and power mechanism through connection. (Power means not shown.) In addition, the exterior portion of the eye lid 42 can be contained by the LipiFlow® Activator (not shown) as described previously for the LipiFlow® procedure. What is not shown is the mechanism for moving, sliding, rotating, or vibrating the mechanical surface zone 144. The mechanical surface zone 144 may be configured to move independently from the rest of the eye cup 130 so that only the lid margin 40 area near the mechanical surface zone 144 would be affected. It would be the intention of the powering mechanism (not shown) to not disrupt or agitate the eye globe 132.

Figure 19B:
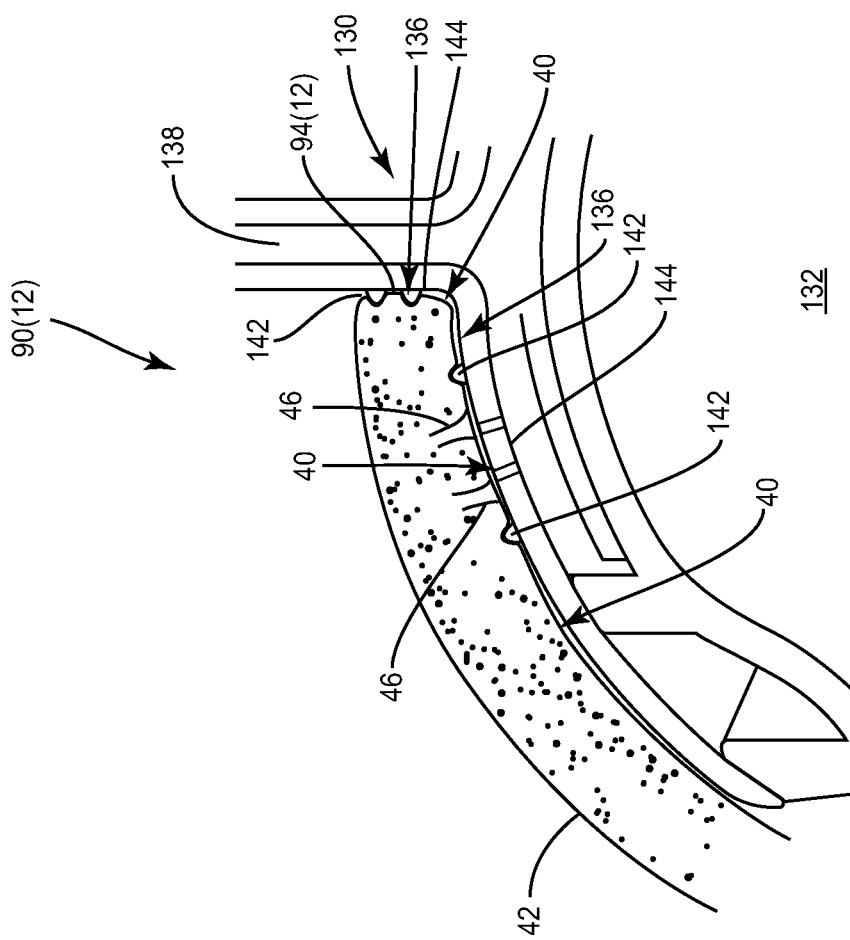
FIG. 19B illustrates an embodiment of an eye cup where the optional textured mechanical surface zone is provided on the shaft portion of the device.

FIG. 19B shows another configuration of the mechanical surface zone 144. The mechanical surface zone 144 contains ridges, roughened surface finish, or a less lubricious surface finish 138 positioned near the base of the exterior surface of shaft 138 that contacts the eye lid 42. Alternatively, the mechanical surface zone 144 can be positioned on both shaft 138, as seen in FIG. 19B, and eye cup 130, as seen in Figure 19A. Additional features of the eye cup are described in greater detail below with respect to FIGS. 25-28.

Figure 19C:
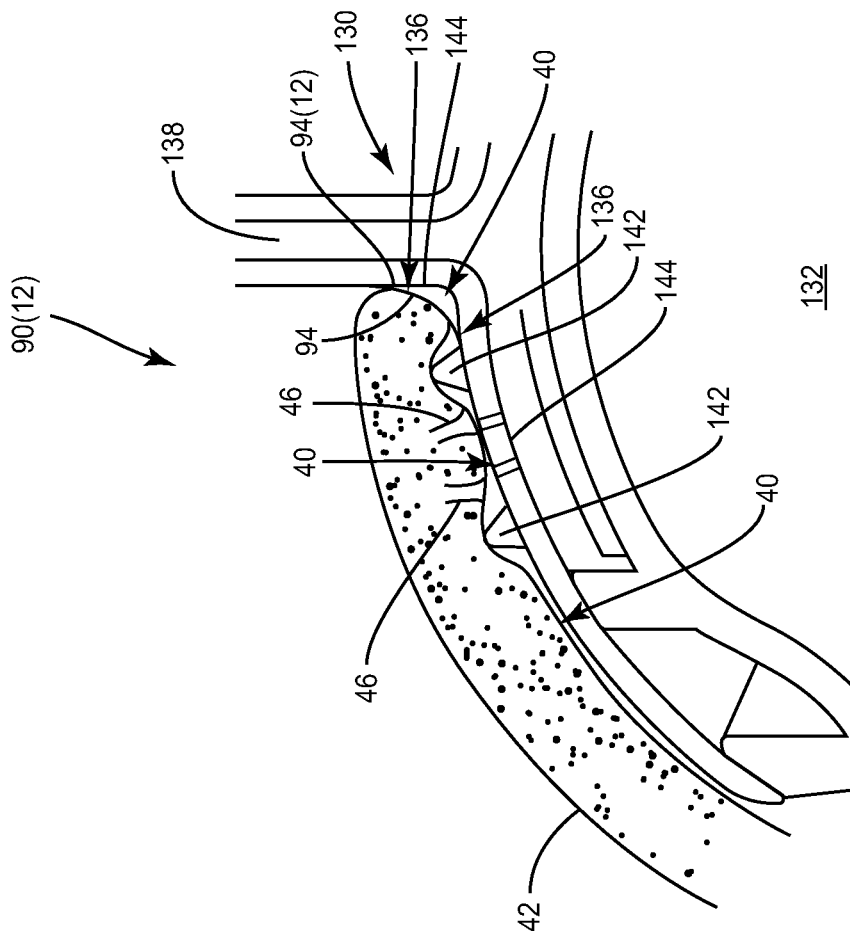
FIG. 19C illustrates an embodiment of an eye cup where the optional textured mechanical surface zone is specifically configured as an angled or concave surface.

FIG. 19C shows another configuration of the eye cup 130 with a mechanical surface 94(12) that is shaped to a concave or angled surface to form a more tightly fitting surface to the eyelid margin. The power means, not shown in FIG. 19C, is the mechanical action that occurs during a LipiFlow® treatment. As the inflatable bladders (not shown) are inflated and deflated as part of the compressive forces of the treatment regime, the inflations create mechanical movement of the eyelids on the mechanical surfaces 94 found preferentially on concave or angled surface 94. Whereas the compressive forces are occurring in generally an upward and downward motion on the eye cup 130, due the variations in tissue thickness and the action of the inflatable bladders in the mechanical surface zone 144, the resultant motion on the eyelids can be sideways, rotational, or variable. In addition, the mechanical action of the textured surfaces can be introduced into the treatment cycle at predetermined or selected time point or multiple time durations within a treatment cycle. As an example, the eye lid could be preconditioned with a heating cycle with a subsequent exposure to a textured mechanical surface at a point where the material at the Line of Marx has experienced some softening due to thermal exposure. Alternatively, the physician can select various degrees of exposure to a textured mechanical surface at his discretion during a treatment cycle as a response to the underlying condition of the patient. Additional discussion of the mechanics of the application of compressive force to the eyelids are described in greater detail below with respect to FIGS. 27-30.

Figure 20A:
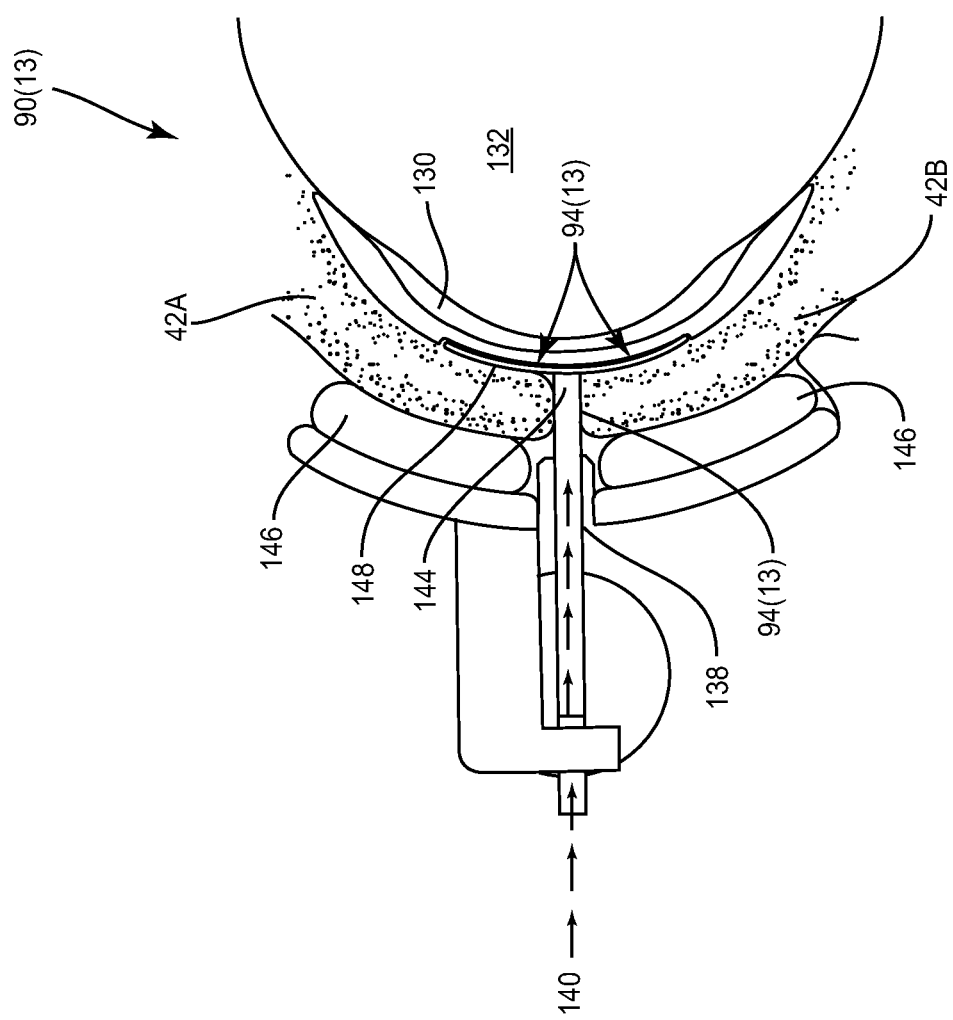
FIG. 20A illustrates another embodiment of an eyecup configured to provide thermal and textured mechanical surface zones to apply heat and force to the lid margins to soften and remove devitalized and/or dead tissue. The textured mechanical surface zone is activated by the expansion of bladders within the textured mechanical surface zones.

It may be desired to provide the treatments discussed herein as part of or after the LipiFlow® treatment is provided as described in U.S. Pat. No. 7,981,146. In this regard, as shown in FIG. 20A, the eyecup 130 of FIG. 19A shows that the mechanical surface zone 144 can be placed on an expanding member, such as a balloon bladder 146 like described in U.S. Pat. No. 7,981,146, to provide greater engagement with the eyelid margin 40. Greater engagement can be accomplished with direct mechanical expansion of this mechanical surface zone 144. On the shaft 138, there are thermal and mechanical surface zones 144 that work to heat the tissue of interest at the Line of Marx 64 to facilitate the removal of devitalized and/or dead cells 76. The heating can be programmed to work at any point in the LipiFlow cycle. As an example, it can be programmed within some intermediate time point in the LipiFlow® cycle such as the 8 minute mark. The thermal and mechanical surface zones 144 can be actuated to engage the tissue of interest. The engagement can be accomplished by radial expansion of the mechanical surfaces 94(13). Air can be provided to expandable bladders from the LipiFlow® generator (not shown) within shaft 138 as indicated by air flow 140. The engagement of the expandable bladders in the mechanical surface zone 94 can be enhanced by bladders 146 that provide bladder compression pressure that preferentially pushes the eyelids 42A, 42B towards the center shaft 138. The thermal and mechanical surface zones 144 can move against the tissue on eyelids 42A, 42B without affecting the stability or position of the eye cup protector 146. This combination of tissue removal can be done before, during, or after the LipiFlow® treatment. Incorporating mineral oil or other unbinding agent can be employed on the activator as discussed previously.

Figure 20B:
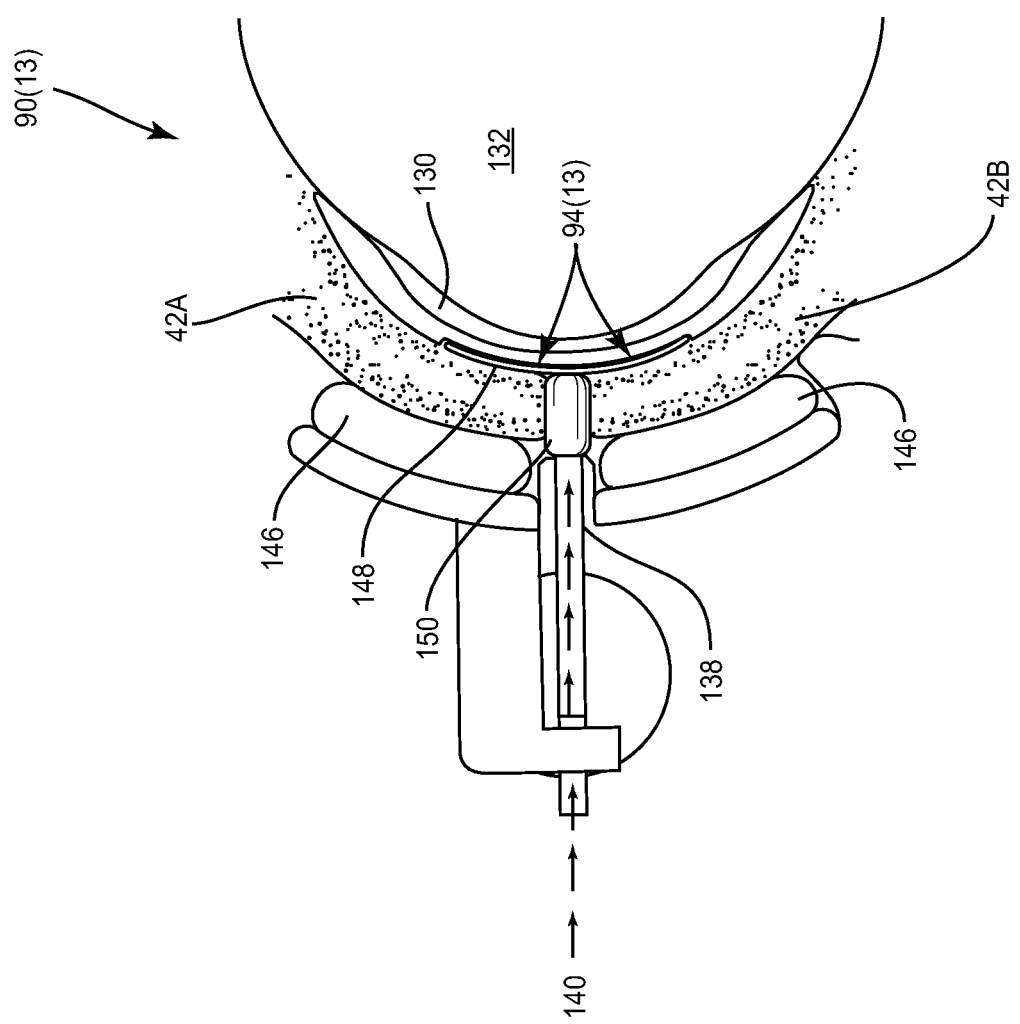
FIG. 20B illustrates another embodiment of an expandable bladder within the textured mechanical surface zone whereby the expandable bladder is located on the shaft.

FIG. 20B shows the LipiFlow® activator with bladders 146, shaft 138, and mechanical surfaces 94 for creating debridement on eyelids 42A and 42B on eye globe 132. In this configuration, a base portion of the shaft 138 contains an additional bladder 150 that can inflate and deflate during the LipiFlow® treatment. Bladder 150 provides an additional mechanical action on eye lids 42A and 42B and movement on mechanical surfaces 94. Bladder 150 can be controlled to inflate and deflate independently or simultaneously with bladders 146. In addition, the inflation of additional bladder 150 can create greater mechanical force on the eye lids 42A and 42B. Preferentially, bladder 150, and the resultant increased mechanical action, can be timed to occur after a predetermined amount of heating has occurred with the eyelids.

Figure 21:
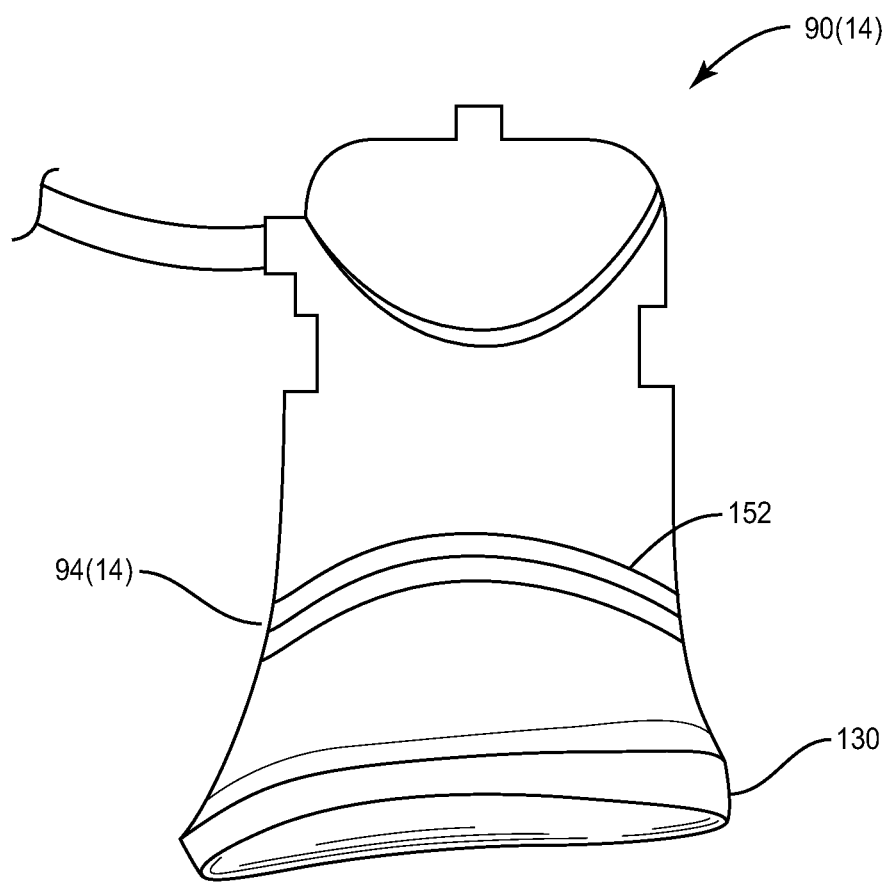
FIG. 21 illustrates a side view of an eye cup with scored lines that are placed parallel to the surface contour of the eye cup.

FIG. 21 depicts another configuration of a mechanical treatment device 90(14) having an eye cup 130 and a plurality of mechanical surfaces 94(14). Experiments determined that the degree of tissue removal can be influenced by the degree of roughness on the surface finish of the LipiFlow® activator. In this embodiment for debriding tissue, the surface finish of the mechanical surfaces 94(14) on the LipiFlow® activator can be created by the specific scoring of lines, grooves, or ridges 152 on the mechanical surface 94(14) that run parallel to the eye cup 130 as seen in FIG. 21. In this configuration, the mechanical forces can be directed along the eye lid (not shown) which is above eye cup 130. Scored lines, grooves or ridges 152 can be created by running a roughened instrument in a path parallel to the curved surface of the eye cup. Additional features of the eye cup 130 and other components of mechanical treatment device 90(14) and related devices are described in greater detail below with respect to FIGS. 25-30.

Figure 22:
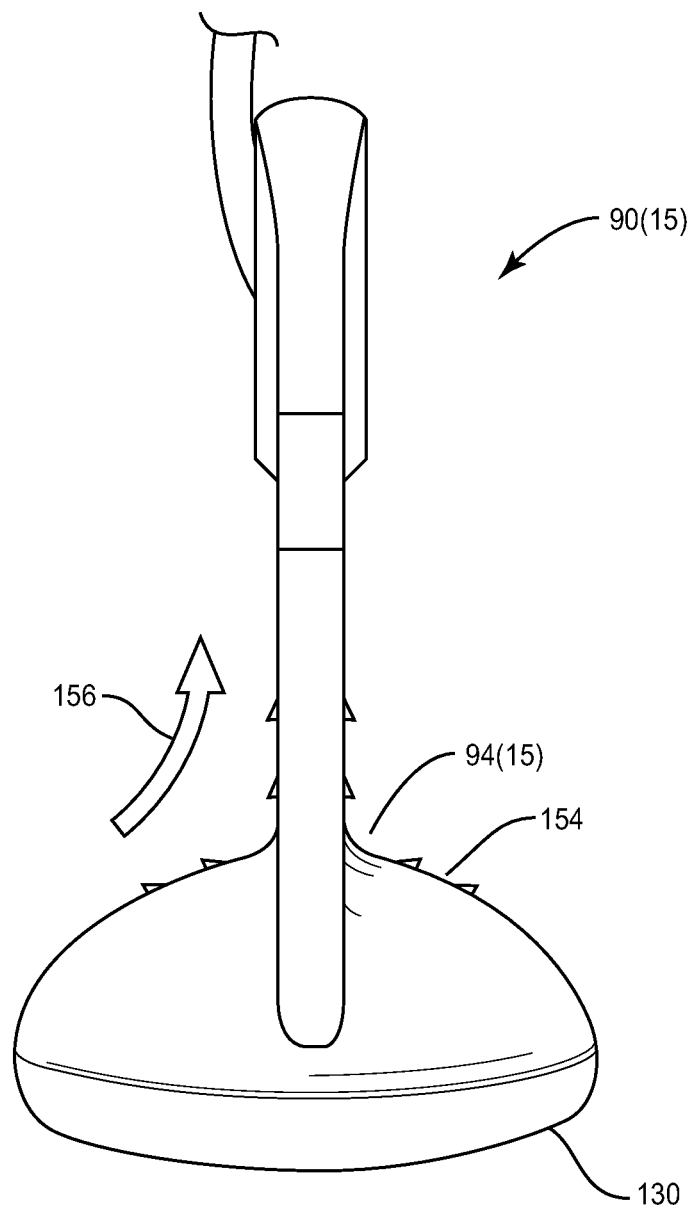
FIG. 22 illustrates an end on view of an eye cup with ramped ridges that provide uni-directional tissue removal forces.

FIG. 22 shows another configuration of a mechanical treatment device 90(15) having an eye cup 130 in another view, to illustrate an embodiment of parallel ridges or lines 154 along eye cup 130 that provide uni-directional mechanical action. The ramped configuration of the ridges 154 create mechanical force only in a central direction or in the direction of the eye lid opening as shown by lines 156, that indicate the direction of tissue removal. Other configurations or directions for the ramped ridges in the mechanical surface 94(15) are possible, such as ridges 154 that are oriented in a direction opposite the direction of the eye lid opening.

Figure 23:
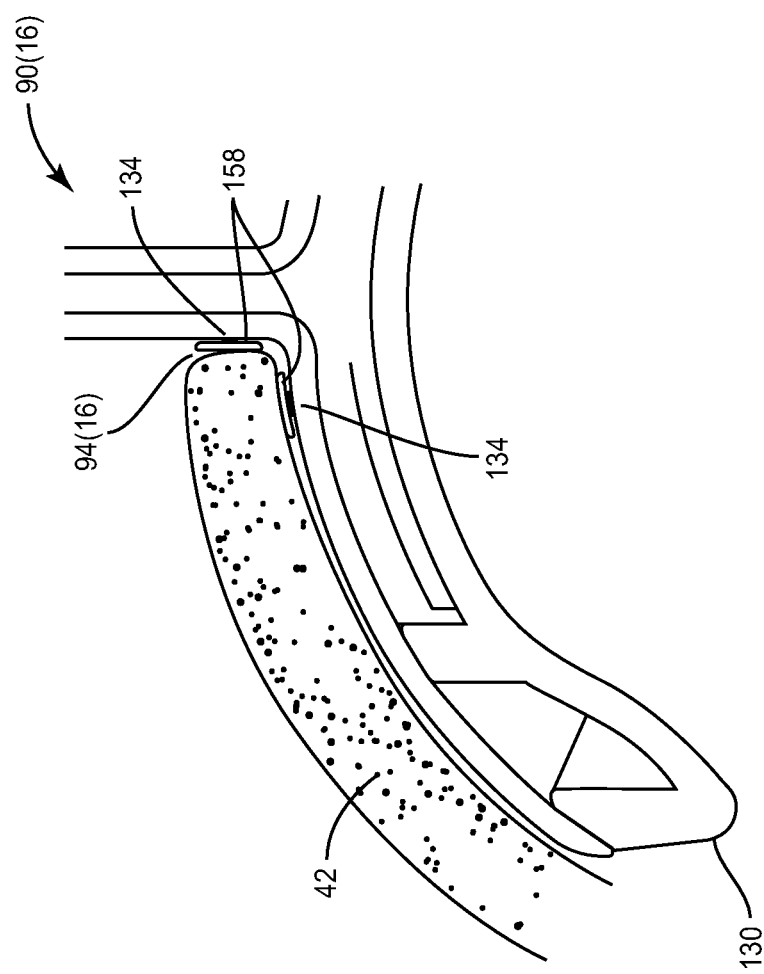
FIG. 23 illustrates a cross sectional view of an eye cup with posts for the placement of inserts with roughened surfaces. These inserts, adhesive strips, or plates can be positioned prior to treatment.

FIG. 23 demonstrates another embodiment of a mechanical treatment device 90(16) having an eye cup 130 that provides the physician the ability to vary the amount of mechanical action provided by mechanical surface 94(16) on the eye lid 42. Depending upon the degree of mechanical action desired, the mechanical surface 94(16) can be altered or selected through the use of inserts, adhesive strips, or plates 158 that can be applied by the physician prior to treatment. FIG. 23 illustrates posts 134 that provide positioning and placement of inserts.

Figure 24:
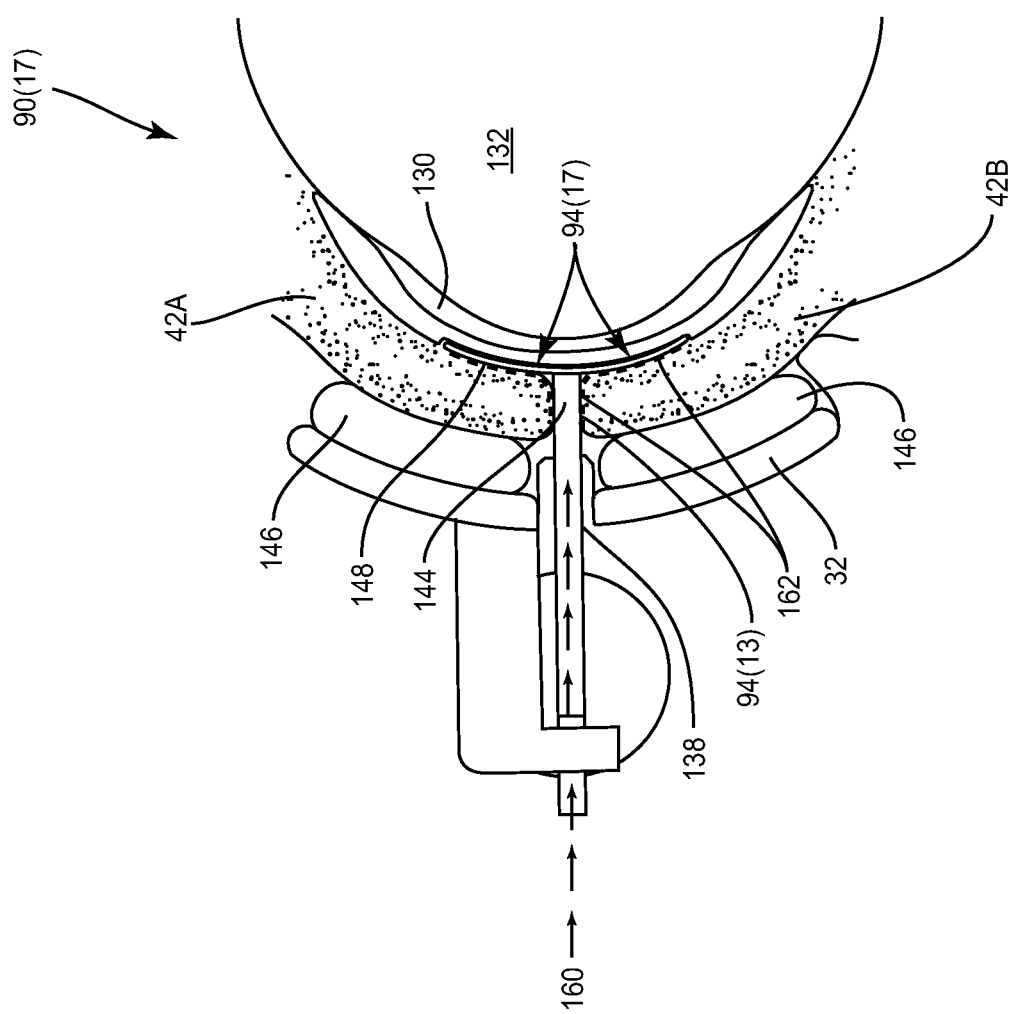
FIG. 24 illustrates a cross sectional view of an eye cup, eye lids, and bladders with an electrical connection to a LipiFlow® generator (not shown) that provides an electrical signal for the creation of the textured mechanical surface zone during a LipiFlow® treatment.

FIG. 24 shows another embodiment of a mechanical treatment device 90(17) having an eye cup 130 that has ridges and roughened surfaces electronically controlled by the LipiFlow® generator (not shown). It may be clinically beneficial to initiate the debridement action on eyelids 42A and 42B following a preheating or preconditioning cycle on the eye lids. Once heated, an electronic signal or electrical power source 160 from LipiFlow® generator (not shown) through shaft 138 activates surface features 162 on mechanical surface 94(17). The change in surface finish can be created through a variety of means. As examples, surface features that can react to electrical power or signals can be resistive elements that expand to create raised surfaces for mechanical action, or the passage of electrical current on nitinol material can create mechanical movement or flexure in response to the electrical current. These flexures, movements, or material expansions can provide an additional sharpened and/or textured mechanical surface for the debridement of tissue on the eye lid.

As discussed above with respect to FIGS. 19A-24, one or more raised areas or surface finishes 142 can be added to existing Meibomian Gland Dysfunction (MGD) treatment devices, such as a LipiFlow® Activator described in U.S. Pat. No. 7,981,146. In one embodiment, a force can be applied to the outside of the eyelid while heat is applied to the inside of the eyelid to treat MGD. The heating of the inner surface of the upper or lower eyelid can be done by any convenient method. The lids can be heated one at a time or both at once, depending on the time available to remove the occlusions once heated. In addition, as discussed above, heating the lid margin prior to applying force to move the eyelid against the raised and/or textured surface has been found to more effectively facilitate removal of devitalized cells than applying force alone. By including one or more raised areas or surface finishes 142 proximate to the lid margin, a device for treating MGD can simultaneously remove devitalized cells from the lid margin of a patient. One device for heating the palpebral conjunctiva is illustrated in FIGS. 25-30.

Figure 25:
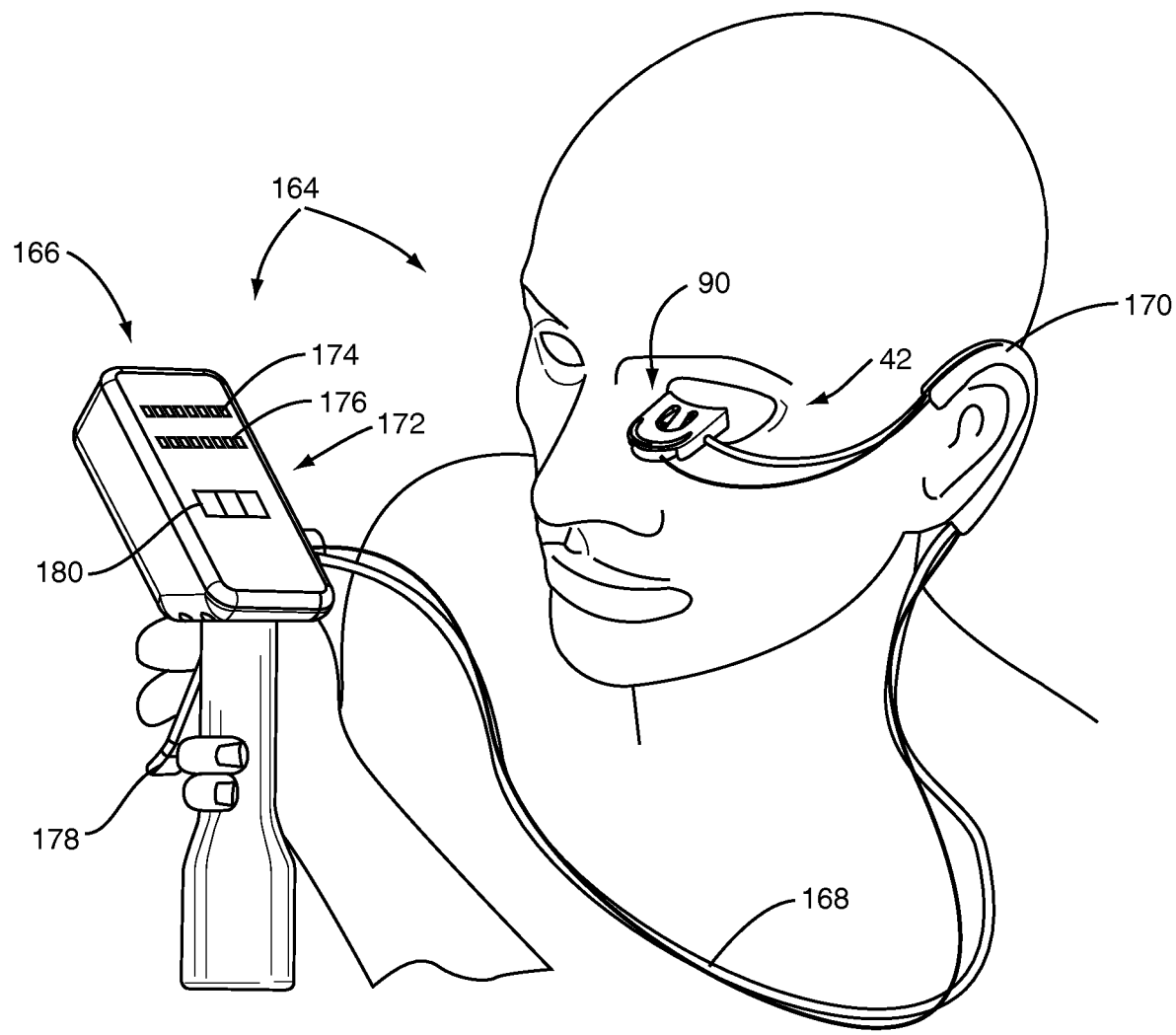
FIG. 25 illustrates a heat and force application device according to one embodiment relating to the present invention to facilitate the application of heat to the inside and force to the outside of a patient's eyelid relating to treating meibomian glands.

FIG. 25 illustrates the overall device referred to as a heat and force application device 164. In this embodiment, the heat and force application device 164 consists of a hand-held, battery-operated controller 166 that contains heat and pressure generating and regulation components. The controller 166 can also be a non hand-held device that is either mounted or rests on a table top, for example. The controller 166 as described herein is intended to describe and encompass any device, including but not limited to electronic and pneumatic controls and supporting components, that is adapted to allow and control the application of heat and/or force to the patient's eyelid. The controller 166 is connected to a disposable component 90, via a controller interface 168, to generate heat and force at an eyelid 42, as illustrated in FIG. 25. The disposable component 90 consists of a lid warmer 90 provided in the form of a lens (illustrated in FIGS. 26-28) that applies heat to the inside of the patent's eyelid and interfaces with an eye cup to apply force to the outside of the patient's eyelid (illustrated in FIGS. 29A, 29B, and 30). Both can be used in concert to treat MGD for a single eye. The interface 168 tubing can be wrapped around the patient's ear 170 with any excess clipped to the patient's clothing. The heat and force application device 164 is intended for use by physicians to apply localized heat and pressure therapy for treating MGD.

The controller 166 contains a user interface 172 to allow a physician or other technician to control the heat and force application device 164. Temperature and pressure being applied to the patient's eyelid 42 can be seen on a temperature display 174 and a pressure display 176. By observing temperature and pressure displays 174, 176, the physician can determine when a therapeutic temperature and pressure have been reached. For example, the temperature and pressure displays 174, 176 may be segment bar graphs so that both the temperature and pressure levels and the increasing or decreasing nature of the temperature and pressure levels can be seen. The temperature level to be reached at the patient's eyelid can either be set to a static level within the controller 166, or controllable by a physician or technician. The force and thus the pressure applied to the patient's eyelid is controllable by squeezing a force lever 178. When a physician or technician desires to apply force, the force lever 178 can be squeezed. To release force and thus reduce pressure, the force lever 178 is disengaged. The pressure created by the force applied to the patient's eyelid is displayed on the pressure display 176.

A timer display 180 can be provided on the controller 166 to display the amount of time that heat and/or force has been applied to the patient's eyelid 42. The timer display 180 can display a cumulative amount of time passed or provide a countdown timer if an initial duration is set. For example, the timer display 180 may be comprised of a number of seven segment displays. In one embodiment, the timer display 180 will count down from one hundred eighty (180) seconds and will flash at one hundred twenty (120) seconds and sixty (60) seconds, which is an indicator to the physician to release the force lever 178 and then reapply force and pressure by squeezing the lever 178 again.

Figure 26:
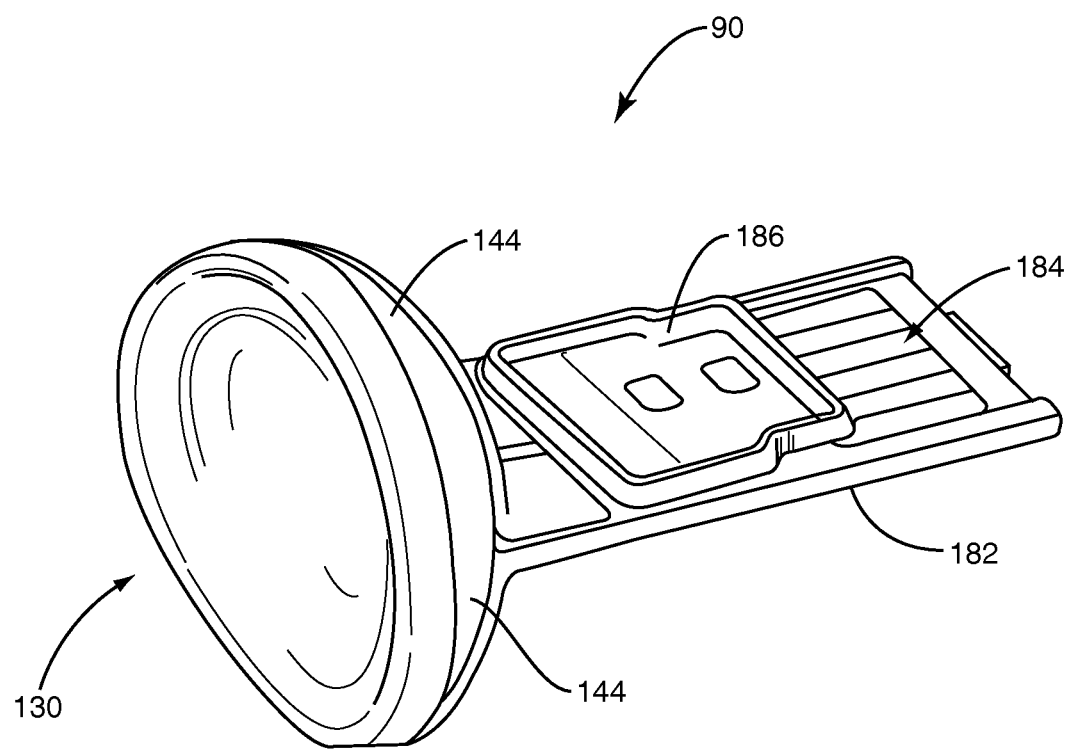
FIG. 26 illustrates a lid warmer component of the heat and force application device illustrated in FIG. 25, which is adapted to fit onto a patient's eye to controllably deliver heat to the inside of the patient's eyelid, according to one embodiment relating to the present invention.
Figure 27:
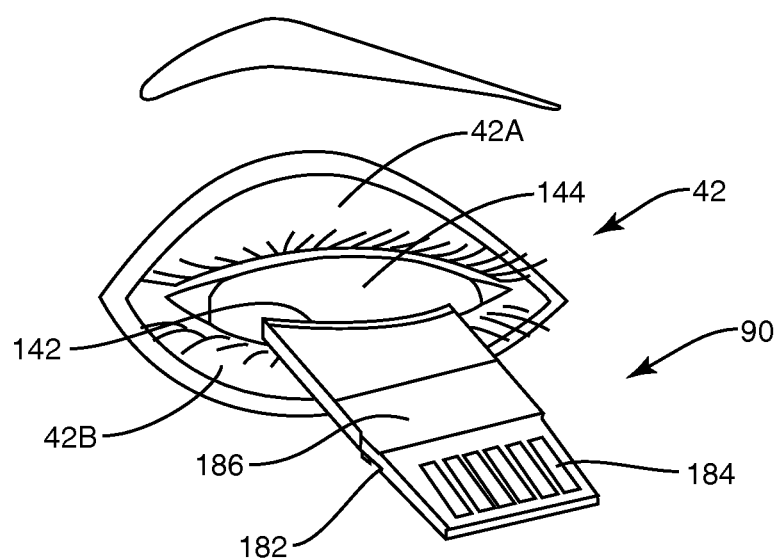
FIG. 27 illustrates the process of placing the lid warmer on the patient's eye inside the eyelid to install the heat application device onto a patient's eye for treating the meibomian glands, according to one embodiment relating to the present invention.

FIG. 26 illustrates the disposable component 90 in more detail. The disposable component 90 consists of a lid warmer 90 that includes a lens in the disclosed embodiment. The lens 130 contains a heating element to apply heat to a patient's eyelids 42A, 42B, but also provides an insulating back plate against which force may be applied. As illustrated in FIG. 27, the lens 130 is placed on the patient's eye with the patient's upper and lower eyelids 42A, 42B resting on the outside surface of the lens 144. Before installation, the scleral side of lens 130 may be lubricated with saline, or equivalent lubricating drops (not shown). The lens 130 is then inserted onto the patient's eye under the eyelids 42A, 42B. A heating element (not shown) is contained within the lens 130 that can apply heat to the inside of the patient's eyelid when installed. The material used to construct the lens 130 is not electrically conductive, but is thermally conductive to allow heat from the heating element inside to be transferred to the patient's eyelid. The lens 130 can be constructed out of a plastic, including a clear plastic such as LEXAN HPS2 for example. Further, the lens 130 can be constructed from a biocompatible material, such as polymethylmethacrylate (PMMA), epoxy, or other materials well known to those skilled in the art. The lens 130 may be flexible, but ideally should be only minimally compressible to fit against the patient's eyeball.

The lens 130 also contains a lid warmer platform or tab 182 that is attached to the lens 130. The lid warmer platform 182 may be connected perpendicularly to the lens 130 such that it extends away from the patient's eye when installed. The lid warmer platform 182 provides several benefits. First, it provides a handle for insertion and movement or adjustment of the lens 130 and its heating element. Second, it provides a guide post for a compression force device to attach to apply a force to the patient's eyelid while the lens 130 applies heat to the inside of the patient's eyelid. The lid warmer platform 182 can also support a lens electrical interface 184 to allow the lens 130 to electrically connect the heating element inside the lens 130 to the controller 166 via the interface 168 (not shown). The controller 166 can then apply electrical energy to the heating element to generate heat within the lens 130 and thus to the inside of the patient's eyelid when installed. It also provides a support structure for interface circuitry 98. The interface circuitry 98 provides electrical connections for energizing the heating element and communicating temperature measured at the lens 130 back to the controller 166 for heat regulation. The interface circuitry 98 will discussed later in this application and in regard to FIG. 32.

Figure 28:
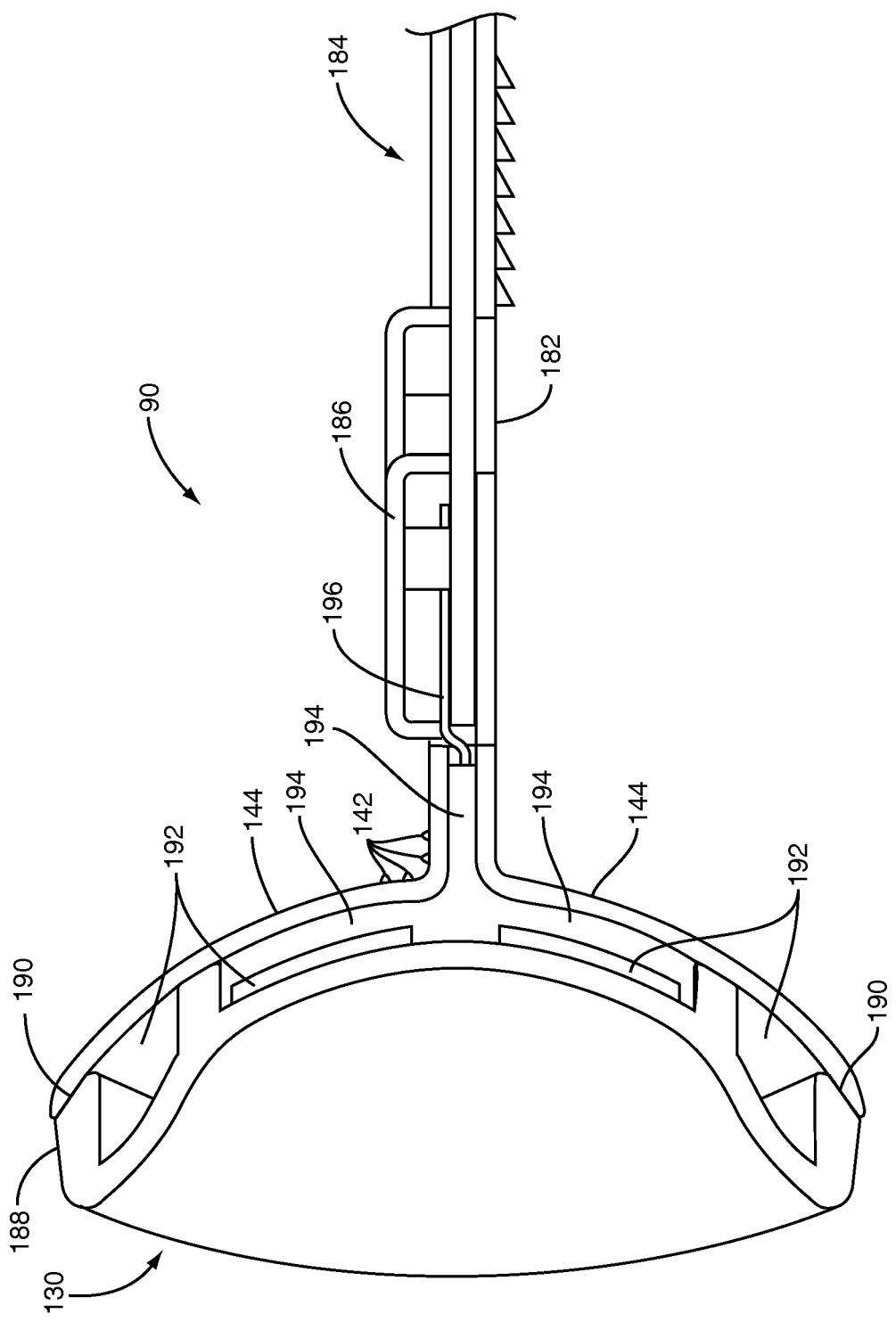
FIG. 28 illustrates a cross-sectional view of the lid warmer illustrated in FIG. 26 to further illustrate heat delivery components and features of the lid warmer, according to one embodiment relating to the present invention.

FIG. 28 illustrates a cross-sectional view of the lid warmer employing the lens 130 illustrated in FIGS. 25-27, to further illustrate heat delivery components and features of the lid warmer in combination with raised areas 142, similar to the raised areas 142 described above with respect to FIGS. 19A-C for removing devitalized cells from the lid margin, according to one embodiment of the present invention. The lens 130 is formed by a scleral side 93 being attached to an eyelid side 92. The scleral side 93 of the lens 130 contains a bend 188 around its circumference edge to provide an attachment edge 190 to support attachment of the eyelid side 92. Because of the bend 188, a hollow chambers 192 are formed inside the lens 130. The hollow chamber 192 supports a heating element 194 contained inside the lens 130 to generate heat when energized. The heating element 194 abuts against the eyelid side 92 of the lens 130 so that the heat generated is located adjacent the inner eyelid to apply heat to the meibomian glands. The heating element 194 is attached to the interface circuitry 98 via a fused link 196, which is then attached to the controller 166 via the lid warmer platform 182 being attached to the controller interface 168 (not shown). In this manner, the controller 166 can cause the heating element 194 inside the lens 130 to generate heat by applying an electrical signal to the interface circuitry 98, which is connected to the heating element 194. If the temperature exceeds the threshold temperature level of the fused link 196, the link 196 would melt and create an open circuit to disable the heating element 194 for safety reasons. Alternatively, the fused link 196 could be a thermal link provided as an integrated part of the heating element such that the fused link 196 would melt and create an open circuit at a given threshold temperature.

The heating element 194 may be provided in any form or material. The heating element 194 may be a resistive type heater, a thick film heater, or any one of a number of other types, such as a "flex circuit" (etched metal on flexible substrate) well known to those skilled in the art. The heating element 194 can be formed to the shape of the lens 130. In the illustrated example, the heating element 194 is a material that is both electrically and thermally conductive. This may be important, as the electrical conductivity characteristic allows current to be applied to the heating element 194 to generate resistive heat. The thermal conductivity characteristic serves to evenly distribute the resistive heat over the entire heating element 194 and thus distributes the heat to the patient's eyelid more evenly. Without these characteristics, it may be more difficult to regulate heat generated by the heating element to efficiently and effectively melt, loosen, or soften obstructions or occlusions in the meibomian glands. Examples include the E5101 carbon-loaded polyphenylene sulfide and the E2 liquid crystal polymer, both manufactured by Cool Polymers, Inc.

The size of the lens 130 may also play a part in the heating element 194 selection and the amount of heat it must generate to be effective in MGD treatment. The lens 130 distributes heat generated by the heating element 194. A larger lens 130 may distribute the heat generated by the heating element 194 more uniformly and over a larger surface area. Also note that the application of heat to the patient's eyelid does not necessarily have to include an embedded heating element 194 in the lens 130. Heat application may be provided as part of the environment, such as air for example. The amount of heat applied, the temperature reached at the meibomian glands as a result, where the heat is applied on the patient's eyelid or surrounding tissue, and the duration of heat applied can control the selection of the heating source.

In addition to the insulation provided by the material used to construct the lens 130, the lens 130 may also contain an integrated insulator inside the chamber 192 as an additional measure of insulation. Insulation prevents substantial heat from reaching the eyeball and thus protects the cornea and sclera. As employed herein, the term "insulate" or "insulation" is intended to include any component or material and/or specific geometries of components or materials, wherein there is greater resistance to thermal conduction or radiation towards the surface of the eye than towards the eyelid. Stated alternatively, in the insulator, thermal energy radiates more easily towards the eyelid 42A, 42B than towards the eyeball surface in order to minimize the possibility of causing injury to the eyeball. In the lens 130 example of FIG. 28, the integrated insulator is air and is formed by the natural gap that exists by the space left by the heating element 194 not filling up the entire volume of the chamber 192. The heating element 194 is biased according to its location in the lens 130, and in particular to be located behind the integrated insulator, to produce more heat on the inside of the patient's eyelids than on their eyeball.

Figure 29A:
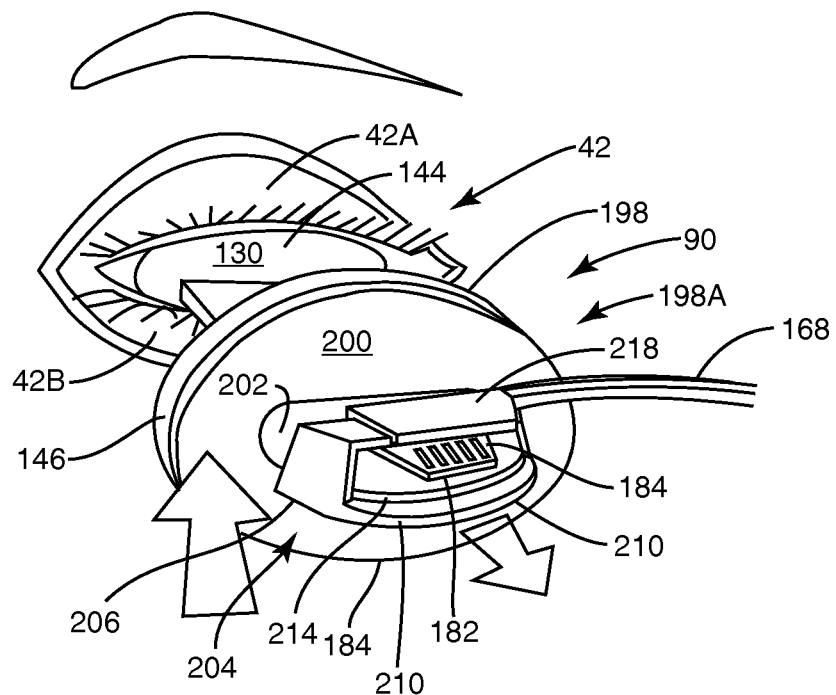
FIGS. 29A and 29B illustrate embodiments of a lid warmer and eyecup heat and force application device for securing the eyecup to the lid warmer as part of installing the force application device onto a patient's eye for treating the meibomian glands.

FIG. 29A illustrates an eyecup 198 that is adapted to allow the controller 166 to apply a force and/or heat to the patient's eyelids 42A, 42B. The eyecup 198 is a curved carrier 206 that supports an inflatable bladder 146. The inflatable bladder 146 is attached to the curved carrier 206. The inflatable bladder 146 is then connected to the controller 166 via a tubing 208 in the controller interface 168 (see FIG. 30) such that the controller 166 can pump air into the tubing 208 to inflate the inflatable bladder 146. When inflated, the eyecup 198 applies force to the outside of the eyelid 42A, 42B while heat can be applied via the lens 130 and heating element 194. To apply force to the patient's eyelids 42A, 42B, the bladder 146 is inflated under control of the controller 166. To release the force and thus reduce pressure, the air in the bladder 146 is released by the controller 166.

When desired to be used, the lid warmer platform 182 is inserted into an eyecup orifice or slot 202 in the eyecup 198 between a latching mechanism 204. The latching mechanism 204 provides a means to secure the lid warmer platform 182 to the eyecup 198 when in use, as well as to provide an interface to electrically connect the lid warmer electrical interface 184 to the controller 166 via the controller interface 168. The latching mechanism 204 is comprised of a carrier 206 having a semi-circular carrier base 210. The carrier base 210 receives an eyecup platform 214 attached to the eyecup 198. The carrier base 210 and eyecup platform 214 can be squeezed together like a clip to control an opening through which the lid warmer platform 182 is inserted into the carrier 206 when inserted into the orifice 202 of the eyecup 198. When the carrier base 210 is not squeezed against the eyecup platform 214, the carrier opening through which the lid warmer platform 182 is inserted closes to secure the lid warmer platform 182 to the carrier 206, and thus the eyecup 198. The eyecup platform 210 is adapted to allow the lid warmer platform 182 to rest on top when inserted into the eyecup orifice 202. When inserted, the electrical interface 184 of the lid warmer 74 contacts a carrier interface 123 (not shown), which provides an electrical connection between the electrical interface 184 and the controller interface 168.

Figure 29B:
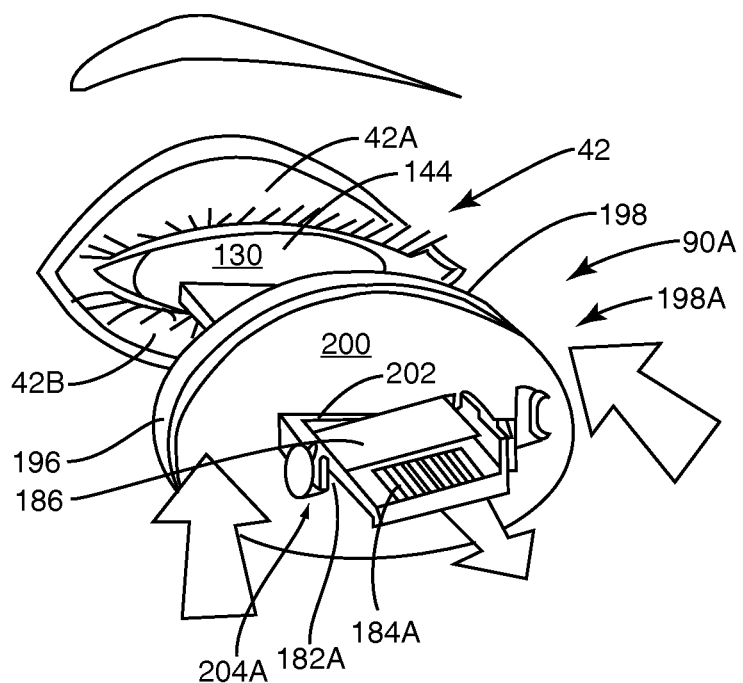

FIG. 29B illustrates an alternative latching mechanism 204A to one illustrated in FIG. 29A. The latching mechanism 204A is compressed in the horizontal plane while the eyecup 198 is moved forward along the lid warmer tab 182A until it rests against the outside of the patient's eyelids 42A, 42B. When the latching mechanism 204A is released, the eyecup 198 is fixed in place in its location along the lid warmer tab 182A. In this manner, the patient's eyelids 42A, 42B are "sandwiched" between the lens 130 and the eyecup 198.

Figure 30:
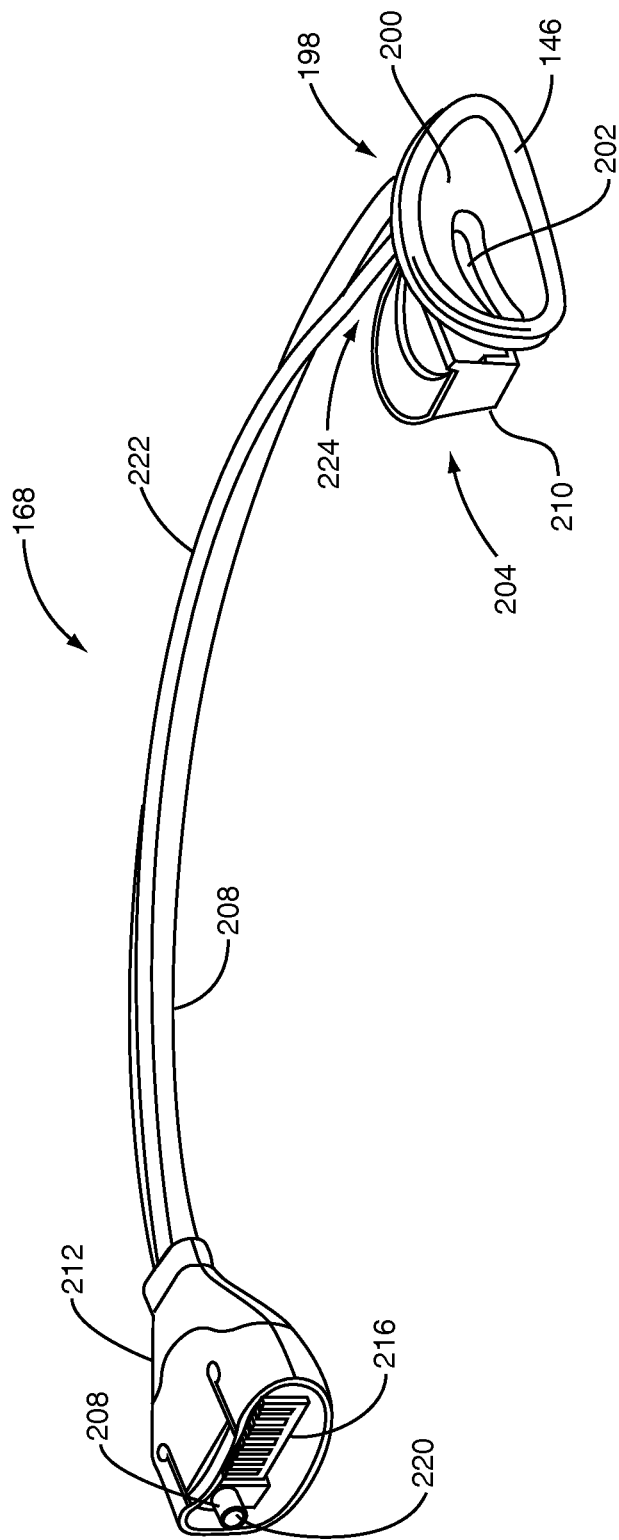
FIG. 30 illustrates an interface adapted to be attached between the eyecup and the controller of FIGS. 9-13B for facilitating selective and controllable communication of heat and/or force to the eyelid, according to one embodiment of the present invention.

FIG. 30 illustrates more detail regarding the controller interface 168. The controller interface 168 couples the controller 166 to the lens 130 and eyecup 198 to allow the controller 166 to controllably apply heat and/or force to the patient's eyelid as part of a MGD treatment. The controller interface 168 contains a connector 212 on one end that connects to the controller 166. The connector 212 includes both an electrical interface 216 and a pneumatic interface 220. The electrical interface 216 allows the controller 166 to send and receive electrical signals over an electronics wiring 222 to and from the lid warmer 90, as will be described in more detail below. The electronics wiring 222 interfaces with an eyecup electrical connector 224 on the eyecup 198 such that the lid warmer electrical interface 184 of the lid warmer 90 is connected to the electronics wiring 222 when the lid warmer platform 182 is inserted into the eyecup 198, as illustrated in the examples of FIGS. 29A and 29B. The pneumatic interface 220 allows the controller 166 to pump into the tubing 208 to inflate the inflatable bladder 146 on the eyecup 198 to apply force to the patient's eye and to deflate the air in the inflatable bladder 146 to release force and relieve pressure. In the illustrated embodiment, the pneumatic interface 220 is securely coupled to the inflatable bladder 146 on the eyecup 198.

Figure 31:
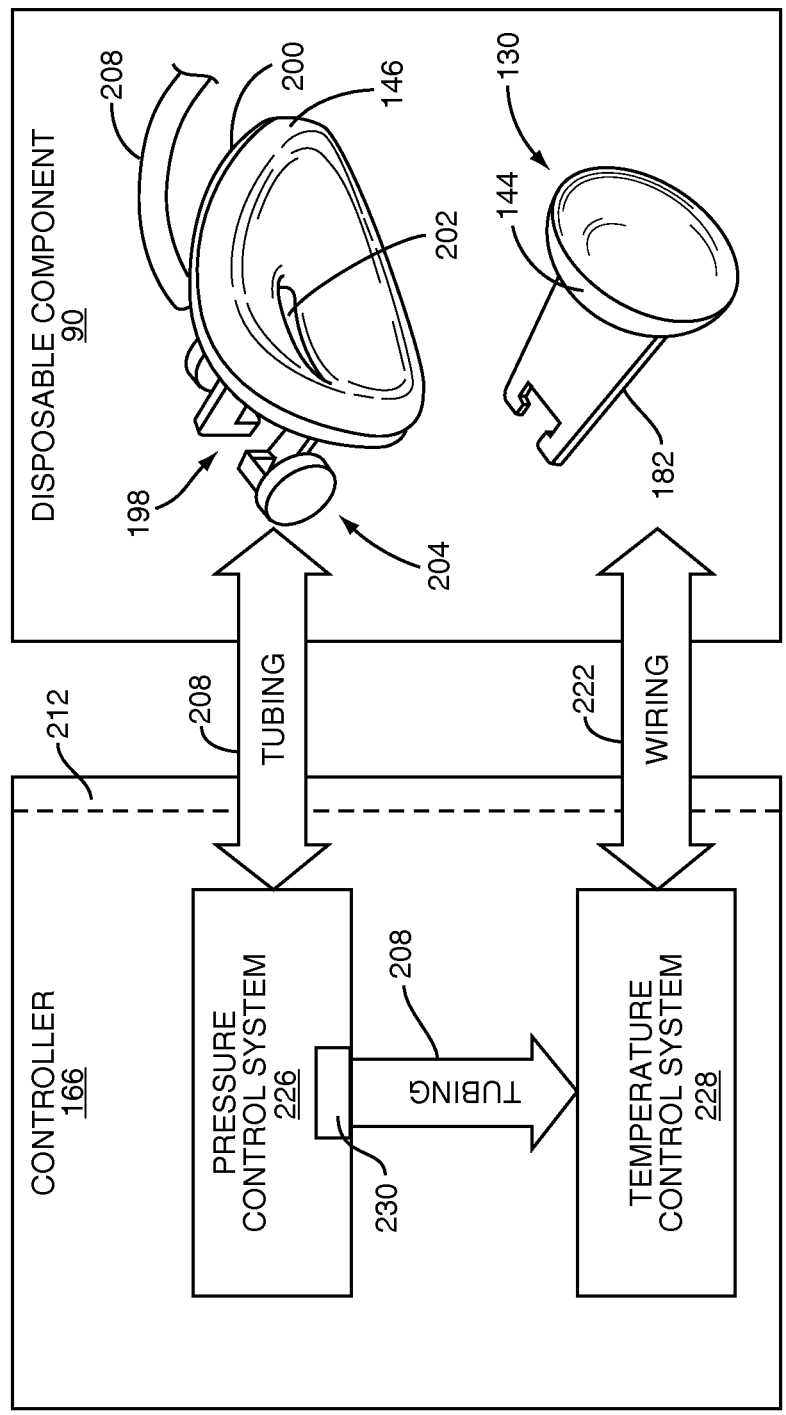
FIG. 31 illustrates a top level system diagram of the temperature and pressure control and communication components of the heat and force application device for selectively and controllably communicating to the lid warmer and eyecup components to apply heat to the inside of a patient's eyelid and/or force to the outside of the patient's eyelid, according to one embodiment relating to the present invention.

FIG. 31 supplements FIG. 30 to illustrate the interface components between the controller 166 and the disposable component 90 and the eyecup 198, at a system level. The controller 166 of the heat and force application device 164 contains a pressure control system 226 and a temperature control system 228. The pressure control system 226 is the control component within the controller 166 that controls the pressure from the force applied to the patient's eye via the eyecup 198. The temperature control system 228 is the control component within the controller 166 that controls the heat applied to the patient's eye via the lid warmer 90. The pressure control system 226 also communicates the pressure in the tubing 208 to a pressure sensor 230 within the pressure control system 226. The pressure sensor 230 is used to determine the pressure level in the tubing 208 to display the pressure on the pressure display 176 as well as to provide feedback to the controller 166 to provide the various functions and controls for the system, as will be described in more detail below. The pressure sensor 230 also allows the recordation of pressure data to be recorded by the controller 166, or an external data acquisition device (not shown) coupled to the controller 166, if desired.

FIG. 31 also illustrates more detail regarding the latching mechanism 204 on the eyecup 130. The latching mechanism 204 facilitates providing a connection between the lid warmer 90 and the lid warmer platform 182 and the eyecup 198, and the lid warmer 90 to the electronics wiring 222 when the eyecup orifice 202 is slipped over to the lens platform 182 to secure the eyecup 198 to the patient's eyelid. Two different types of latching mechanism 204, 116A were previously illustrated in FIGS. 29A and 29B, either of which can be used to secure the platform 182 to the eyecup 198, or any other type may be used.

Figure 32:
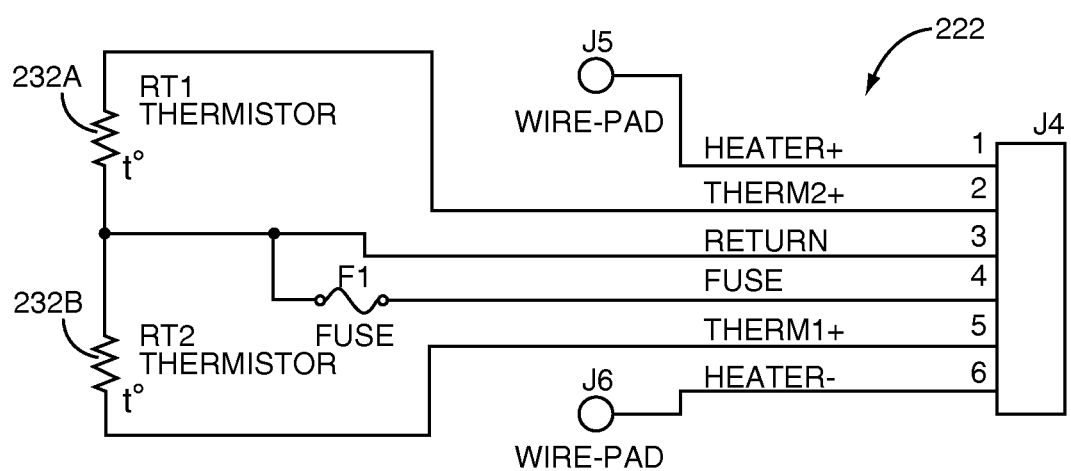
FIG. 32 illustrates an interface circuit diagram for the heating and force application device, according to one embodiment relating to the present invention.

FIG. 32 illustrates the specific wiring and supporting circuitry that comprises the electronics wiring 222 to interface the controller 166, and particularly the temperature control system 228, to the lid warmer 90 to apply heat to the patient's eye for the disclosed embodiment. Six wires make up the electronics wiring 222. The six interface wires are connected to the interface circuitry 98 that is embedded in the disposable component 90. HEATER+ and HEATER− are connected to the heating element 194 in the lid warmer 90 when the platform 182 is connected to the controller interface 168. THERM1+ and THERM2+ are coupled to two thermistors 232A, 232B. The two thermistors 232A, 232B provide an indication of temperature at the patient's eyelid as part of a temperature feedback mechanism to allow the temperature control system 228 to monitor the temperature for control. Because in the preferred embodiment, the temperature drop between the heating element 194 and the inside of the patient's eyelid is minimal, regulating temperature is simpler. This is because the thermistors 232A, 232B record temperatures closer to the actual temperatures at the glands and thus temperature overshooting is minimized. It is important to attempt to minimize temperature overshoot so as to not damage the patient's tissue. Temperature thermostats or other more complicated regulation circuits may be employed to regulate temperature as well if desired, especially if temperature overshooting is an issue. Further, the size of the heating element and power supply could also be selected so that only a known maximum amount of heat could be generated even if the heating element 194 were energized all the time. This would avoid use of a regulation circuit to prevent temperature overshoot.

Two thermistors 232A, 232B are provided for redundancy and error checking in the event one fails. Both thermistors 232A, 232B should provide the same signal indicative of temperature. Both thermistors are coupled to a common RETURN to provide common current return/grounding. Lastly, a FUSE line is provided and linked to a fuse 234, which is also coupled to the RETURN line. As will be discussed later in this application, the controller 166 can send a current over the FUSE line sufficient to blow fuse 234. The controller 166 can blow the fuse 234 to provide an indication that the lid warmer 90 has been previously used. Thus, if the lid warmer 90 is reused, the controller 166 can detect the open circuit on the FUSE line and know that the fuse 234 has been previously blown.

Figure 33:
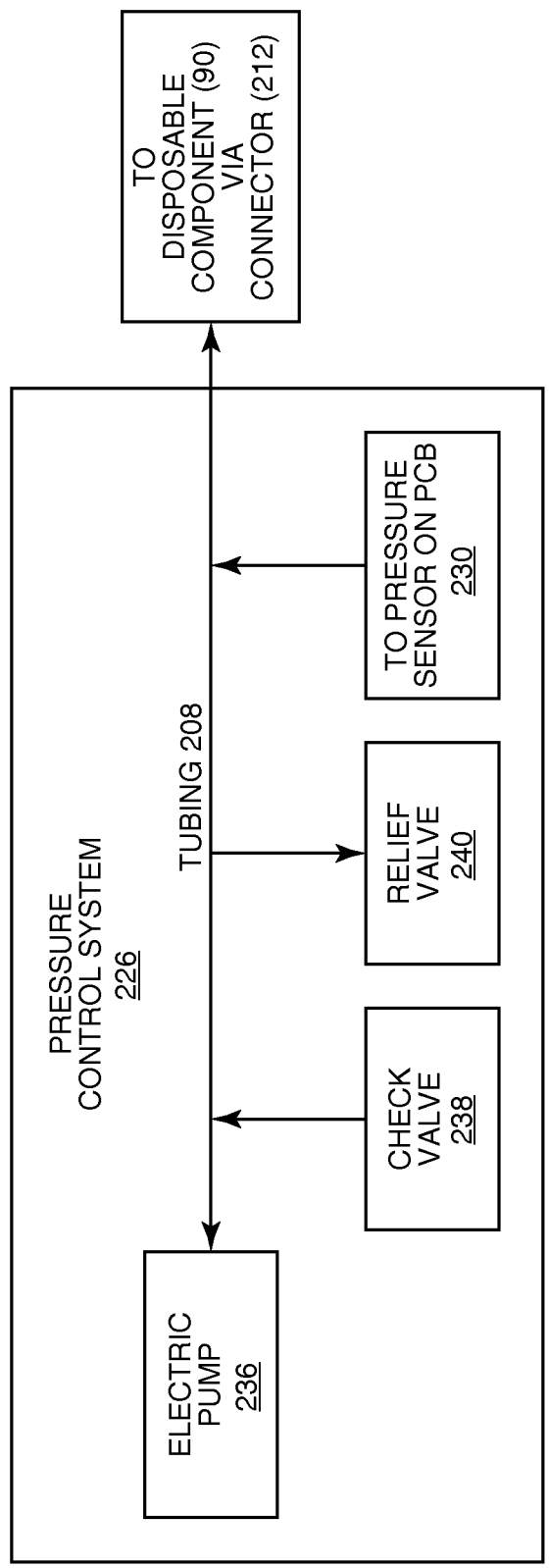
FIG. 33 illustrates a pressure control system for the heating and force application device to selectively and controllably apply force to the outside of a patient's eyelid, according to one embodiment relating to the present invention.

FIG. 33 illustrates additional components of the pressure control system 226 to provide more detail for the disclosed embodiment. The pressure control system 226 contains an electric pump 236 to pump air into the tubing 208. Other types of pumps may be used. A check valve 238 is provided inline in the tubing 208 between the electric pump 236 and the inflatable bladder 146 to allow the controller 166 to draw in air to the system to use to inflate the inflatable bladder 146 without backflow release. A relief valve 240 is also provided as a safety measure to ensure that line pressure to the eyecup 198 does not exceed maximum pressure settings in the controller 166. As illustrated in FIG. 31 and discussed above, the pressure sensor 230 is coupled to the tubing 208 to communicate the pressure in the tubing 208 to the pressure control system 226 for various functions.

Figure 34:
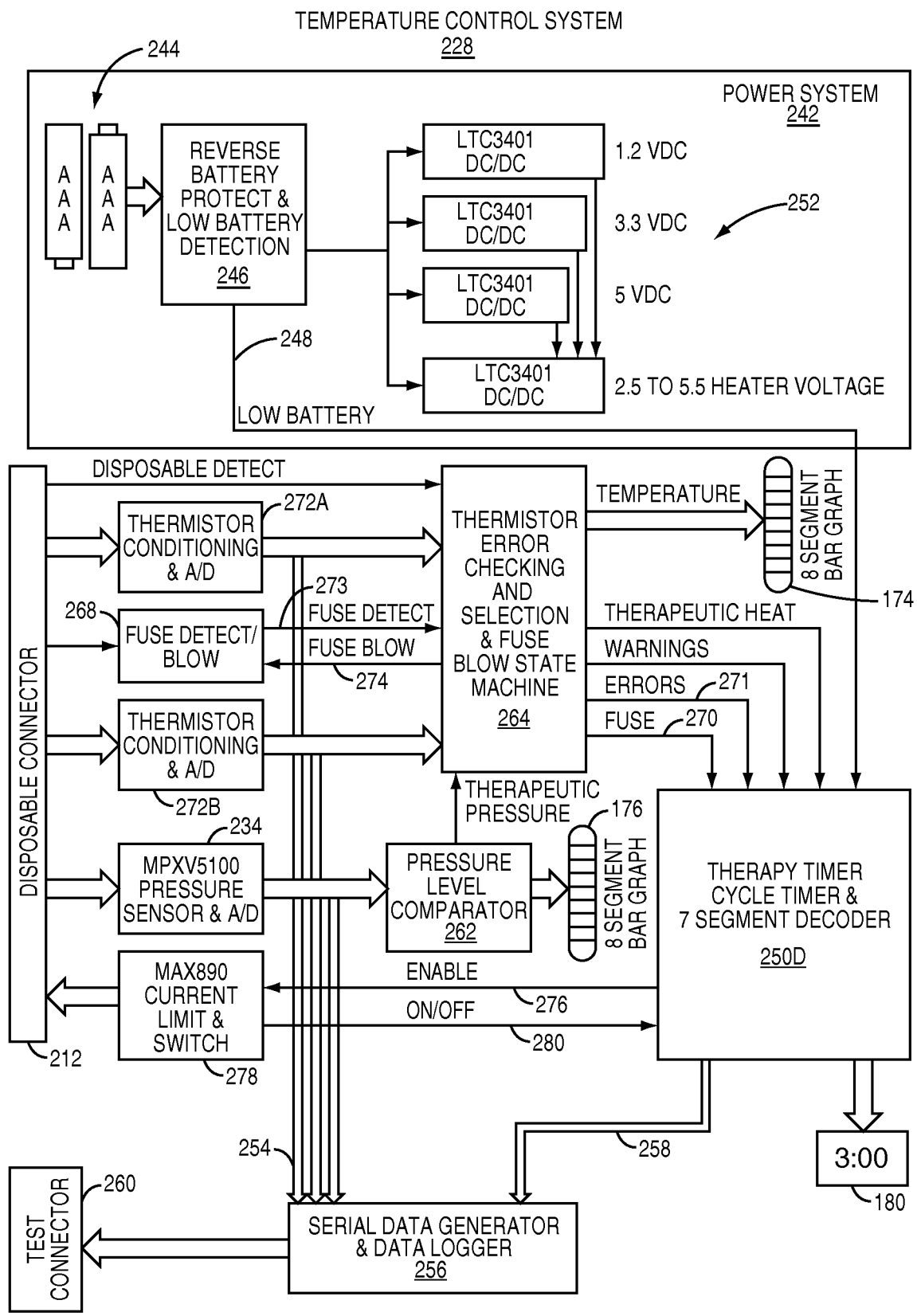
FIG. 34 illustrates a temperature control system for the heating and force application device to selectively and controllably apply heat to the inside of a patient's eyelid, according to one embodiment relating to the present invention.

FIG. 34 illustrates the temperature control system 228 in more detail for the preferred embodiment. The temperature control system 228 includes a power system 242 to provide power to the system components. In the disclosed embodiment, batteries 244 are used as the power supply. Energy from the batteries 244 are provided to a reverse battery protection and low battery detection circuit 246. If the batteries 244 are low in power, a low battery signal is communicated over a low battery signal line 248 to a timer and display controller 250D. The timer and display controller 250D is responsible for controlling therapy timers and displaying them on the timer display 180. The timer and display controller 250D is also used to communicate other codes to the user regarding the controller 166, including the low battery signal. The energy from the batteries 244 is also routed to various DC-DC converters 252 to provide various voltage levels needed by the controller 166 and its components for operation. Note that the present invention is not limited to any particular type of power system or specific power components.

The temperature control system 228 may also contain a data interface 254 to provide pressure and temperature data to a data logger 256. The data logger 256 may also contain a timer interface 258 for the timer and display controller 250D so that times can be recorded for the data. The data logger 256 may be used to record data regarding patient treatments for analysis and/or to provide data for test purposes. The data logger 256 may be coupled to a test connector 260 so that logged data regarding the system may be viewed and/or recorded via an external device (not shown) coupled to the test connector 260.

The remainder of the temperature control system 228 consists of various components of the controller 166 that provide the overall operation and control of the heat and force application device 164. These components are provided in the form of various circuits and control components, including programmable gate arrays (PGA). The components interact together to provide a system logic for operation of the system. These components will be described in conjunction with FIGS. 37-42 below, which describe the logic control of the system. Note that these components can be provided by either analog or digital circuitry, and can be provided using a microprocessor-based architecting, including software, if desired.

Figure 35:
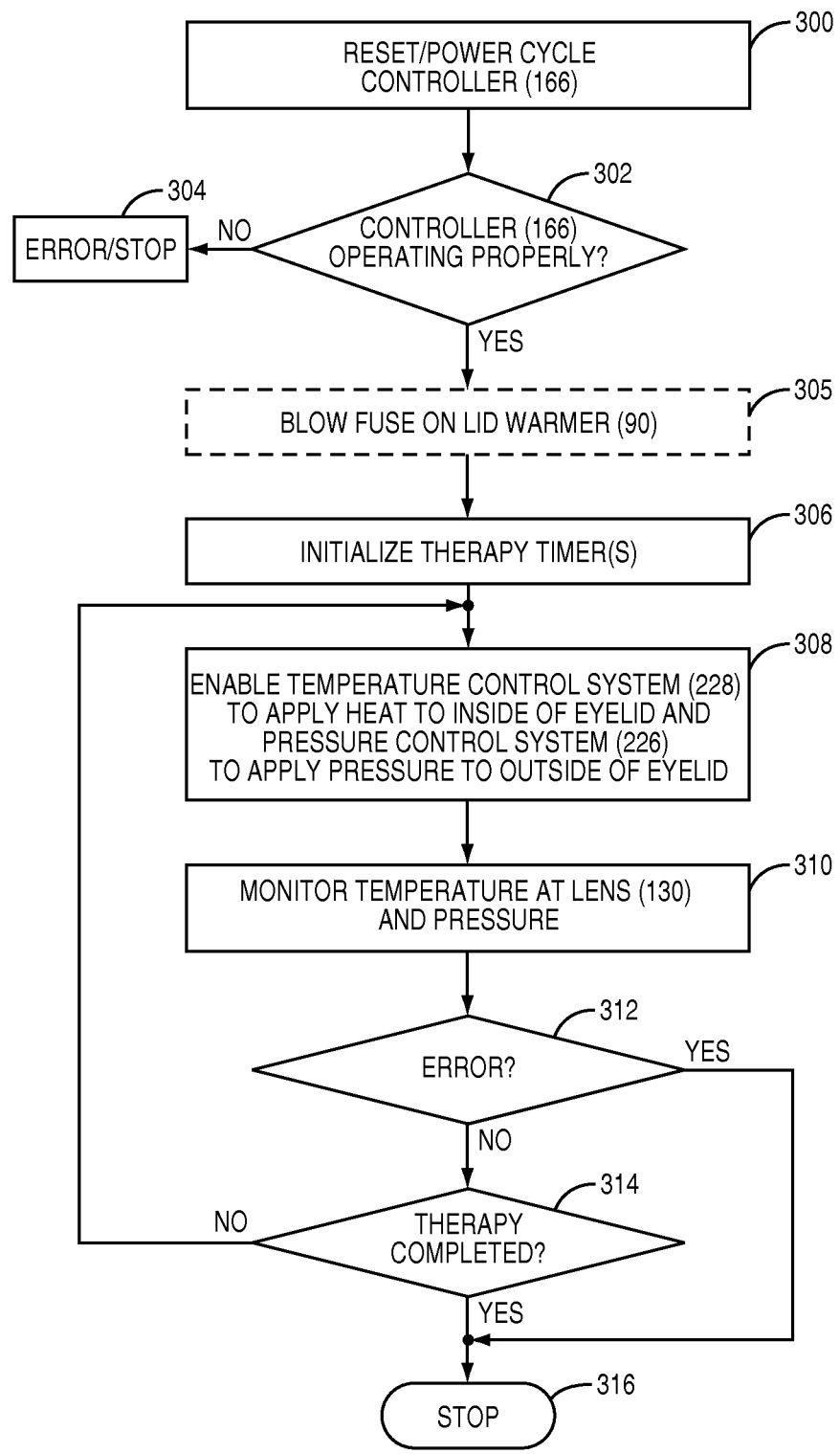
FIG. 35 is a flowchart illustrating the basic process employed by the heat and force application device to selectively and controllably apply heat to the inside of a patient's eyelid and/or force to the outside of the patient's eyelid, according to one embodiment relating to the present invention.

FIGS. 37A-42 illustrate the state machine of the controller 166 and the various operations performed in the states that provide the operation and logic of the heat and force application device 164. However, before turning the state machines and the logic of the various states, a high level overall operation of the controller 166 is described with respect to the flowchart of FIG. 35. FIG. 35 will be discussed in conjunction with the various states that make up the state machine of the controller 166 illustrated in FIG. 35.

FIG. 35 illustrates a flowchart which describes the overall operation and logic of the heat and force application device 164 that is carried out by the controller 166 and its systems, including the pressure control system 226 and the temperature control system 228, according to an embodiment of the present invention. The process starts by the controller 166 resetting in the reset state (step 300 in FIG. 35, reset state 320 in FIG. 36). The controller 166 always starts in a reset state in the disclosed embodiment. The reset state may occur as a result of a power cycle or if a new disposable component 90 is connected to the controller 166. After resetting, the controller 166 performs a series of tests prior to beginning treatment to determine if the controller 166 and its components are operating properly (decision 302 in FIG. 35). If not, an error is noted and the controller 166 stops operation by entering into the stop state (step 304 in FIG. 35, stop state 324 in FIG. 36). The stop state disables the heater. If the controller 166 is operating properly (decision 302 in FIG. 35), the controller 166 proceeds with the operations to begin a treatment by entering the run and monitor states (states 326 and 328 in FIG. 36).

Figure 36:
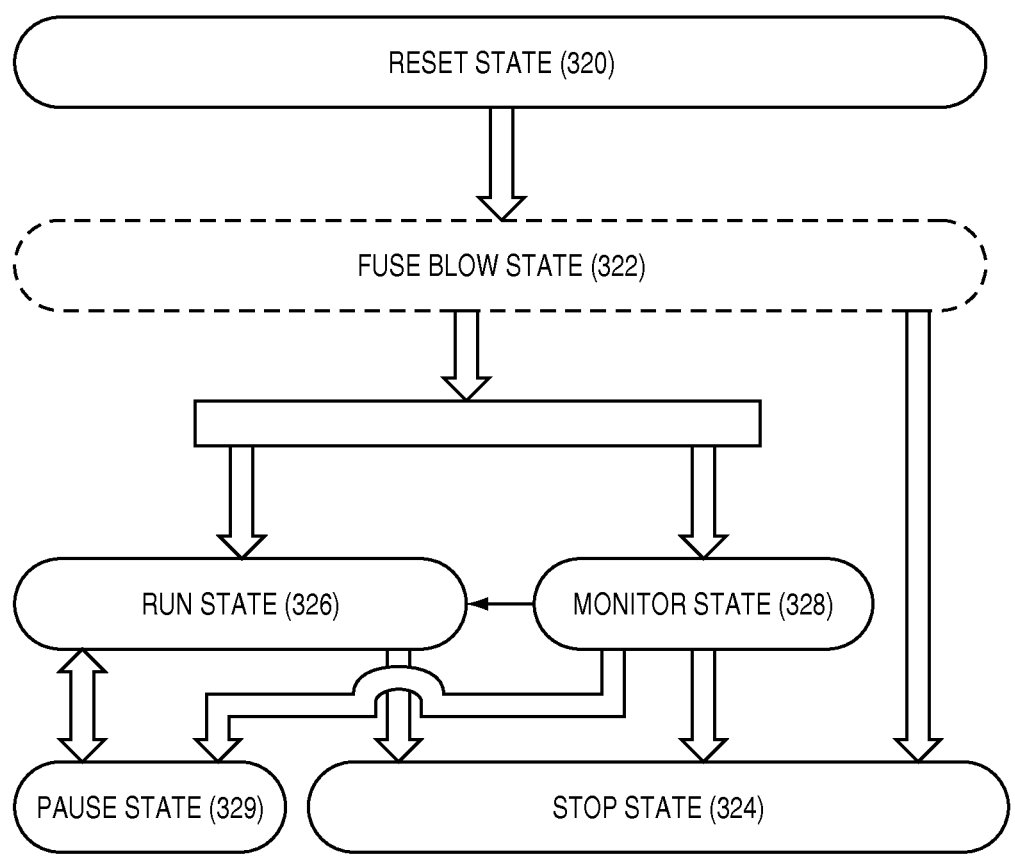
FIG. 36 illustrates a system state flow diagram for the heating and force application device, according to one embodiment relating to the present invention.

As an option, the controller 166 may first blow a fuse on the lid warmer 90 to create an open circuit in a fuse blow state (step 305 in FIG. 35, fuse blow state 322 in FIG. 36). This is so a lid warmer 90 cannot be reused for subsequent treatments for safety and contamination reasons. As part of the operation check in decision 302, the controller 166 may determine if the fuse on the lid warmer 90 has been blown in the reset state (320 in FIG. 36). If so, this would be an indication that the lid warmer 90 has already been used, and the controller 166 would enter the stop state (step 304 in FIG. 35, stop state 324 in FIG. 36). The controller 166 will continue to allow operation with the installed lid warmer 130 after the fuse is blown until the lid warmer 90 is removed. In such case, the controller 166 will enter the reset state (step 300 in FIG. 35, reset state 320 in FIG. 36).

Next, the controller 166 prepares for a therapy. The controller 166 may first initialize therapy timers in the timer and display controller 250 (step 306 in FIG. 35). Timers allow the user of the controller 166 to track the amount of time that therapy has occurred, including heat and force application. Different patients may require different amounts of time for the application of heat and force during treatments. For example, a treatment cycle may include the application of heat for three minutes, but force may need to be applied, disengaged, and reapplied several times during the three minute therapy time period.

Subsequently, the controller 166 enables the temperature control system 228 and the pressure control system 226 to apply heat and force to the patient's eyelid as part of a run state (step 308 in FIG. 35, run state 326 in FIG. 36). In the disclosed embodiment of the lid warmer 90 and eyecup 198, heat is applied to the inside of the patient's eyelid, and force is applied to the outside of the patient's eyelid, as previously discussed. However, note that the controller 166 could also be used to apply heat and/or force to any part of the patient's eye or supporting structure, including but not limited to both to the outside of the patient's eyelid, and heat to the outside and force to the inside of the patient's eyelid. The controller 166 then monitors the temperature and force applied to the patient's eyelid as part of the heat and pressure regulation in a monitor state (step 310 in FIG. 35, monitor state 328 in FIG. 36). The run and monitor states 326, 328 operate simultaneously in the preferred embodiment so that heat and force are constantly being applied and temperature and pressure monitored during therapy. If during the run or monitor 326, 328, an error is detected (decision 312 in FIG. 35), the controller 166 enters the stop state to discontinue therapy (step 316 in FIG. 35, stop state 324 in FIG. 36). If an error is not detected, the run and monitor states 326, 328 continue until either an error is detected (decision 312 in FIG. 35) or the therapy is completed (decision 314 in FIG. 35).

FIGS. 37A-42 illustrate flowcharts that detail the operation of the various states executed by the controller 166 to control temperature and pressure to provide MGD treatment, according to the disclosed embodiment. Each of these states were described generally above with respect to the flowchart in FIG. 35 and the state diagram in FIG. 36. Now, each state and their specific operations and functionalities as it contributes towards the operation of the heat and force application device 164 and its controller 166 will be described in more detail. Since some operations require information from various components in the pressure and temperature control systems 226, 228, references to these various components will be made as the operations of the states are described. This includes reference to components previously and not previously introduced in the temperature control system 228 in FIG. 34.

Figure 37A:
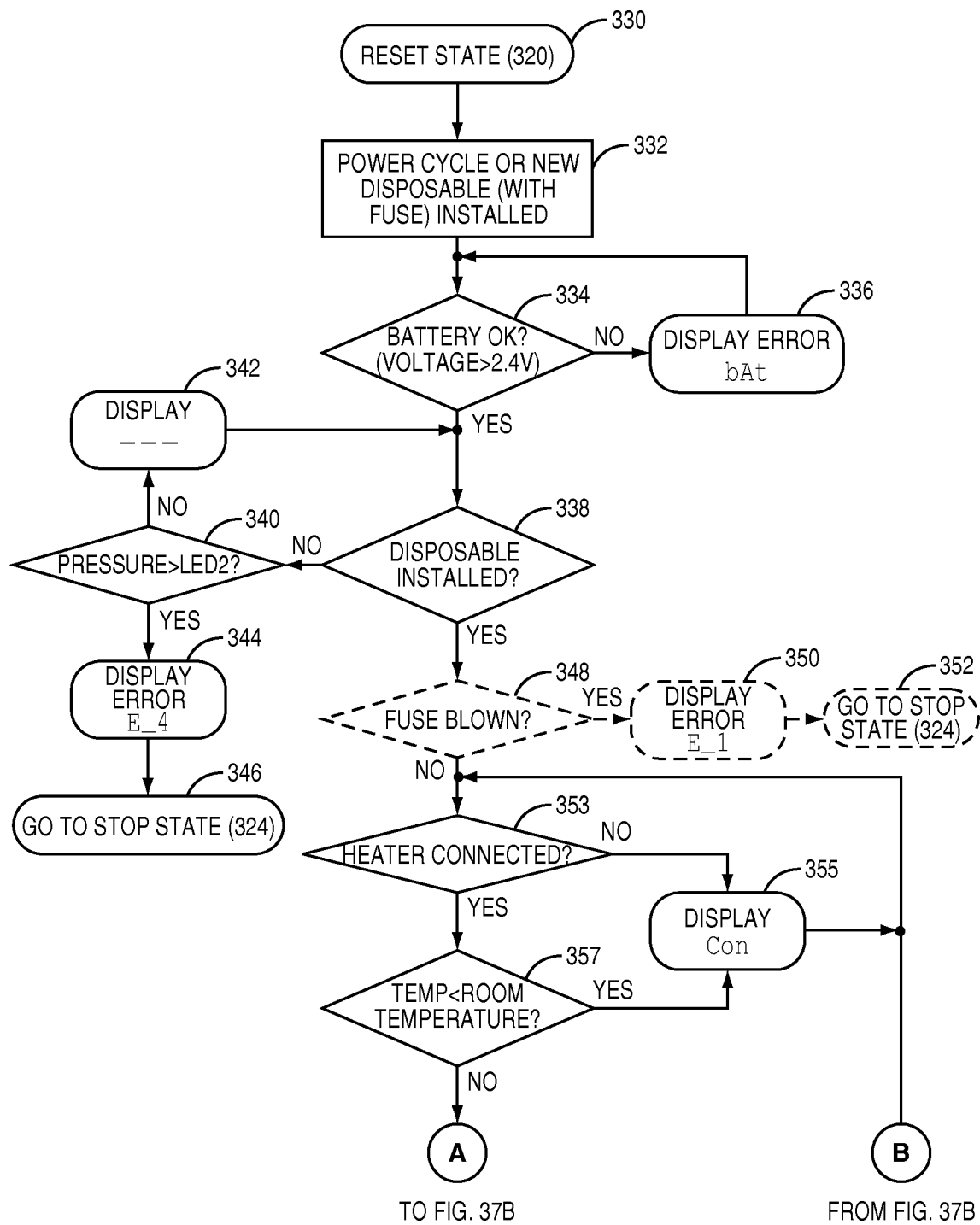
FIGS. 37A and 37B illustrate the "Reset" state flow diagram according to the system state flow diagram of FIG. 36, according to one embodiment relating to the present invention.

FIG. 37A illustrates a flowchart of the reset state 320 (step 330). The controller 166 enters the reset state 320 when either a power cycle occurs or a new disposable lid warmer 130 (with an intact fuse 234 as an optional feature) is installed (step 332). Thereafter, the controller 166 checks to determine if the power supply voltage is above a set minimum voltage level (decision 334). In the disclosed embodiment, the batteries 244 must provide at least 2.4 Volts. If they do not, an battery error (e.g. "bAt") may be displayed on the timer display 180 (step 336). Referring to FIG. 35, the low battery error is displayed by timer and display controller 250 on the timer display 180 in response to the low battery signal sent from the low battery detection circuit 246 over the low battery signal line 248.

If the batteries 244 are producing a sufficient voltage, the controller 166 continues with the reset state 320 by next determining if the disposable component 90 is installed (decision 338). If not, the controller 166 is not ready for operation. However, before going to the stop state 324 (step 346), the controller 166 takes the opportunity to perform a pressure diagnostic test. Referring to FIG. 34, the pressure sensor 230 signal indicative of measured pressure in the tubing 208 is communicated to a pressure level comparator 262, which communicates the pressure level to the pressure display 176 and to an error checking control system 264. Ideally, the pressure in the tubing 208 should not be greater than ambient pressure. If the pressure sensor 230 does not provide a signal indicative of ambient pressure (decision 340), this is an indication that the pressure sensor 230 may not be operating properly. Thus, a pressure sensor 230 error message (e.g. "E_4") may be displayed on the timer display 180 (step 344), via the ERRORS signal line 271 (see FIG. 34), before the controller enters the stop state 324 (step 346). If the pressure sensor 230 is properly measuring pressure, the timer display 180 remains in the reset display state (e.g. "_ _ _") (step 342) and the controller 166 waits until a disposable component 90 is installed (decision 338). Note that because ambient pressure may not be 0 mm Hg depending on where the heat and force application device 70 is located, a threshold pressure level is used. In the disclosed embodiment, the threshold pressure level is 1 psi.

Once the disposable component 90 is installed, the controller 166 can next optionally determine if the fuse 234 on the lid warmer 90 is blown (decision 348). This check is only performed if the lid warmer 90 is equipped with a fuse 234 that can be blown by the controller 166 to indicate when the disposable component 90 has been previously used for a treatment. In this instance and referring to FIG. 34, a fuse detect and blow circuit 268 communicates a fuse detect signal over the FUSE detect line 273 from the interface circuitry 98 on the disposable component 90 to the error check controls system 264. If the fuse 234 is blown, the controller 166 will not allow therapy to be provided using the currently installed disposable component 90 for safety and sterility reasons until the disposable component 90 is replaced with a previously unused disposable component 90 (which will have an intact fuse 234 on the interface circuitry 98). The controller 166 will display an error message (e.g. "E_1") on the timer display 180, via the FUSE signal line 270 to indicate to the user that the disposable component 90 must be replaced (step 350) before going to the stop state 324 (step 352).

If the fuse 234 is not blown on the disposable component 90 (decision 348) or if the fuse check feature is not included in the controller 166, the controller 166 next determines if the heating element 194 is connected (decision 353). If not, the controller displays a connect message (e.g. "Con") on the timer display 180 to indicate to the user that the heating element 194 (i.e. the lid warmer 90) is not connected to the controller 166 and thus therapy cannot begin (step 355). Once the heating element 194 is connected to the controller 166, the controller 166 next determines if the temperature level at the lid warmer 90 is lower than room or ambient temperature (decision 357). If so, this is an indication that the disposable component 90 may not be installed on a patient's eyelid such that the user is ready for the controller 166 to begin therapy. Referring to FIG. 34, thermistor conditioning circuits 272A, 272B communicate signals from each of the thermistors 232A, 232B at the disposable component 90 to the error checking control system 264. In response, the connect message (e.g. "Con") may again be displayed on the timer display 180 (step 355). The controller 166 will continue to check the heating element 194 connection and the temperature at the lid warmer 90 until the thermistors 232A, 232B read a temperature of room temperature or greater (decision 357). This provides some assurance that the disposable component 90 is installed on the patient.

Figure 37B:
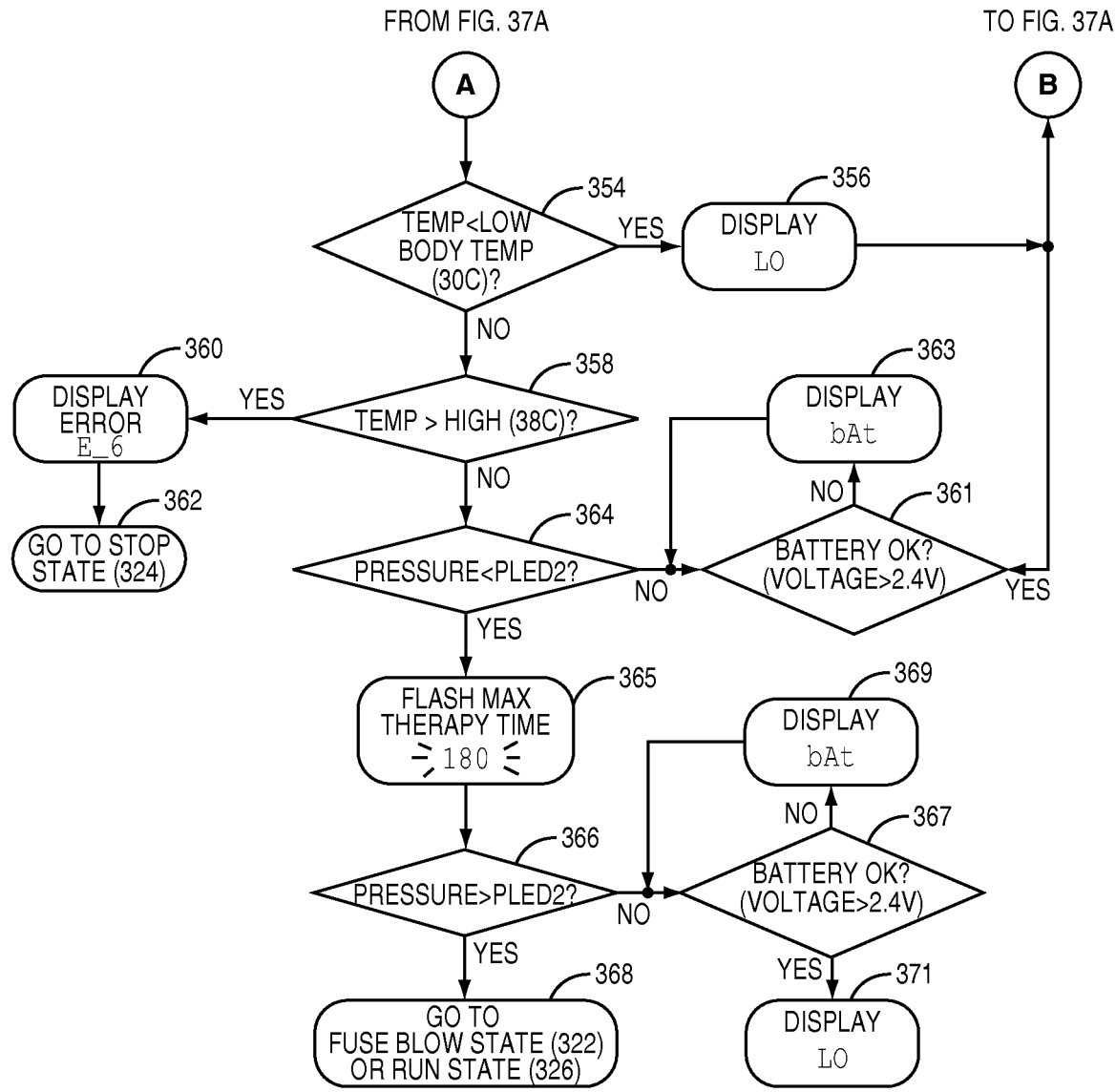

Next, the controller 166 will check to determine if the temperature level at the lid warmer 90 is lower than body temperature (e.g. 30 degrees Celsius) (decision 354 in FIG. 37B). This enables the controller 166 to determine if the disposable component 90 is installed on the patient's eye, because if so installed, the temperature at the lid warmer 90 should be at least body temperature. If the temperature at the lid warmer 90 is not at least body temperature, an error message (e.g. "LO") may be displayed on the timer display 180 in response to indicate to the user that the temperature at the lid warmer 90 is abnormally low (step 356). The controller 166 will thereafter cycle back through the series of checks to ensure that the lid warmer 90 is properly installed and ready for use in therapy (decisions 353, 357, 354, 358).

Once the temperature of the lid warmer 90 is at or above body temperature (decision 354), the controller 166 then determines if the temperature at the lid warmer 90 is at a temperature level that is higher than would be expected before therapy has begun (i.e. an over temperature level, e.g. 30 degrees Celsius) (decision 358). This may be indicative of an ambient temperature that is deemed too high to begin therapy. If so, an error message (e.g. "E_6") may be displayed on the timer display 180 by the error check control system 264 (step 360) before the controller 166 enters the stop state 324 (step 362). If not, the controller will check the pressure level in the tubing 208, via the pressure sensor 230, to ensure pressure level is at ambient pressure since the controller 166 has not inflated the bladder 146 to generate a pressure to the patient's eyelid (decision 364). If the pressure level is lower than ambient pressure, this may be an indication of an error, such as an error with the pressure sensor 230 or the power source. If the pressure level is lower than ambient pressure, the controller 166 will check to determine if the battery voltage is sufficient (decisions 361, 363) and repeat through the series of checks (decisions 353, 357, 354, 358, 364) before allowing therapy to start. Once these series of checks have been satisfied, therapy can begin. In response, the controller 166 will cause the timer display 180 to be reset to indicate the beginning of a therapy session (e.g. a 180 second countdown)(step 365). The controller 166 will then check to ensure that the pressure level in the tubing 208 is not higher than ambient pressure or a desired pressure level that would be indicative of a pressure sensor 230 or other problem (decisions 366, steps 369, 371) before proceeding to the run state 326, or the fuse blow state 322 if provided (step 368).

Figure 38:
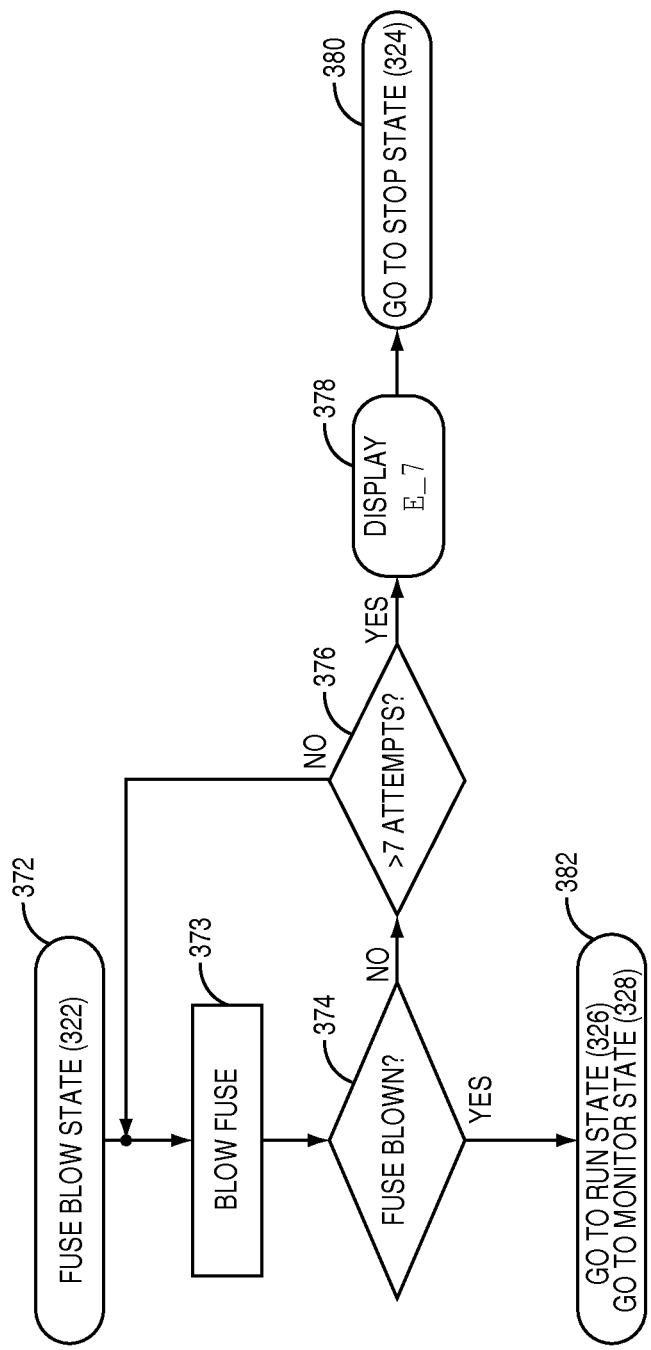
FIG. 38 illustrates the optional "Fuseblow" state flow diagram according to the system state flow diagram of FIG. 36, according to one embodiment relating to the present invention.

After leaving the reset state 320, the controller 166 may go into the fuse blow state 322 (step 372), which is illustrated in FIG. 38. If provided, the controller 166 blows the fuse 234 on the lid warmer 90 so that it cannot be reused after the controller 166 is reset (step 373). Referring to FIG. 34, the error checking control system 264 causes a sufficient current to be sent over the FUSE blow line 274 and to the fuse detect and blow circuitry 268 to blow the fuse 234 at the disposable component 90. The controller 166, via the error check control system 264, then checks to see if the fuse 234 was successfully blown via the FUSE detect line 273 (decision 374). If not, and after at least seven unsuccessful attempts to do so (decision 376), an error message (e.g. "E_7") may be generated on the timer display 180 (step 378) before going to the stop state 324 (step 380). If the fuse 234 is successfully blown, the controller 166 is ready to provide therapy. The controller 166 enters the run and monitor states 326, 328 (step 382) to be executed simultaneously to apply heat and force to the patient's eyelid as well as monitor the temperature and pressure applied for control purposes.

Figure 39:
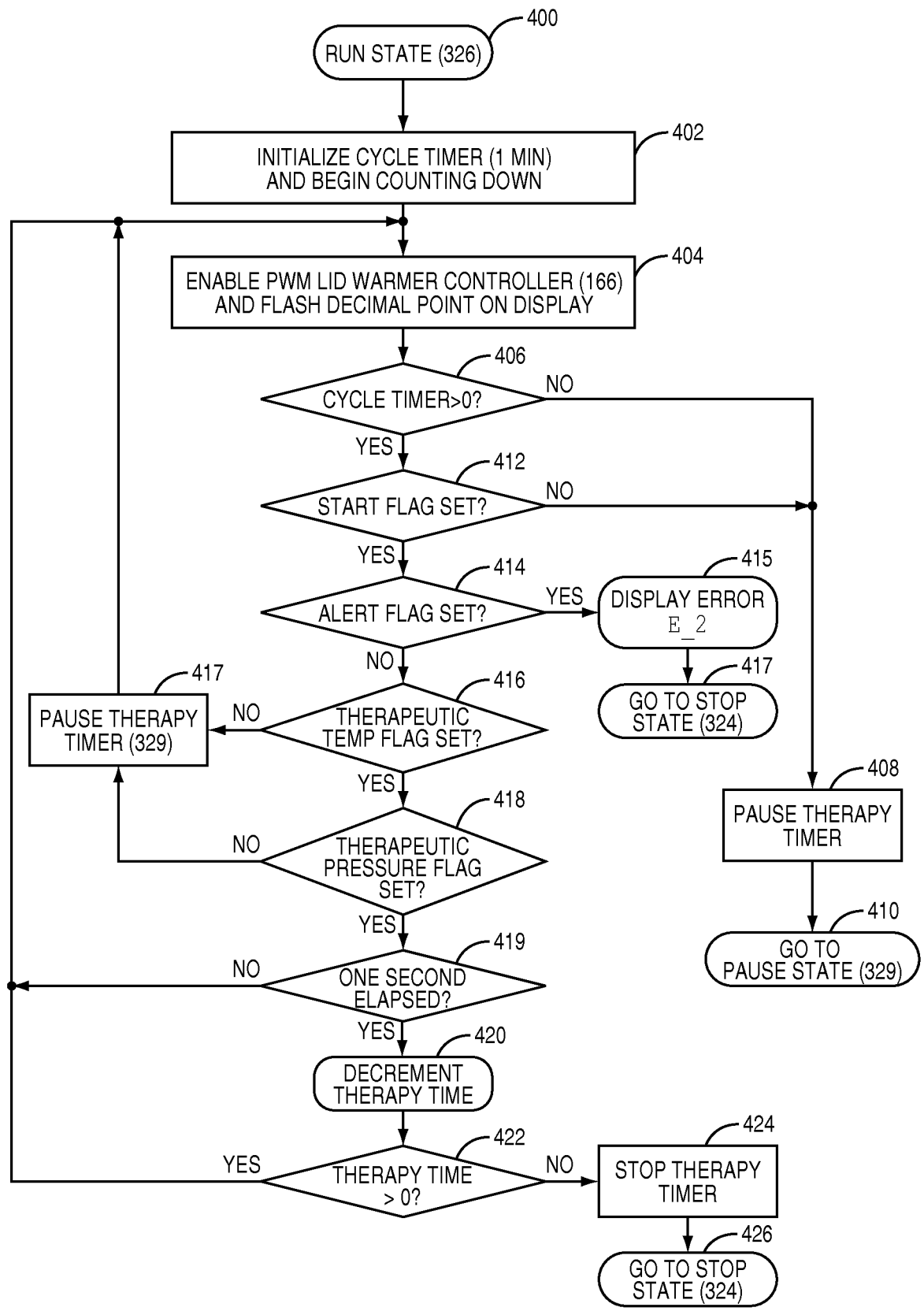
FIG. 39 illustrates the "Run" state flow diagram according to the system state flow diagram of FIG. 36, according to one embodiment relating to the present invention.
Figure 41A:
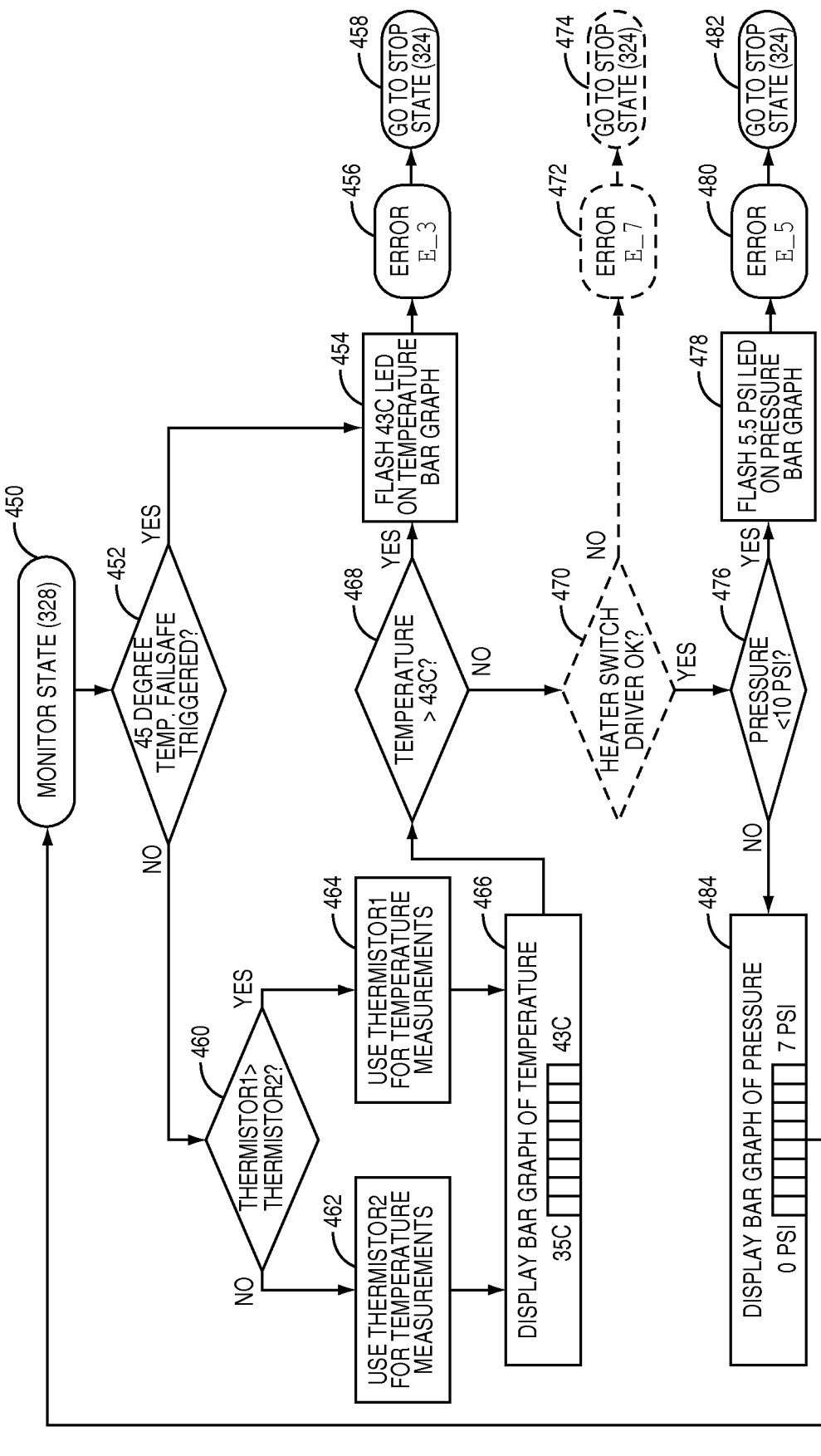
FIGS. 41A and 41B illustrate the "Monitor" state flow diagram according to the system state flow diagram of FIG. 36, according to one embodiment relating to the present invention.
Figure 41B:
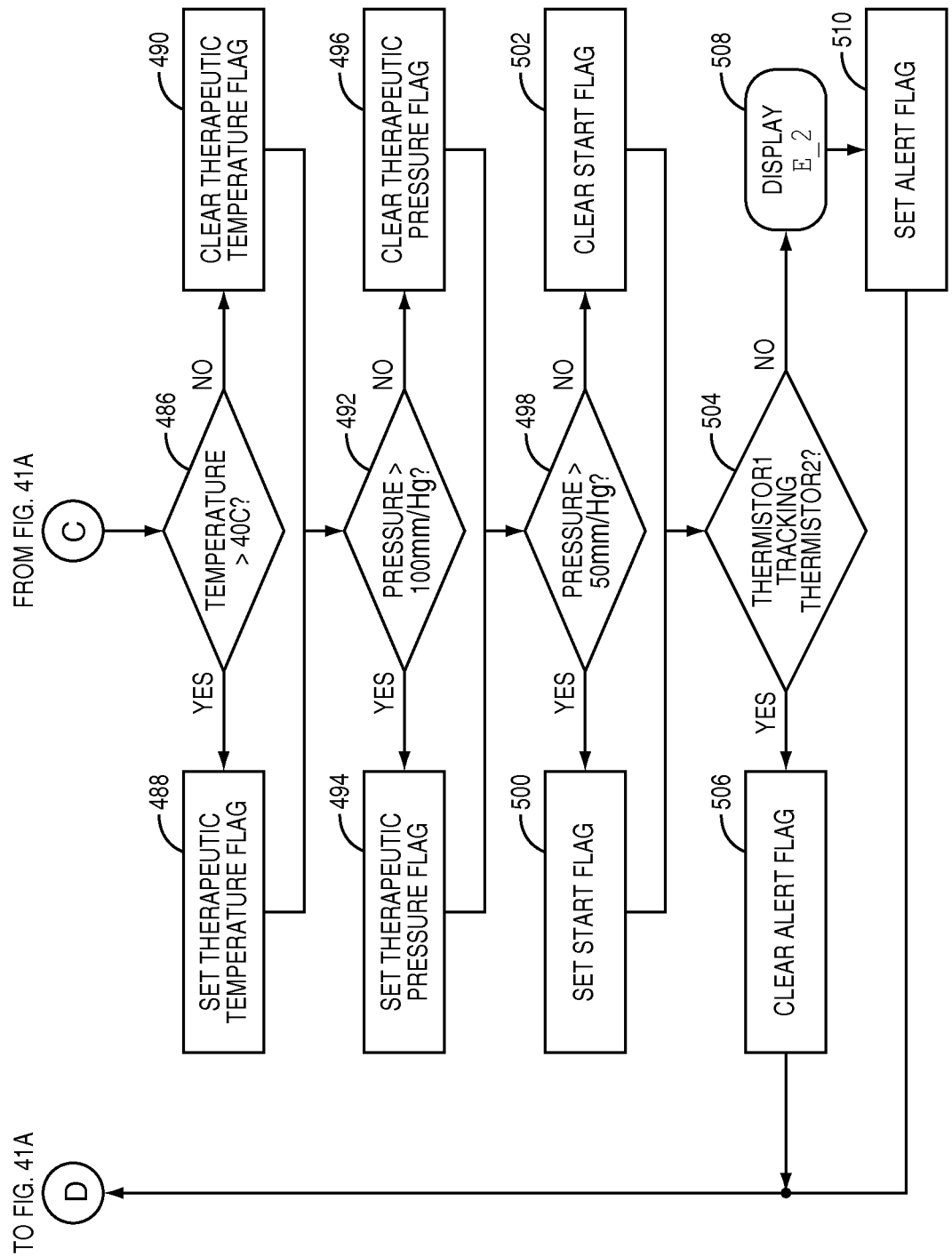

FIG. 39 illustrates the run state 326 (step 400). The controller 166 enters the run state 326 to begin therapy either from the reset state 320 (step 368 in FIG. 21) or optionally from the fuse blow state 322 (step 382 in FIG. 22). The run state 326 will be discussed before the monitor state 328, which is illustrated in FIGS. 41A and 41B. Turning to FIG. 39, the run state 326 begins by the controller 166 initializing a cycle timer and beginning a count down timer at the count down time value programmed into the system (step 402). Turning to FIG. 34, the timer and display controller 250 resets the timers. The count down timer is displayed on the timer display 180. The cycle timer will cause the timer display 180 to blink at the end of a cycle such that the timer display 180 is used to provide the cycle timer and countdown timer information to a user.

In the disclosed embodiment, the cycle timer is the amount of time that force should be applied continuously to the patient's eyelid before being released. In the disclosed embodiment, this is set at one minute. The count down timer is the total therapy time for heat to be applied to the patient's eyelid. In the disclosed embodiment, the count down timer is set at three minutes. Thus, there will be three cycles during the therapy. The timers are not only used to provide a visual timing indicator to the user, but are also used to control heat and force application to the patient's eyelid as will be further discussed. These timer values could also be based on programming instructions provided by the user to the controller 166.

Figure 40:
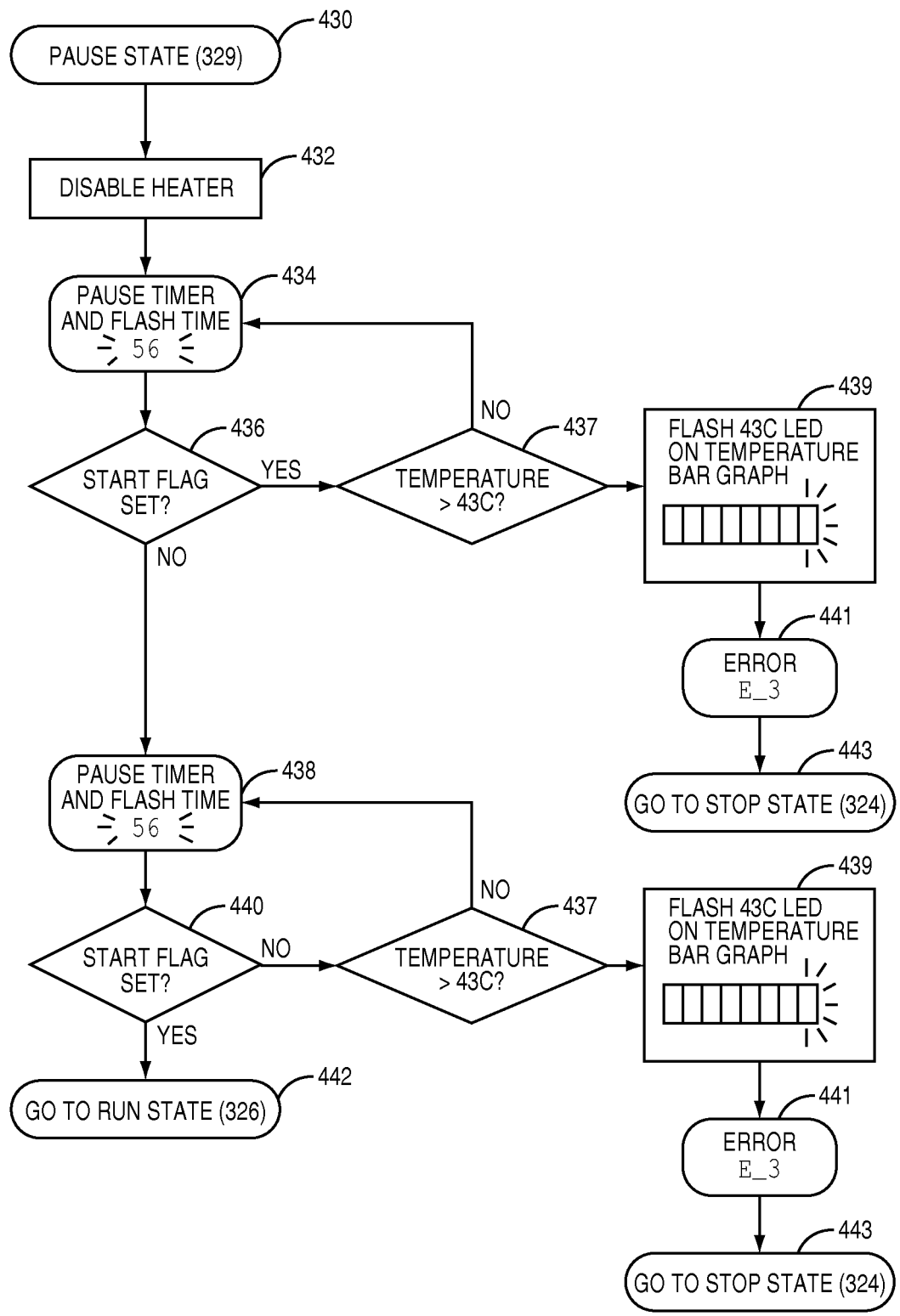
FIG. 40 illustrates the "Pause" state flow diagram according to the system state flow diagram of FIG. 36, according to one embodiment relating to the present invention.

Thereafter, the temperature control system 228 enables heat to be applied to the patient's eyelid via the lid warmer 90 and its lens (step 404). The beginning of heat therapy is signaled to the user by flashing the decimal point on the timer display 180 in the disclosed embodiment (step 404). Referring to FIG. 34, the therapy timer controller 250 causes an enable signal to be generated over an ENABLE line 276 to activate a lid warmer controller 278 to apply an electrical signal to the HEATER+ and HEATER− lines in the electronics wiring 222 (see FIG. 32). This causes the heating element 194 in the lid warmer 90 to energize and generate heat to the patient's eyelid. The lid warmer controller 278 controls the heating element by turning on and off the electrical signal to the heating element 194. However, any type of heating control can be employed, including but not limited to PWM techniques. Thereafter, the timer and display controller 250 determines if the cycle timer has not expired (decision 406). If it has expired, the therapy timer is paused (step 408) and the pause state 329 is entered (step 410). This is because the force must be released before therapy can continue. The pause state 329 is illustrated in FIG. 40 and will be discussed later below.

If the cycle timer has not expired (decision 406), a start, alert, therapeutic temperature, and therapeutic pressure flags are checked (decisions 412, 414, 416, 418). These flags are set by the monitor state 328 as part of error checking, which is illustrated in FIGS. 41A and 41B and will be discussed later below. At this point, all that is required to understand is that these flags being set means that heat therapy can continue. If not, either the stop state 324 (step 417) or the pause therapy timer state 329 (step 408, 417) will be entered before returning back to the run state 326. If the flags are properly set, the therapy timer will be decremented with the elapsed time as each second elapses (steps 419, 420) with heating element 194 continuing to be energized to produce heat at the lid warmer 90 until the therapy time is complete (decision 422). When the therapy time has completed, meaning that the therapy timer time has counted down to zero time in the disclosed embodiment, the therapy timer is stopped (step 424) and the stop state 324 is entered to discontinue heating the patient's eyelid (step 426).

Before describing the monitor state 328, which is illustrated in FIGS. 41A and 41B, the pause state 329 will next be described. The pause state 329 is illustrated in FIG. 40. The pause state 329 is entered to disable energizing the heating element 194 and wait for the user to release the force lever 178 (or other pressure control mechanism) before re-entering the run state 326. This ensures that force is not continuously applied to the patient's eyelid during the entire therapy session without some relief to allow blood flow in the eyelids for safety precaution reasons. The timer and display controller 250 first disables the heating element 194 by removing the enable signal from the ENABLE line 276 to the lid warmer controller 278 (step 432). The timer display 180 is paused from changing, and the cycle time is flashed indicating that the end of the cycle has occurred (steps 434, 438). The start flag is checked (decisions 436, 440) to ensure that the user has released force so that therapy can be restarted, in which case the system returns back to the run state 326 (step 442). The start flag is set and reset in the monitor state 328.

If the start flag is set (decision 436, 440), the controller 166 may also check to determine if the temperature at the lid warmer 90 is above a defined threshold temperature level. If so, this may be indicative of the heating element 194 producing a heat exceeding an upper temperature level of heat to be applied to the patient (decision 437). In the disclosed embodiment, this upper temperature threshold level is 43 degrees Celsius. However, this threshold temperature level can be set to be any temperature level threshold desired. If the threshold temperature level is exceeded, the temperature display 174 may be flashed to indicate this condition to the user as well as an error (e.g. "E_3") being displayed on the timer display 180 (step 439, 441) before the controller 166 enters the stop state 324 (step 443).

The monitor state 328 is illustrated by the flowchart of FIGS. 41A and 41B. The monitor state 328 will continuously check the temperature and pressure applied to the patient's eyelid. Temperature is checked using thermistors 232A, 232B, and pressure is checked using pressure sensor 230 coupled to the tubing 208. The results of the measured temperature and pressure are displayed on the controller 166, via the temperature and pressure displays 82, 84. The temperature and pressure measurements are analyzed to ensure that no error conditions have occurred. In addition, the monitor state 328 will signal to the run state 326, which is executing simultaneously with the monitor state 328, when therapeutic temperatures and pressures have been reached.

Turning to FIG. 41A, the temperature control system 228 determines if the temperature is above a threshold maximum temperature level failsafe for safety reasons (decision 452). This threshold maximum temperature level may be set to 45 degrees Celsius. If so, the over temperature condition is flashed on the temperature display 174 to indicate to the user that the temperature is over the allowed temperature setting (step 454). Further, an error message (e.g. "E_3") may be displayed on the timer display 180 in the same regard (step 456). The controller 166 will enter the stop state 324 (step 458) to halt therapy. If the temperature at the lid warmer 90 is not above the set safe temperature threshold, the error checking controller checks to see if the two temperature thermistors 232A, 232B are different in value (decision 460). The thermistor 232A, 232B providing the higher reading is used for temperature monitoring as an additional precaution to prevent an unsafe temperature from being applied to the patient's eyelid (steps 462, 464). The measured temperature is then displayed on the temperature display 174 (step 466).

The temperature at the thermistor 232A, 232B used to measure the temperature is checked again to ensure that the temperature at the lid warmer 90 has not exceeded the maximum allowable temperature again as a safety precaution (decision 468). If the temperature has exceeded the maximum allowable temperature, the same steps previously performed earlier for this check are performed (steps 454, 456, 458). If not, the heater switch driver in the lid warmer controller 278 may be optionally checked to ensure that it is working correctly to ensure that heat will not be applied to the patient's eyelid when the switch is turned off via the ON/OFF signal line 280 in FIG. 34 (decision 470). If the heater switch driver has a malfunction, an error message (e.g. "E_7") may be generated on the timer display 180 to indicate the hardware failure to the user (step 472). The system then enters the stop state (324) to disable the application of heat (step 474).

If the heater switch driver is operating properly (decision 470), the system determines if the pressure level in the tubing 208 is above the maximum allowable pressure as a safety precaution to prevent too much pressure from being applied to the patient's eyelid (decision 476). If so, the over pressure condition is displayed on the pressure display 176 and the timer display (e.g. "E_5") to indicate the over pressure condition to the user (step 478, 480) before entering the stop state 324 (step 482). If no over pressure condition exists, the measured pressure is displayed on the pressure display 176 (step 484).

Next, as illustrated in FIG. 41B, the system determines if the temperature at the lid warmer 90 is above the therapeutic temperature setting (decision 486). This is an indication that the temperature has risen at the lid warmer 90 necessary to provide therapy and so that the therapy timer will accumulate in the run state 326. The therapeutic temperature setting is set by the system. Alternatively, it may be programmed by the user into the controller 166. If the temperature is above the therapeutic temperature setting (decision 486), the therapeutic temperature flag is set (step 488). If not, the therapeutic temperature flag is cleared (step 490).

In a similar manner to temperature, the system also determines if the pressure in the tubing 208 indicative of the pressure applied to the patient's eyelid is above the therapeutic pressure setting (decision 492). This is an indication that the pressure has risen to a level necessary to provide therapy and so that the therapy timer will accumulate in the run state 326. The therapeutic pressure setting is set by the system. Alternatively, it may be programmed by the user into the controller 166. If the pressure level is above the therapeutic pressure setting (decision 492), the therapeutic pressure flag is set (step 494). If not, the therapeutic pressure flag is cleared (step 496). The system also checks to determine if the pressure level has increased to a minimum threshold level indicative of the force lever 178 being engaged by the user to allow therapy to start (decision 498). If so, the start flag is set (step 500). If not, the start flag is cleared (step 502).

The system also monitors the temperature thermistors 232A, 232B to determine if their measured signals track each other as an indication of whether the thermistors 232A, 232B may have malfunctioned (decision 504). Two thermistors are unlikely to produce the same output for a given temperature, but they change in like kind in response to the same conditions. If they are properly tracking each other, the alert flag is cleared indicating that no error condition exists for the thermistors (step 506). If not, an error message (e.g. "E_2") may be displayed on the timer display 180 (step 508) before the alert flag is set (step 510). As previously discussed, the run state 326 checks the alert flag as a condition of allowing therapy to continue. The monitor state 328 continues to execute in a looping fashion until a condition occurs to place the controller 166 in the stop state 324.

Figure 42:
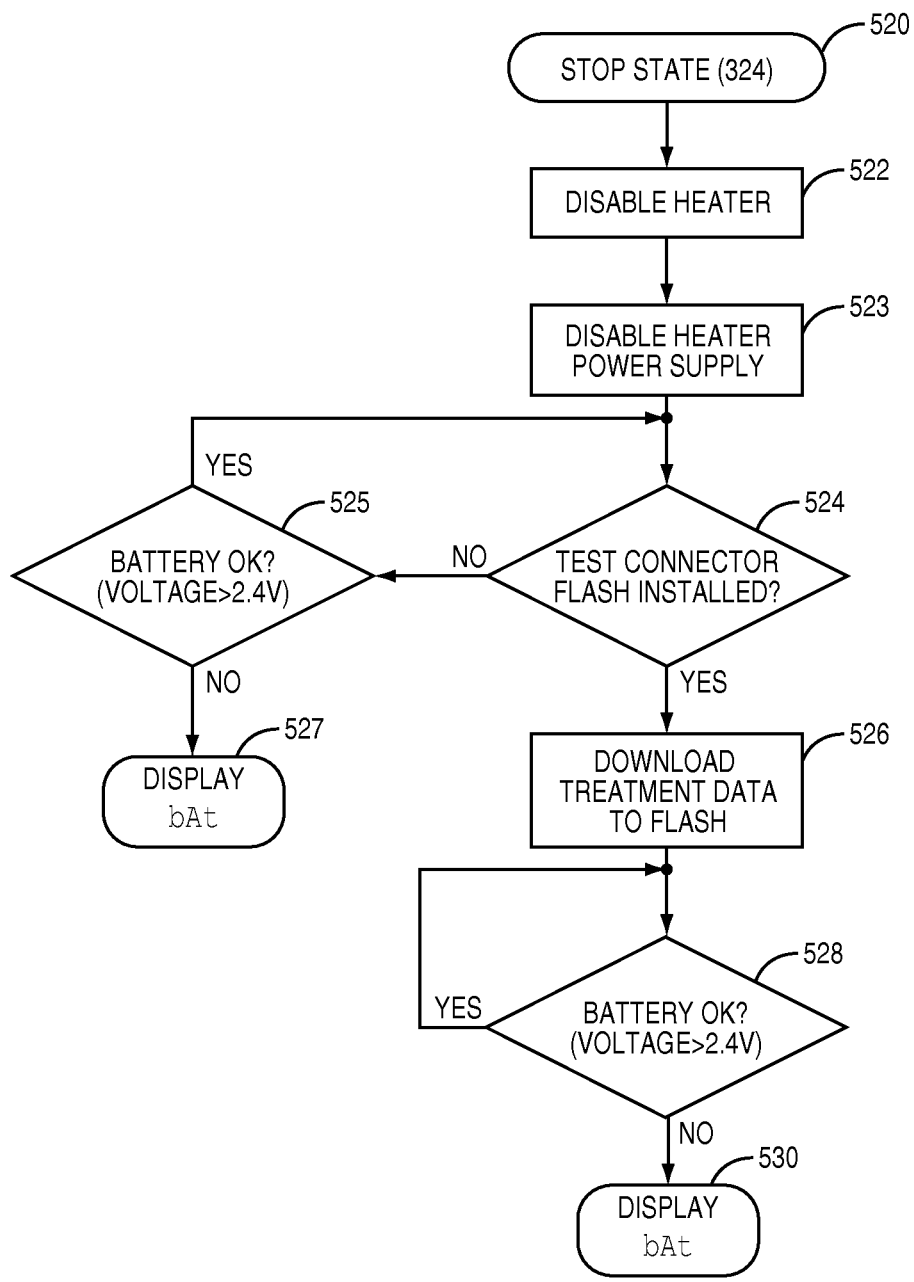
FIG. 42 illustrates the "Stop" state flow diagram according to the system state flow diagram of FIG. 36, according to one embodiment relating to the present invention.

FIG. 42 illustrates the last state of the controller state machine, the stop state 324. The stop state 324 is entered when the total therapy time has reached its preset maximum time or any error condition occurs (step 520). Once in the stop state 324, the controller 166 cannot be restarted with the same disposable component 90 for safety reasons. The heating signal to the heating element 194 is disengaged to stop heat from being applied to the patient's eyelid (step 522). Further, the power supply to the heating element 194 can also be disabled as a further measure to ensure that heat will no longer be applied to the patient's eyelid (step 523). An optional test connector may be installed to download sensor or other operational data to memory for data logging or for testing. If installed (decision 524), the data may be downloaded to memory (step 526). Once the treatment data is downloaded, the controller 166 can check the status of the battery until the controller 166 is reset to enter the reset state 330 (see. FIG. 21), since the controller 166 is not performing therapy and is otherwise dormant (decision 528, step 530). If the test connector is not installed, the controller 166 continues to check for installation of the optional test connector as well as performing a battery level check (decision 525, step 527) until either installed or the controller 166 is reset to enter the reset state 320 (see FIG. 21).

Thereafter, the system enters the run state 326, in which case, therapy can begin again once the error conditions are eliminated and a new disposable component 90 is installed.

Many modifications and other embodiments of the disclosure set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:

1. A method for treating lipid transport deficiency in an ocular tear film, comprising:
    providing at least one mechanical treatment device having at least one textured surface;
    examining a lid margin of an eyelid and identifying specific areas of the lid margin that are impacted by devitalized and/or dead cell material present in a Line of Marx area of the lid margin of the eyelid such that lipids secreted from meibomian glands may not be transported in the ocular tear film; and
    moving one of the at least one textured surface and the lid margin of the eyelid proximate to the Line of Marx area of the lid margin of the eyelid against the other to exfoliate the devitalized and/or dead cell material from specific areas of the lid margin in the Line of Marx area.

2. The method of claim 1, further comprising heating the lid margin prior to moving one of the at least one textured surface and the lid margin against the other.

3. The method of claim 1, wherein moving one of the at least one textured surface and the lid margin against the other comprises applying compression to the eyelid to cause the lid margin to move against the at least one textured surface.

4. The method of claim 1, wherein the at least one textured surface comprises at least one matte surface.

5. The method of claim 1, wherein the at least one textured surface is a roughened surface.

6. The method of claim 1, wherein the at least one textured surface is at least one planar surface.

7. The method of claim 1, wherein the at least one textured surface comprises at least one curved surface.

8. The method of claim 1, further comprising aspirating the lid margin, thereby removing the exfoliated devitalized and/or dead cell material from the lid margin.

9. The method of claim 1, wherein moving one of the at least one textured surface and the lid margin of the eyelid comprises vibrating the at least one textured surface.

10. The method of claim 1, wherein moving one of the at least one textured surface and the lid margin of the eyelid comprises rotating the at least one textured surface.

11. The method of claim 1, wherein the at least one textured surface comprises a plurality of textures, further comprising selecting one of the plurality of textures to be moved against the lid margin prior to moving one of the at least one textured surface and the lid margin against the other.

12. The method of claim 1, wherein the at least one textured surface is oriented such that the at least one textured surface scrapes against the lid margin when the lid margin is moved against the at least one textured surface in a first direction, and the at least one textured surface slides against the lid margin when the lid margin is moved against the at least one textured surface in a second direction opposite the first direction.

13. The method of claim 1, wherein the at least one textured surface comprises a plurality of textures, and wherein moving one of the at least one textured surface and the lid margin of the eyelid causes the plurality of textures to scrape against the lid margin simultaneously.

14. The method of claim 1, wherein the at least one mechanical treatment device comprises an auger and the at least one textured surface comprises a thread of the auger; and wherein:
    moving one of the at least one textured surface and the lid margin against the other comprises:
        moving the thread of the auger into contact with the lid margin proximate to the Line of Marx area; and
        rotating the auger such that the thread of the auger scrapes the exfoliated devitalized and/or dead cell material from the lid margin.

15. The method of claim 14, wherein rotating the auger causes the exfoliated devitalized and/or dead cell material to be removed from the lid margin.

16. An apparatus for treating lipid transport deficiency in ocular tear films, comprising:
    at least one mechanical treatment device comprising an eye cup having a shaft extending from a surface of the eye cup, wherein the surface of the eye cup has at least one first textured surface, at least one second textured surface is located on a surface of the shaft extending from the surface of the eye cup, and at least one of the at least one first textured surface and the at least one second textured surface is configured to be positioned to contact a portion of an eyelid and move against a lid margin of the eyelid proximate to a Line of Marx area of the eyelid to exfoliate devitalized and/or dead cell material from the lid margin.

17. The apparatus of claim 16, further comprising a heater for heating the lid margin prior to moving the at least one mechanical treatment device against the lid margin to exfoliate devitalized and/or dead cell material from the lid margin.

18. The apparatus of claim 16, further comprising a bladder for compressing the eyelid to cause the lid margin to move against at least one of the at least one first textured surface and the at least one second textured surface.

19. The apparatus of claim 16, wherein at least one of the at least one first textured surface and the at least one second textured surface comprises at least one matte surface.

20. The apparatus of claim 16, wherein at least one of the at least one first textured surface and the at least one second textured surface is a roughened surface.

21. The apparatus of claim 16, wherein at least one of the at least one first textured surface and the at least one second textured surface comprises at least one planar surface.

22. The apparatus of claim 16, wherein at least one of the at least one first textured surface and the at least one second textured surface comprises at least one curved surface.

23. The apparatus of claim 16, further comprising an aspirator for aspirating the lid margin to remove the exfoliated devitalized and/or dead cell material from the lid margin.

24. The apparatus of claim 16, further comprising a mechanical energy generator configured to cause at least one of the at least one first textured surface and the at least one second textured surface to vibrate.

25. The apparatus of claim 16, further comprising a mechanical energy generator configured to cause at least one of the at least one first textured surface and the at least one second textured surface to rotate.

26. The apparatus of claim 16, wherein at least one of the at least one first textured surface and the at least one second textured surface comprises a plurality of textures, and the apparatus further comprises a mechanical energy generator configured to move one of the plurality of textures against the lid margin.

27. The apparatus of claim 16, wherein at least one of the at least one first textured surface and the at least one second textured surface is oriented such that at least one textured surface scrapes against the lid margin when the lid margin is moved against the at least one textured surface in a first direction, and the at least one textured surface slides against the lid margin when the lid margin is moved against the at least one textured surface in a second direction opposite the first direction.

28. The apparatus of claim 16, wherein at least one of the at least one first textured surface and the at least one second textured surface comprises a plurality of textures, and the apparatus further comprises a mechanical energy generator configured to cause the plurality of textures to scrape against the lid margin simultaneously.

29. The apparatus of claim 16, wherein the at least one first textured surface on the surface of the eye cup comprises scored lines, grooves, or ridges on the surface of the eye cup that run parallel to the surface of the eye cup.

30. The apparatus of claim 16, wherein the at least one mechanical treatment device comprises an auger and at least one of the at least one first textured surface and the at least one second textured surface comprises a thread of the auger, and wherein the at least one mechanical treatment device is configured to:
  move the thread of the auger into contact with the lid margin of the eyelid proximate to the Line of Marx area; and
  rotate the auger such that the thread of the auger scrapes the exfoliated devitalized and/or dead cell material from the lid margin.

31. The apparatus of claim 30, wherein the thread of the auger is further configured to remove the exfoliated devitalized and/or dead cell material from the lid margin.

32. An apparatus for treating lipid transport deficiency in ocular tear films, comprising:
  at least one mechanical treatment device comprising an eye cup configured to be placed over an eye of a patient and contact an eyelid,
  wherein a surface of the eye cup has at least one textured surface, and
  wherein the at least one textured surface is configured to be positioned to contact a portion of the eyelid and move against a lid margin of the eyelid proximate to a Line of Marx area of the eyelid to exfoliate devitalized and/or dead cell material from the lid margin.

* * * * *